(12) United States Patent
Dunham et al.

(10) Patent No.: US 11,033,581 B2
(45) Date of Patent: Jun. 15, 2021

(54) METHODS AND TREATMENT OF TRAUMA ADVERSE EVENTS WITH OXYGEN REDUCED BLOOD

(71) Applicant: Hemanext Inc., Lexington, MA (US)

(72) Inventors: Andrew Dunham, Lexington, MA (US); Tatsuro Yoshida, Lexington, MA (US)

(73) Assignee: Hemanext Inc., Lexington, MA (US)

( * ) Notice: Subject to any disclaimer, the term of this patent is extended or adjusted under 35 U.S.C. 154(b) by 0 days.

(21) Appl. No.: 16/849,614

(22) Filed: Apr. 15, 2020

(65) Prior Publication Data

US 2020/0237818 A1    Jul. 30, 2020

Related U.S. Application Data

(63) Continuation of application No. 16/791,697, filed on Feb. 14, 2020, now Pat. No. 10,898,517, which is a continuation of application No. 16/614,683, filed as application No. PCT/US2018/033404 on May 18, 2018.

(60) Provisional application No. 62/508,783, filed on May 19, 2017.

(51) Int. Cl.
*A61K 35/14*    (2015.01)
*A61P 7/04*    (2006.01)

(52) U.S. Cl.
CPC ............... *A61K 35/14* (2013.01); *A61P 7/04* (2018.01)

(58) Field of Classification Search
None
See application file for complete search history.

(56) References Cited

U.S. PATENT DOCUMENTS

| | | | |
|---|---|---|---|
| 4,769,318 A | 9/1988 | Hamasaki et al. | |
| 4,880,786 A | 11/1989 | Sasakawa et al. | |
| 5,476,764 A | 12/1995 | Birensky | |
| 5,624,794 A | 4/1997 | Bitensky et al. | |
| 5,789,151 A | 8/1998 | Bitensky et al. | |
| 6,162,396 A | 12/2000 | Bitensky et al. | |
| 6,413,713 B1 | 7/2002 | Serebrennikov | |
| 6,447,987 B1 | 9/2002 | Hess et al. | |
| 2018/0133255 A1* | 5/2018 | Yoshida | A61K 35/18 |
| 2018/0338488 A1* | 11/2018 | Wolf | A01N 1/021 |
| 2019/0388467 A1* | 12/2019 | D'Alessandro | A61P 9/00 |

OTHER PUBLICATIONS

Holcomb, J. Optimal Use of Blood Products in Severely Injured Trauma Patients. Hematology 465-469, 2010. (Year: 2010).*
Brown., "Length of red cell unit storage and risk for delirium after cardiac surgery," *Anesth Analg* 119:242-250 (2014), See U.S. Appl. No. 16/791,697.
Chaplin et al., "The Proper Use of Previously Frozen Red Blood Cells for Transfusion," *Blood* 59:1118-1120 (1982), See U.S. Appl. No. 16/791,697.
Ciccia et al., "Pediatric acute kidney injury: prevalence, impact and management challenges," *Int J Nephrol Renovasc Dis* 10:77-84 (2017), See U.S. Appl. No. 16/791,697.
D'Alessandro et al., "Metabolomics of AS-5 RBCs supernatants following routine storage," *Vox sanguinis* (2014), See U.S. Appl. No. 16/791,697.
D'Alessandro et al., "An update on red blood cell storage lesions, as gleaned through biochemistry and omics technologies," *Transfusion* 55:205-219 (2015), See U.S. Appl. No. 16/791,697.
D'Alessandro et al., "Routine storage of red blood cell (RBC) units in additive solution-3: a comprehensive investigation of the RBC metabolome," *Transfusion* 55:1155-1168 (2015), See U.S. Appl. No. 16/791,697.
D'Alessandro et al., "Red blood cell storage in additive solution-7 preserves energy and redox metabolism: a metabolomics approach," *Transfusion* (2015), See U.S. Appl. No. 16/791,697.
D'Alessandro et al., "Citrate metabolism in red blood cells stored in additive solution-3," *Transfusion* (2016), See U.S. Appl. No. 16/791,697.
D'Alessandro et al., "Omics markers of the red cell storage lesion and metabolic linkage," *Blood Transfus* 15:137-144 (2017), See U.S. Appl. No. 16/791,697.
Flegel et al., "Does prolonged storage of red blood cells harm?" *British journal of haematology* 165:3-16 (2014), See U.S. Appl. No. 16/791,697.
Fox et al., "Earlier Endpoints are Required for Hemorrhagic Shock Trials Among Severely Injured Patients," *Shock* 47:567-573 (2017), See U.S. Appl. No. 16/791,697.
Gowda et al., "Markers of renal function tests," *N Am J Med Sci* 2(4):170-173 (2010), See U.S. Appl. No. 16/791,697.
Hashmi et al., "Predictors of mortality of geriatric trauma patients: a systematic review and meta-analysis," *The journal of trauma and acute care surgery* 76:894-901 (2014), See U.S. Appl. No. 16/791,697.
Hod et al., "Transfusion of human volunteers with older, stored red blood cells produces extravascular hemolysis and circulating non-transferrin-bound iron," *Blood* 118:6675-6682 (2011), See U.S. Appl. No. 16/791,697.
Jy et al., "Microparticles in stored red blood cells as potential mediators of transfusion complications," *Transfusion* 51:886-893 (2011), See U.S. Appl. No. 16/791,697.
Kim-Shapiro et al., "Storage lesion: role of red blood cell breakdown," *Transfusion* 51:844-851 (2011), See U.S. Appl. No. 16/791,697.
Kreutziger et al., "Admission blood glucose predicted hemorrhagic shock in mortality in trauma patients," *Injury* 46:15-20 (2015), See U.S. Appl. No. 16/791,697.
Laird et al., "Relationship of early hyperglycemia to mortality in trauma patients," *J Trauma* 56:1058-1062 (2004), See U.S. Appl. No. 16/791,697.
Liu et al., "Mechanism of faster NO scavenging by stored red blood cells," *Redox biology* 2:211-219 (2014), See U.S. Appl. No. 16/791,697.
Norton et al., "Global Health Injuries," *The NEJM* 368:1723-1730 (2013), See U.S. Appl. No. 16/791,697.

(Continued)

*Primary Examiner* — Ralph J Gitomer
(74) *Attorney, Agent, or Firm* — Arnold & Porter Kaye Scholer LLP

(57) ABSTRACT

Methods for the reversal of hemorrhagic shock or hemorrhagic trauma. Methods for restoring mean arterial pressure to a normal range and reducing trauma adverse risks in a patient through the administration of oxygen reduced blood compositions.

22 Claims, 33 Drawing Sheets

(56) References Cited

OTHER PUBLICATIONS

Prestia et al., "Transfusion of stored blood impairs host defenses against Gram-negative pathogens in mice," *Transfusion* 54:2842-2851 (2014), See U.S. Appl. No. 16/791,697.
Redlin et al., "Red blood cell storage duration is associated with various clinical oucomes in pediatric cardiac surgery," *Transfusion medicine and hemotherapy: offizielles Organ der Deutschen Gesellschaft fur Transfusionsmedizin and Immunhamatologie* 41:146-151 (2014), See U.S. Appl. No. 16/791,697.
Rogers et al., "Storage duration of red blood cell transfusion and Clostridium difficile infection: a within person comparison," *PLoS One* 9:e89332 (2014), See U.S. Appl. No. 16/791,697.
Roback et al., "Insufficient nitric oxide bioavailability: a hypothesis to explain adverse effects of red blood cell transfusion," *Transfusion* 51:859-866 (2011), See U.S. Appl. No. 16/791,697.
Roback et al., "Metabolomics of AS-1 RBCs Storage," *Transfusion medicine reviews* (2014), See U.S. Appl. No. 16/791,697.
Reynolds et al., "The transfusion problem: role of aberrant S-nitrosylation," *Transfusion* 51:852-858 (2011), See U.S. Appl. No. 16/791,697.
Reisz et al., "Oxidative modifications of glyceraldehyde 3-phosphate dehydrogenase regulate metabolic reprogramming of stored red blood cells," *Blood* 128:e32-42 (2016), See U.S. Appl. No. 16/791,697.
Regnier et al., "Prognostic significance blood lactate and lactate clearance in trauma patients," *Anesthesiology* 117:1276-1288 (2012), See U.S. Appl. No. 16/791,697.
Spinella et al., "Does the storage duration of blood products affect outcomes in critically ill patients," *Transfusion* 51:1644-1650 (2011), See U.S. Appl. No. 16/791,697.
Spinella et al., "Properties of stored red blood cells: understanding immune and vascular reactivity," *Transfusion* 51:894-900 (2011), See U.S. Appl. No. 16/791,697.
Treeprasertsuk et al., "Urine neutrophil gelatinase-associated lipoclin: a diagnostic and prognostic marker for acute kidney injury (AKI) in hospitalized cirrhotic patients with AKI-prone conditions," *BMC Gastroenterol* 15:140 (2015), See U.S. Appl. No. 16/791,697.
Valeri et al., "The survival, function, and hemolysis of human RBCs stored at 4 degrees C in additive solution (AS-a, AS-3, or AS-5) for 42 days and then biochemically modified, frozen, thawed, washed, and stored at 4 degrees C in sodium chloride and glucose solution for 24 hours," *Transfusion* 40:1341-1350 (2000), See U.S. Appl. No. 16/791,697.
Wang et al., "Transfusion of older stored blood worsens outcomes in canines depending on the presence of severity of pneumonia," *Transfusion* 54:1712-1724 (2014), See U.S. Appl. No. 16/791,697.
Weinberg et al., "Red blood cell age and potentiation of transfusion-related pathology in trauma patients," *Transfusion* 51:867-873 (2011), See U.S. Appl. No. 16/791,697.
Wither et al., "Hemoglobin oxidation at functional amino acid residues during routine storage of red blood cells," *Transfusion* (2016), See U.S. Appl. No. 16/791,697.
Yoshida et al., "Extended storage of red blood cells under anaerobic conditions," *Vox sanguinis* 92:22-31 (2007), See U.S. Appl. No. 16/791,697.
Yoshida et al., "The effects of additive solution pH and metabolic rejuvenation on anaerobic storage of red cells," *Transfusion* 48:2096-2105 (2008), See U.S. Appl. No. 16/791,697.
Yoshida et al., "Reduction of microparticle generation during anaerobic storage of red blood cells," *Transfusion* 52, 83A (2012), See U.S. Appl. No. 16/791,697.
Zhang et al., "Lactate clearance is a useful biomarker for the prediction of all-cause mortality in critically ill patients: a systematic review and meta-analysis," *Critical care medicine* 42:2118-2125 (2014), See U.S. Appl. No. 16/791,697.
Zimring, "Established and theoretical factors to consider in assessing the red cell storage lesion," *Blood* 125:2185-2190 (2015), See U.S. Appl. No. 16/791,697.
Zhu et al., "Impaired adenosine-5'-triphosphate release from red blood cells promotes their adhesion to endothelial cells: a mechanism of hypoxemia after transfusion," *Critical care medicine* 39:2478-2486 (2011), See U.S. Appl. No. 16/791,697.

* cited by examiner

METHODS AND TREATMENT OF TRAUMA ADVERSE EVENTS WITH OXYGEN REDUCED BLOOD

CROSS-REFERENCE TO RELATED APPLICATION

This application claims priority to U.S. Provisional Application No. 62/508,783, filed May 19, 2017, which is hereby incorporated by reference in its entirety.

GOVERNMENT RIGHTS

This invention was made with the United States government support under R44HL132172 awarded by the National Heart, Lung, and Blood Institute. The government has certain rights in the invention.

FIELD OF THE INVENTION

The present disclosure relates to treatment of trauma and hemorrhagic shock.

BACKGROUND OF THE INVENTION

In 2010, there were 5.1 million deaths from injuries, surpassing the number of deaths due to HIV, tuberculosis, and malaria combined (3.8 million). See Norton, et al., "Global Health Injuries" in *The NEJM,* 368:1723-30 (2013) ("Norton 2013") (hereby incorporated by reference in its entirety). Injuries include unintentional injuries (e.g., road-traffic incidents, falls, and burns) and intentional injuries self-harm, interpersonal violence, war and conflict), See Norton 2013. The number of deaths from injuries increased by 24% between 1990 and 2010, worldwide, and increased 23% between 2000 and 2010, in the United States. See Norton 2013. Additionally, at least 20% of all trauma deaths are the result of survivable injuries and are therefore preventable with optimal care. Fox et al., "Earlier Endpoints are Required for Hemorrhagic Shock Trials Among Severely Injured Patients."*Shock,* 47:567-73 (2017) (hereby incorporated by reference in its entirety). The percentage of preventable deaths make it imperative to develop therapy for avoidable complications which lead to mortality.

Penetrating wounds (e.g., gunshot or stabbing) and blunt trauma (e.g., fall or automobile accident) are major causes of hemorrhagic trauma. The resulting shock is a condition of inadequate oxygen supply to tissues from massive hemorrhage causing oxygen debt, anaerobic metabolism and raise of plasma lactate level. Failure to reverse shock by restoring circulation and oxygen delivery can result in permanent tissue damage, multiple organ failure and mortality.

Clinical sequelae of hemorrhagic trauma and shock include mortality from exsanguination within several hours of trauma, as well as after 24 hours from morbidity from trauma and massive transfusion. Such morbidity includes multiple organ failure including lung, kidney, liver from acute traumatic coagulopathy or inflammation, and infection/sepsis from transfusion related immune modulation; both morbidities are heightened by lower quality of transfused blood products as well as higher volume of transfused pRBC.

One approach for treating hemorrhage shock is the use of crystalloids for resuscitation. However, the use of crystalloids result in increased morbidity and mortality by causing trauma induced coagulopathy. For at least this reason, early administration of blood components is advocated for reversing shock caused by hemorrhagic trauma. Packed red blood cells (pRBCs) are transfused into a hemorrhagic trauma patient to restore lost blood volume, restore oxygen carrying capacity in patients and restore oxidative metabolism in tissue from anaerobic metabolism. However, the use of pRBCs is not without risk of complications, including antigen mismatch, pathogen transmission, circulatory overload, and degradation of pRBCs during ex vivo storage.

When stored conventionally, stored blood undergoes a steady deterioration which is associated with various storage lesions including, among others, hemolysis, hemoglobin degradation, and reduced ATP and 2,3-DPG concentrations. When transfused into a patient, the effects of the steady deterioration during storage manifest, for example, as a reduction in the 24-hour in vivo recovery. The rapid decrease in the hematocrit that results from reduced 24-hour recovery, when severe, can result in delayed hemolytic transfusion reaction (DHTR). Other complications, for example systemic inflammatory response syndrome (SIRS), transfusion related acute lung injury (TRALI), and transfusion related immunomodulation (TRIM) are associated with transfusion of stored blood, though identification of the underlying causes has remained unclear.

Even when transfused within the current 6-week limit, stored RBCs tend to exhibit lower quality (e.g. increased fraction of RBCs removed; compromised oxygen exchange capacity; reduced deformability) and increased toxicity, often manifested as the clinical sequelae of transfusion therapy. A large and growing number of articles in the literature supports this view. See Zimring, "Established and theoretical factors to consider in assessing the red cell storage lesion," *Blood,* 125:2185-90 (2015); Zhu et al., "Impaired adenosine-5'-triphosphate release from red blood cells promotes their adhesion to endothelial cells: a mechanism of hypoxemia after transfusion," *Critical care medicine.* 39:2478-86 (2011); Weinberg et al., "Red blood cell age and potentiation of transfusion-related pathology in trauma patients," *Transfusion,* 51:867-73 (2011); Spinella et al., "Does the storage duration of blood products affect outcomes in critically ill patients?" *Transfusion* 51:1644-50 (2011); Rohack et al., "Insufficient nitric oxide bioavailability: a hypothesis to explain adverse effects of red blood cell transfusion," *Transfusion,* 51:859-66 (2011); Reynolds et al., "The transfusion problem: role of aberrant S-nitrosylation," *Transfusion,* 51:852-8 (2011); Kim-Shapiro et al., "Storage lesion: role of red blood cell breakdown," *Transfusion,* 51:844-51 (2011); Jy et al., "Microparticles in stored red blood cells as potential mediators of transfusion complications," *Transfusion,* 51:886-93 (2011); Hod et al., "Transfusion of human volunteers with older, stored red blood cells produces extravascular hemolysis and circulating non-transferrin-bound iron," *Blood,* 118:6675-82 (2011); Flegel et al., "Does prolonged, storage of red blood cells cause harm?" *British journal of haematology* 165:3-16 (2014); Redlin et al., "Red blood cell storage duration is associated with various clinical outcomes in pediatric cardiac surgery," *Transfusion medicine and hemotherapy*: offizielles Organ der Deutschen Gesellschaft fur Transfusionsmedizin and Immunhamatologie 41:146-51 (2014); Rogers et al., "Storage duration of red blood cell transfusion and *Clostridium difficile* infection: a within person comparison," *PLoS One* 9:e89332 (2014); Spinella et al., "Properties of stored red blood cells: understanding immune and vascular reactivity,"*Transfusion* 51:894-900 (2011); Brown et al., "Length of red cell unit storage and risk for delirium after cardiac surgery," *Anesth Analg.* 119:242-50 (2014); Wang et al., "Transfusion of older stored blood worsens outcomes in canines depending on the presence and severity of pneumonia," *Transfusion*, 54:1712-24 (2014); Liu et al., "Mechanism of faster NO scavenging by older stored red blood cells," *Redox biology*, 2:211-9 (2014); Prestia et al., "Transfusion of stored blood impairs host defenses against Gram-negative pathogens in mice," *Transfusion* 54:2842-51 (2014). D'Alessandro et al., "An update on red blood cell storage lesions, as gleaned through biochemistry and omics technologies," *Transfusion*, 55:205-19 (2015) (hereby incorporated by reference in their entireties). An extensive body of in vitro studies unequivocally shows the degradation of RBCs (storage lesions) during conventional storage. A body of emerging metabolomic studies show the development of storage lesions at the molecular level. See Roback et al., "Metabolomics of AS-1 RBCs Storage," *Transfusion medicine reviews* (2014); D'Alessandro et al., "Metabolomics of AS-5 RBCs supernatants following routine storage," *Vox sanguinis* (2014); D'Alessandro et al., "Routine storage of red blood cell (RBC) units in additive solution-3: a comprehensive investigation of the RBC metabolome," *Transfusion* 55:1155-68 (2015); D'Alessandro et al., "Red blood cell storage in additive solution-7 preserves energy and redox metabolism: a metabolomics approach," *Transfusion* (2015); Wither et al., "Hemoglobin oxidation at functional amino acid residues during routine storage of red blood cells," *Transfusion* (2015); D'Alessandro et al., "Citrate metabolism in red blood cells stored in additive solution-3," *Transfusion* (2016); D'Alessandro et al., "Omics markers of the red cell storage lesion and metabolic linkage," *Blood Transfus*, 15:137-44 (2017) (hereby incorporated by reference in their entireties). There is a need for reducing or preventing this degradation to increase the efficacy of transfusions (more $O_2$ delivery to peripheral tissues immediately after transfusion) and to reduce mortality due to hemorrhagic trauma.

Oxidative damage initiates many RBC storage lesions in conventionally stored blood and their downstream consequences; thus, methods to reduce the extent of oxidative stress are required to reduce the RBC storage lesions. A number of approaches have been developed aimed at minimizing storage lesions and improving transfusion outcomes. Approaches include additive solutions (for example, U.S. Pat. No. 4,769,318 to Hamasaki et al. and U.S. Pat. No. 4,880,786 to Sasakawa et al. U.S. Pat. No. 6,447,987 to Hess et al.), frozen storage (see U.S. Pat. No. 6,413,713 to Serebrennikov Chaplin et al, "Blood Cells for Transfusion," *Blood*, 59: 1118-20 (1982), and Valeri et al., "The survival, function, and hemolysis of human RBCs stored at 4 degrees C. in additive solution (AS-1, AS-3, or AS-5) for 42 days and then biochemically modified, frozen, thawed, washed, and stored at 4 degrees C. in sodium chloride and glucose solution for 24 hours," *Transfusion*, 40:1341-5 (2000)) (hereby incorporated by reference in their entireties).

One approach that has proven successful in improving blood quality and extending its utility is through the depletion of oxygen and storage under anaerobic conditions. Among the benefits of storing blood under oxygen depleted conditions are improved levels of ATP and 2,3-DPG, and reduced hemolysis. U.S. Pat. No. 5,624,794 to Bitensky et al., U.S. Pat. No. 6,162,396 to Bitensky et al., and U.S. Pat. No. 5,476,764 to Bitensky (hereby incorporated by reference in their entireties) are directed to the storage of red blood cells under oxygen-depleted conditions. U.S. Pat. No. 5,789,151 to Bitensky et al. is directed to blood storage additive solutions (hereby incorporated by reference in its entirety). U.S. Pat. No. 6,162,396 to Bitensky et al. (the '396 patent) (hereby incorporated by reference in its entirety) discloses anaerobic storage bags for blood storage that comprise an oxygen impermeable outer layer, a red blood cell (RBCs) compatible inner layer that is permeable to oxygen, and having an oxygen scrubber placed between the inner and outer layers.

Storing blood under oxygen depleted conditions can also result in reduced microparticle levels, reductions in the loss of deformability, reduced lipid and protein oxidation and higher post transfusion survival when compared to blood stored under conventional conditions, See Yoshida et al., "The effects of additive solution pH and metabolic rejuvenation on anaerobic storage of red cells," Transfusion 48:2096-2105 (2008) and Yoshida, T, et al. "Reduction of microparticle generation during anaerobic storage of red blood cells. Transfusion", 52, 83A (2012) (hereby incorporated by reference in their entireties). Anaerobically stored RBCs further provide higher 24-hour in vivo recovery after autologous transfusion, higher 2,3-DPG and ATP levels, lower hemolysis, and beneficial remodeling of metabolic pathway. See Reisz et al. "Oxidative modifications of glyceraldehyde 3-phosphate dehydrogenase regulate metabolic reprogramming of stored red blood cells," *Blood*, 128:e32-42 (2016); and Yoshida et al., "Extended storage of red blood cells under anaerobic conditions," *Vox sanguinis* 92:22-31 (2007) (hereby incorporated by reference in their entireties).

In the present disclosure, we demonstrate that oxygen reduced (OR) or oxygen and carbon dioxide reduced (OCR) blood from rats provides improved ATP and 2,3-DPG during storage compared to conventionally stored blood, as has been previously demonstrated using human blood. Thus, OR or OCR rat RBCs are expected to have similar reductions in microparticles, improved deformability, reduced lipid and protein oxidation and higher post transfusion survival.

Here we demonstrate for the first time that OR and OCR blood in rats provides for surprising improvements in clinical outcomes when transfused to treat hemorrhagic trauma. Using a rat hemorrhagic shock resuscitation model, we show that OR or OCR RBCs provide for reduced organ damage relative to conventionally stored blood. In addition, OR or OCR RBCs provide for reversal of the shock state using smaller pRBC volumes. Finally, OR or OCR RBCs, when transfused to treat hemorrhagic shock more rapidly stabilized hemodynamics compared to conventionally stored pRBC of same storage duration.

OR and OCR RBCs provide for improved methods for treatment of trauma resulting in exsanguination to reduce mortality and morbidity over conventionally stored blood. OR and OCR RBCS provide for reduced organ failure, including reductions in levels of markers of lung and liver damage. OR and OCR RBCs further provide reductions in the amounts of blood necessary to restore and stabilize hemodynamic function. Thus, OR and OCR RBCs can provide for reducing the volume of RBCs required for transfusion therapy when treating hemorrhagic trauma. The improved quality of OR and OCR, in addition to the previously demonstrated improvements to the ability of stored RBCs to deliver oxygen, also provides for unexpected reductions in organ damage, morbidity, and mortality associated with trauma.

SUMMARY OF THE INVENTION

The present disclosure provides for, and includes, a method for treating low mean arterial pressure in a subject in need thereof comprising providing stored oxygen reduced blood having an oxygen saturation of 20% or less prior to and during storage, wherein the mean arterial pressure in the subject in need thereof is increased after providing the oxygen reduced blood to the subject in need thereof, and wherein the low mean arterial pressure is due to hemorrhagic trauma.

The present disclosure provides for, and includes, a method for reducing the amount of blood needed for transfusion in a trauma patient in need thereof comprising providing oxygen reduced blood having an oxygen saturation of 20% or less prior to and during storage.

The present disclosure provides for, and includes, a method for reducing hemorrhagic shock in a trauma patient in need thereof comprising providing oxygen reduced blood having an oxygen saturation of 20% or less prior to and during storage, wherein the trauma patient comprises a lactate level of between 0.5 and 2.5 millimole per liter (mmol/L) prior to the providing, and wherein the hemorrhagic shock is reversed.

The present disclosure provides for, and includes, a method of reducing a liver injury in a trauma patient in need of transfusion therapy comprising providing oxygen reduced blood having an oxygen saturation of 20% or less prior to and during storage.

The present disclosure provides for, and includes, a method of reducing kidney failure in a hemorrhagic trauma patient in need of transfusion therapy comprising providing oxygen reduced blood having an oxygen saturation of 20% or less prior to and during storage.

The present disclosure provides for, and includes, a method of reducing lung injury in a hemorrhagic trauma patient in need of transfusion therapy comprising providing oxygen reduced blood having an oxygen saturation of 20% or less prior to and during storage.

BRIEF DESCRIPTION OF THE DRAWINGS

The present disclosure is provided with reference to the accompanying drawings, wherein.

Figure 1:
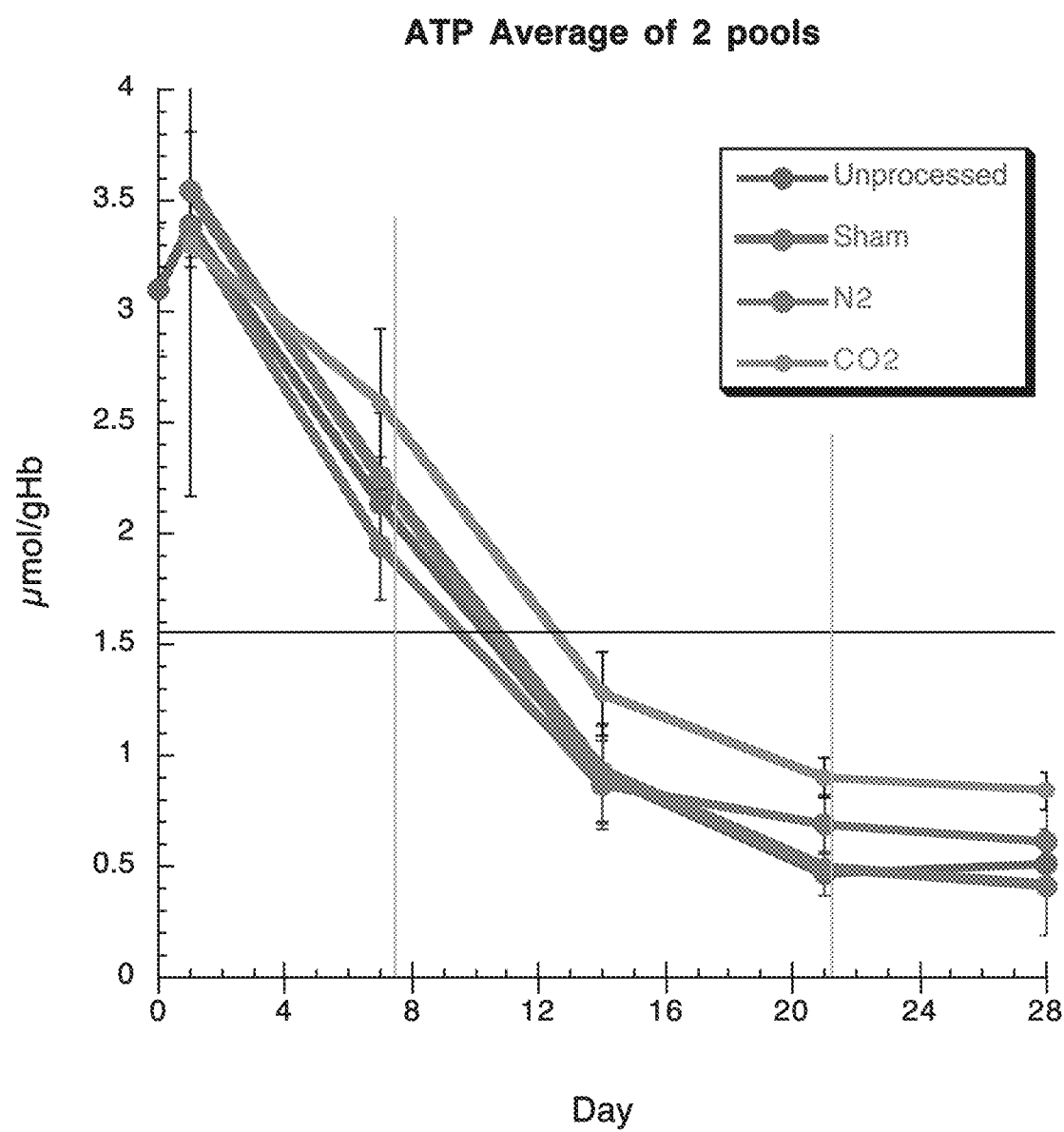
FIG. 1 is a graph presenting the results of an exemplary embodiment according to the present disclosure, comparing ATP levels in conventionally stored. RBCs (unprocessed; control), sham control (SC), oxygen reduced RBCs ($N_2$; OR), and oxygen and carbon dioxide reduced RBCS ($CO_2$; OCR).

The examples set out herein illustrate(s) several embodiment(s) of the present disclosure but should not be construed as limiting the scope of the present disclosure in any manner.

DETAILED DESCRIPTION

Methods of the present disclosure provide for, and include, providing a hemorrhagic trauma patient with oxygen reduced stored blood that has an oxygen saturation of 20% or less prior to and during storage. Methods also provide for providing a hemorrhagic trauma patient with oxygen reduced stored blood that has an oxygen saturation of between 15 and 20% prior to and during storage. Methods also provide for providing a hemorrhagic trauma patient with oxygen reduced stored blood that has an oxygen saturation of between 10 and 15% prior to and during storage. Methods also provide for providing a hemorrhagic trauma patient with oxygen reduced stored blood that has an oxygen saturation of between 5 and 10% prior to and during storage. Methods also provide for providing a hemorrhagic trauma patient with oxygen reduced stored blood that has an oxygen saturation of between 3 and 5% prior to and during storage.

Methods also provide for providing oxygen reduced stored blood that has an oxygen saturation of 20% or less prior to and during storage for transfusion to a person having hemorrhagic shock. Methods also provide for providing oxygen reduced stored blood that has an oxygen saturation of 20% or less prior to and during storage for transfusion to a person having hemorrhagic trauma. Also included are methods comprising transfusing oxygen reduced stored blood that has an oxygen saturation of 20% or less prior to and during storage to a patient having an increased risk of trauma due to surgery. Methods providing oxygen reduced stored blood having an initial oxygen saturation of 20% or less include providing oxygen reduced stored blood having an initial oxygen saturation of 10% or less. Methods of providing oxygen reduced stored blood having an initial oxygen saturation of 20% or less further include providing oxygen reduced stored blood having an initial oxygen saturation of 5% or less. Methods of providing oxygen reduced stored blood having an initial oxygen saturation of 20% or less further include providing oxygen reduced stored blood having an initial oxygen saturation of 3% or less.

Methods of the present disclosure provide for, and include, providing oxygen reduced stored blood for the treatment of trauma having an oxygen saturation of 20% or less prior to and during storage for a storage period of at least one week, at least two weeks, at least 3 weeks, at least 4 weeks, at least 5 weeks, or at least 6 weeks. Methods also provide for providing oxygen reduced stored blood for the treatment of trauma having an oxygen saturation of 15% or less after a storage period of at least one week, at least two weeks, at least 3 weeks, at least 4 weeks, at least 5 weeks, or at least 6 weeks. Methods also provide for providing oxygen reduced stored blood for the treatment of trauma having an oxygen saturation of 10% or less after a storage period of at least one week, at least two weeks, at least 3 weeks, at least 4 weeks, at least 5 weeks, or at least 6 weeks. Methods further provide for providing oxygen reduced stored blood for the treatment of trauma having an oxygen saturation of 5% or less after a storage period of at least one week, at least two weeks, at least 3 weeks, at least 4 weeks, at least 5 weeks, or at least 6 weeks. Methods further provide for providing oxygen reduced stored blood for the treatment of trauma having an oxygen saturation of 3% or less after a storage period of at least one week, at least two weeks, at least 3 weeks, at least 4 weeks, at least 5 weeks, or at least 6 weeks. Methods also provide for providing oxygen reduced stored blood for the treatment of trauma having an oxygen saturation of between 3 and 5% after a storage period of at least one week, at least two weeks, at least 3 weeks, at least 4 weeks, at least 5 weeks, or at least 6 weeks. Methods also provide for providing oxygen reduced stored blood for the treatment of trauma having an oxygen saturation of between 5 and 10% after a storage period of at least one week, at least two weeks, at least 3 weeks, at least 4 weeks, at least 5 weeks, or at least 6 weeks. Methods also provide for providing oxygen reduced stored blood for the treatment of trauma having an oxygen saturation of between 10 and 15% after a storage period of at least one week, at least two weeks, at least 3 weeks, at least 4 weeks, at least 5 weeks, or at least 6 weeks. Methods also provide for providing oxygen reduced stored blood for the treatment of trauma having an oxygen saturation of between 15 and 20% after a storage period of at least one week, at least two weeks, at least 3 weeks, at least 4 weeks, at least 5 weeks, or at least 6 weeks.

Methods of the present disclosure provide for, and include, providing a trauma patient with oxygen reduced stored blood that has an oxygen saturation of 20% or less prior to and during storage. In an aspect, a trauma patient suffers from a head trauma, a penetrating wound, blunt force trauma, injury due to a fall, or injury due to a car accident. In another aspect, a trauma patient is a hemorrhagic trauma patient. In yet another aspect, a trauma patient is hemorrhagic due to surgery, a penetrating wound, blunt force trauma, an injury due to a fail, or an injury due to a car accident.

In an aspect of the present disclosure, a trauma patient or hemorrhagic trauma patient is a subject in need of OR and OCR stored blood. In aspects of the present disclosure, a trauma patient is a hemorrhagic trauma patient in need of one or more units of blood as transfusion therapy. In aspects of the present disclosure, a trauma patient is a hemorrhagic trauma patient in need of two or more units of blood as transfusion therapy. In aspects of the present disclosure, a trauma patient is a hemorrhagic trauma patient in need of three or more units of blood as transfusion therapy.

In an aspect of the present disclosure, a trauma patient is a patient in hemorrhagic shock. In an aspect, a trauma patient is in hemorrhagic shock due to a head trauma, a penetrating wound, blunt force trauma, injury from a fall, or injury from a car accident. In aspects of the present disclosure, a hemorrhagic trauma patient is a patient with a class I hemorrhage. In another aspect, a hemorrhagic trauma patient is a patient with a class II hemorrhage. In another aspect, a hemorrhagic trauma patient is a patient with a class III hemorrhage. In another aspect, a hemorrhagic trauma patient is a patient with a class IV hemorrhage. In an aspect of the present disclosure, a hemorrhagic trauma patient loses up to 15% of blood volume. In another aspect, a hemorrhagic trauma patient loses between 15 and 30% of blood volume. In another aspect, a hemorrhagic trauma patient loses between 30 and 40% of blood volume. In a further, a hemorrhagic trauma patient loses greater than 40% of blood volume.

The present disclosure provides for, and includes, a patient in need of transfusion therapy with OR or OCR RBCs exhibits one or more signs selected from the group consisting of decreased mean arterial pressure, a decreased hematocrit, increased lactate, increased glucose, increased aspartate aminotransferase (AST), increased alanine aminotransferase (ALT), increased urine neutrophil gelatinase-associated lipocalin (u-NGAL), increased serum creatinine, and increased blood urea nitrogen. In an aspect of the present disclosure, a patient in need of transfusion therapy with OR or OCR RBCS is a hemorrhagic trauma patient having a decreased mean arterial pressure. The present disclosure provides for, and includes, a patient in need of transfusion therapy with OR or OCR RBCs exhibits increased aspartate aminotransferase (AST) and increased alanine aminotransferase (ALT). The present disclosure provides for, and includes, a patient in need of transfusion therapy with OR or OCR RBCs exhibits decreased mean arterial pressure and increased lactate. The present disclosure provides for, and includes, a patient in need of transfusion therapy with OR or OCR RBCs exhibits increased aspartate aminotransferase (AST), increased alanine aminotransferase (ALT), and increased blood urea nitrogen. The present disclosure provides for, and includes, a patient in need of transfusion therapy with OR or OCR RBCs exhibits increased aspartate aminotransferase (AST), increased alanine aminotransferase (ALT), increased serum creatinine, and increased blood urea nitrogen. The present disclosure provides for, and includes, a patient in need of transfusion therapy with OR or OCR RBCs exhibits increased lactate and increased glucose. The present disclosure provides for, and includes, a patient in need of transfusion therapy with OR or OCR RBCs exhibiting increased urine neutrophil gelatinase-associated lipocalin (u-NGAL), increased serum creatinine, and increased blood urea nitrogen.

In another aspect, a patient in need of transfusion therapy with OR or OCR RBCs is a hemorrhagic trauma patient having a decreased hematocrit. In another aspect, a patient in need of transfusion therapy with OR or OCR RBCs is a hemorrhagic trauma patient having increased lactate. In yet another aspect, a patient in need of transfusion therapy with OR or OCR RBCs is a hemorrhagic trauma patient having increased glucose. In a further aspect, a hemorrhagic trauma patient having increased in aspartate aminotransferase (AST). In another aspect, a patient in need of transfusion therapy with OR or OCR RBCs is a hemorrhagic trauma patient having increased alanine aminotransferase (ALT). In another aspect, a patient in need of transfusion therapy with OR or OCR RBCs is a hemorrhagic trauma patient having increased urine neutrophil gelatinase-associated lipocalin (u-NGAL). In another aspect, a patient in need of transfusion therapy with OR or OCR RBCs is a hemorrhagic trauma patient having increased serum creatinine. In another aspect, a patient in need of transfusion therapy with OR or OCR RBCs is a hemorrhagic trauma patient having increased blood urea nitrogen.

In an aspect of the present disclosure, the OR and OCR stored blood for use in transfusion therapy of a trauma patient in need thereof has an initial oxygen saturation of 20% or less. In another aspect, OR and OCR stored blood has an initial oxygen saturation of 10% or less. In another aspect, OR and OCR stored blood has an initial oxygen saturation of 5% or less. In another aspect, OR and OCR stored blood has an initial oxygen saturation of 3% or less.

In an aspect of the present disclosure, the OCR stored blood for use in transfusion therapy of a trauma patient in need thereof has an initial $pCO_2$ (at 37° C.) of between 10 and 40 mmHg. In another aspect, OCR stored blood has an initial $pCO_2$ of between 10 and 30 mmHg. In another aspect, OCR stored blood has an initial $pCO_2$ of between 10 and 20 mmHg. In another aspect, OCR stored blood has an initial $pCO_2$ of between 10 and 15 mmHg. In yet another aspect, OCR stored blood has an initial $pCO_2$ of less than 10 mmHg.

In an aspect of the present disclosure, OR and OCR stored blood for use in transfusion therapy of a trauma patient in need thereof has an initial oxygen saturation of 20% or less and is stored for less than 2 days. In an aspect, OR and OCR stored blood has an initial oxygen saturation of 20% or less is stored for less than 7 days. In another aspect, OR and OCR stored blood has an initial oxygen saturation of 20% or less is stored for less than 14 days. In another aspect, oxygen reduced stored blood has an initial oxygen saturation of 20% or less is stored for less than 21 days. In another aspect, oxygen reduced stored blood for use in transfusion therapy of a trauma patient in need thereof has an initial oxygen saturation of 20% or less is stored for less than 28 days. In another aspect, oxygen reduced stored blood has an initial oxygen saturation of 20% or less is stored for less than 35 days. In another aspect, oxygen reduced stored blood has an initial oxygen saturation of 20% or less is stored for less than 42 days. In another aspect, oxygen reduced stored blood has an initial oxygen saturation of 20% or less is stored for less than 45 days. In an aspect of the present disclosure, OR and OCR stored blood has an oxygen saturation of 20% or less during storage.

Suitable blood for use methods according to the present disclosure for use in transfusion therapy of a trauma patient in need thereof comprise oxygen reduced stored blood having an anticoagulant. In an aspect of the present disclosure, oxygen reduced red blood cells is stored for up to 3 weeks to produce oxygen reduced stored blood. In another aspect, oxygen reduced stored blood usually further comprise an additive solution. Suitable additive solutions according to the present disclosure include AS-1, AS-3 (Nutricel®), AS-5, SAGM, PAGG-SM, PAGG-GM, MAP, AS-7, ESOL-5, EAS61, OFAS1, OFAS3, and combinations thereof. In an aspect, the additive solution is added at the time of component separation. In an aspect, the additive solution is AS-1. In another aspect, the additive solution is AS-3. In other aspects, the additive solution is SAGM.

Methods of the present disclosure provide for, and include, increasing the mean arterial pressure (MAP) in a hemorrhagic trauma patient in need of transfusion therapy comprising providing a trauma patient with oxygen reduced stored blood that has an oxygen saturation of 20% or less prior to and during storage. In an aspect, the mean arterial pressure is increased by between 20 and 60%. In another aspect, the mean arterial pressure is increased by between 30 and 60%. In another aspect, the mean arterial pressure of a trauma patient receiving transfusion therapy of OR or OCR blood is increased by between 30 and 50%. In yet another aspect, the mean arterial pressure is increased by between 30 and 60%. In a further aspect, the mean arterial pressure of a trauma patient receiving transfusion therapy of OR or OCR blood is increased by between 30 and 40%. In an aspect, the mean arterial pressure is increased by at least 10, 20, 30, 40, 50, 60, 70, 80, or 90% more than the mean arterial pressure of a patient transfused with conventionally stored blood.

In an aspect of the present disclosure, the mean arterial pressure is increased by at least 1.5 fold. In another aspect, the mean arterial pressure of a trauma patient receiving transfusion therapy of OR or OCR blood is increased by at least 2 fold. In a further aspect, the mean arterial pressure is increased by between 1 and 2 fold. In an aspect of the present disclosure, the mean arterial pressure of a trauma patient receiving transfusion therapy of OR or OCR blood is increased by at least 10 mmHg, at least 20 mmHg, at least 30 mmHg, at least 40 mmHg, at least 50 mmHg, or at least 60 mmHg. In another aspect, the mean arterial pressure of a trauma patient receiving transfusion therapy of OR or OCR blood is increased by between 20 and 50 mmHg. In a further aspect, the mean arterial pressure is increased by between 30 and 50 mmHg.

Methods of the present disclosure provide for, and include, increasing the mean arterial pressure in a trauma patient in need of transfusion therapy to between 70 and 110 mmHg comprising providing a trauma patient with oxygen reduced stored blood that has an oxygen saturation of 20% or less prior to, and during storage. In another aspect, the mean arterial pressure of a trauma patient receiving transfusion therapy of OR or OCR blood is increased to at least 70 mmHg. In another aspect, the mean arterial pressure of a trauma patient receiving transfusion therapy of OR or OCR blood is increased to at least 80 mmHg. In yet another aspect, the mean arterial pressure is increased to at least 90 mmHg. In a further aspect, the mean arterial pressure is increased to at least 100 mmHg. In an aspect of the present disclosure, the mean arterial pressure in a subject in need thereof remains between 70 and 110 mmHg for at least 1 hour after transfusion. In another aspect, the mean arterial pressure remains between 70 and 110 mmHg for at least 2 hours after transfusion. In yet another aspect, the mean arterial pressure remains between 70 and 105 mmHg for at least 3 hours after transfusion. In another aspect, the mean arterial pressure remains between 70 and 110 mmHg for at least 4 hours after transfusion. In another aspect, the mean arterial pressure remains between 70 and 110 mmHg for at least 5 hours after transfusion.

Methods of the present disclosure provide for, and include, increasing the mean arterial pressure in a trauma patient in need of transfusion therapy at a rate faster than the mean arterial pressure of a patient transfused with conventionally stored blood comprising providing a trauma patient with oxygen reduced stored blood that has an oxygen saturation of 20% or less prior to and during storage. In an aspect, the mean arterial pressure of a patient transfused with OR or OCR blood is restored to within normal physiologic parameters in half the time when compared to conventionally stored blood.

Methods of the present disclosure provide for, and include, reducing the amount of stored blood needed for transfusion in a hemorrhagic trauma patient in need of transfusion therapy comprising providing a trauma patient with oxygen reduced stored blood that has an oxygen saturation of 20% or less prior to and during storage. In an aspect, the amount of OR stored blood needed for transfusion is between 10 and 90% less than the amount of conventionally stared blood needed. In another aspect, the amount of OR stored blood needed for transfusion is between 10 and 30% less than the amount of conventionally stored blood needed. In another aspect, the amount of OR stored blood needed for transfusion is between 20 and 50% less than the amount of conventionally stored blood needed. In another aspect, the amount of OR stored blood needed for transfusion is between 20 and 80% less than the amount of conventionally stored blood needed. In another aspect, the amount of OR stored blood needed for transfusion is between 30 and 80% less than the amount of conventionally stored blood needed. In yet another aspect, the amount of OR stored blood needed for transfusion is between 40 and 85% less than the amount of conventionally stored blood needed. In a further aspect, the amount of OR stored blood needed for transfusion is between 50 and 90% less than the amount of conventionally stored blood needed.

Methods of the present disclosure provide for, and include, reducing the amount of stored blood needed for transfusion in a hemorrhagic trauma patient in need of transfusion therapy by at least 10% less comprising providing a trauma patient with oxygen reduced stored blood that has an oxygen saturation of 20% or less prior to and during storage. In an aspect, the amount of OR stored blood needed for transfusion is at least 20% less than the amount of conventionally stored blood needed. In another aspect, the amount of OR stored blood needed for transfusion is at least 30% less than the amount of conventionally stored blood needed. In another aspect, the amount of OR stored blood needed for transfusion is at least 40% less than the amount of conventionally stored blood needed. In another aspect, the amount of OR stored blood needed for transfusion is at least 50% less than the amount of conventionally stored blood needed. In yet another aspect, the amount of OR stored blood needed for transfusion is at least 60% less than the amount of conventionally stored blood needed. In another aspect, the amount of OR stored blood needed for transfusion is at least 70% less than the amount of conventionally stored blood needed. In a further aspect, the amount of OR stored blood needed for transfusion is between about 10 and 20%, about 20 and 30%, about 30 and 40%, about 40 and 50%, about 50 and 60%, about 60 and 70%, about 70 and 80%, about 80 and 90%, or about 90 and 95% less than the amount of conventionally stored blood needed. In another aspect, the amount of OR stored blood needed for transfusion in a trauma patient in need of transfusion therapy is between 10 and 20%, 20 and 30%, 30 and 40%, 40 and 50%, 50 and 60%, 60 and 70%, 70 and 80%, 80 and 90%, or 90 and 95% less than the amount of conventionally stored blood needed.

Figure 7A:
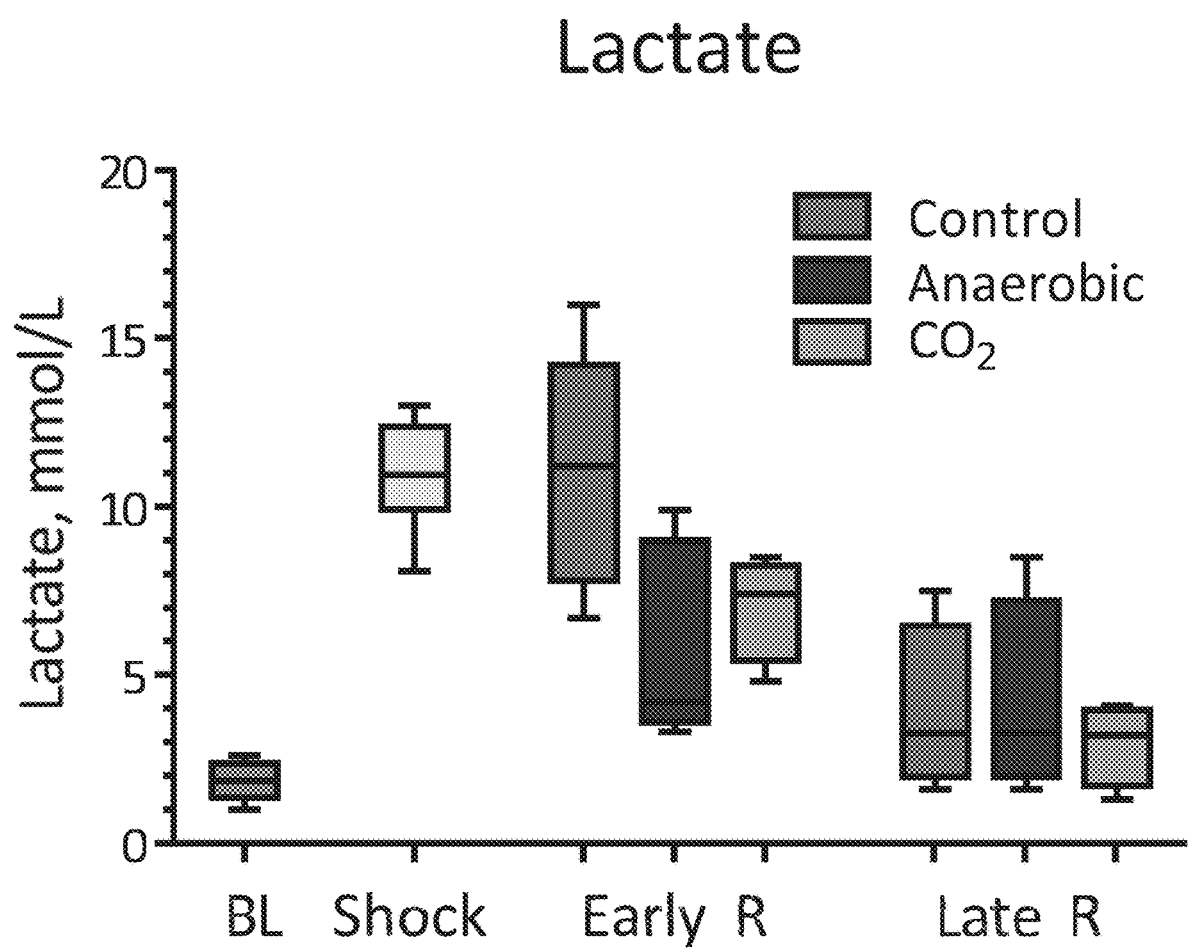
FIGS. 7A and 7B are graphs presenting the results of an exemplary embodiment according to the present disclosure, providing a comparison of the amount of lactate in animals resuscitated with control, OR-RBCS, and OCR-RBCS stored for 1 week (FIG. 7A) or 3 weeks (FIG. 7B). BL (baseline) identifies animals not under shock conditions. Shock identifies animals under hemorrhagic shock. Early R identifies a resuscitation period of 10 mins. Late R identifies a resuscitation period of 60 mins.
Figure 7B:
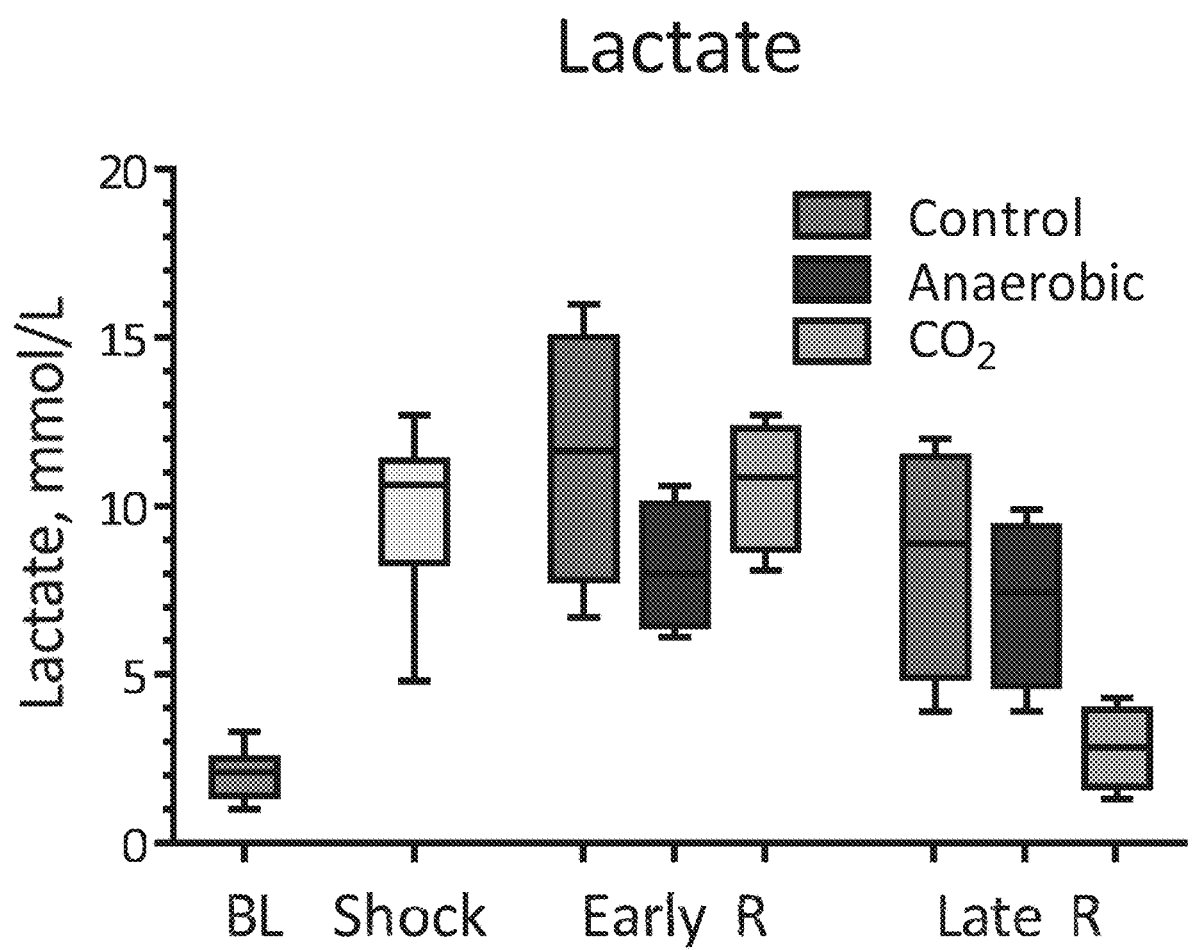

Lactate clearance is a biomarker for resuscitation from hemorrhagic shock. See Hashmi et al., "Predictors of mortality in geriatric trauma patients: a systematic review and meta-analysis," *The journal of trauma and acute care surgery,* 76:894-901 (2014); Regnier et al., "Prognostic significance of blood lactate and lactate clearance in trauma patients," *Anesthesiology,* 117:1276-88 (2012), and Zhang et al., "Lactate clearance is a useful biomarker for the prediction of all-cause mortality in critically ill patients: a systematic review and meta-analysis," *Critical care medicine,* 42:2118-25 (2014) ("Zhang 2014") (hereby incorporated by reference in their entireties). The clinical value of lactate clearance is useful in predicting the outcome of patients with septic shock and critically ill patients without evident circulatory shock. Elevated lactate is an indicator of adverse clinical outcome, and its rapid clearance is universally associated with improved outcome in heterogeneous ICU or ED patient population. See Zhang 2014. Decreased lactate levels in animals resuscitated with OR-RBCs compared to conventionally RBCs support the notion that resuscitation with OR RBCs can significantly improve patients' clinical outcome. See FIGS. 7A and 7B.

Methods of the present disclosure provide for, and include, reducing the lactate level in a trauma patient in need of transfusion therapy comprising providing a trauma patient with oxygen reduced (OR) stored blood that has an oxygen saturation of 20% or less prior to and during storage. In an aspect, the lactate level is reduced by between 10 and 90%. In an aspect, transfusion with OR stored blood reduces the lactate level in a trauma patient in need of transfusion therapy by between 10 and 50%. In another aspect, transfusion with OR stored blood reduces the lactate level in a trauma patient in need of transfusion therapy by between 20 and 40%. In another aspect, transfusion with OR stored blood reduces the lactate level in a trauma patient in need of transfusion therapy by between 50 and 90%. In yet another aspect, transfusion with OR stored blood reduces the lactate level in a trauma patient in need of transfusion therapy by between 60 and 90%. In another aspect, transfusion with OR stored blood reduces the lactate level in a trauma patient in need of transfusion therapy by between 10 and 20%, 20 and 30%, 30 and 40%, 40 and 50%, 50 and 60%, 60 and 70%, 70 and 80%, or 80 and 90%. In another aspect, transfusion with OR stored blood reduces the lactate level in a trauma patient in need of transfusion therapy by at least 10%. In another aspect, transfusion with OR stored blood reduces the lactate level in a trauma patient in need of transfusion therapy by at least 20%. In a further aspect, transfusion with OR stored blood reduces the lactate level in a trauma patient in need of transfusion therapy by at least 30, at least 40, at least 50, at least 60, at least 70, at least 80, or at least 90%.

Methods of the present disclosure provide for, and include, reducing elevated lactate levels in a trauma patient in need of transfusion therapy to between about 0.5 and about 2.5 mmol/L comprising providing a trauma patient with oxygen reduced stored blood that has an oxygen saturation of 20% or less prior to and during storage. In an aspect, the lactate level in a trauma patient in need of transfusion therapy is reduced to between about 0.9 and about 2 mmol/L. In an aspect, the lactate level in a trauma patient in need of transfusion therapy is reduced to between about 0.9 and about 1.7 mmol/L. In another aspect, the lactate level in a patient in need of transfusion therapy is reduced to between about 1.4 and about 2.4 mmol/L. In another aspect, the lactate level in a trauma patient in need of transfusion therapy is reduced to between about 1.7 and about 2.5 mmol/L. In yet another aspect, the lactate level in a trauma patient in need of transfusion therapy is reduced to less than about 2.5 mmol/L. In a further aspect, the lactate level in a trauma patient in need of transfusion therapy is reduced to less than about 2.0 mmol/L. In another aspect, the lactate level in a trauma patient in need of transfusion therapy is reduced to less than about 1.5 mmol/L. In another aspect, the lactate level in a trauma patient in need of transfusion therapy is reduced to less than about 1.0 mmol/L. In yet another aspect, the lactate level in a trauma patient in need of transfusion therapy is reduced to between about 0.5 and about 1.0 mmol/L.

Methods of the present disclosure provide for, and include, reducing elevated lactate levels in a trauma patient in need of transfusion therapy to between 0.5 and 2.5 mmol/L comprising providing a trauma patient with oxygen reduced stored blood that has an oxygen saturation of 20% or less prior to and during storage. In an aspect, the lactate level in a patient in need of transfusion therapy is reduced to between 0.9 and 2 mmol/L. In an aspect, the lactate level in a trauma patient in need of transfusion therapy is reduced to between 0.9 and 1.7 mmol/L. In another aspect, the lactate level in a trauma patient in need of transfusion therapy is reduced to between 1.4 and 2.4 mmol/L. In another aspect, the lactate level in a trauma patient in need of transfusion therapy is reduced to between 1.7 and 2.5 mmol/L. In another aspect, the lactate level in a trauma patient in need of transfusion therapy is reduced to between 0.5 and 1 mmol/L.

Methods of the present disclosure provide for, and include, reducing elevated lactate levels in a hemorrhagic trauma patient in need of transfusion therapy to less than 4 mmol/L comprising providing a trauma patient with oxygen reduced stored blood that has an oxygen saturation of 20% or less prior to and during storage. In an aspect, the lactate level in a trauma patient in need of transfusion therapy is reduced to less than 3 mmol/L. In yet another aspect, the lactate level in a trauma patient in need of transfusion therapy is reduced to less than 2.5 mmol/L. In another aspect, the lactate level in a patient is reduced to less than 2.3 mmol/L. In another aspect, the lactate level in a trauma patient in need of transfusion therapy is reduced to less than 2 mmol/L. In another aspect, the lactate level in a trauma patient in need of transfusion therapy is reduced to less than 2 mmol/L. In another aspect, the lactate level in a trauma patient in need of transfusion therapy is reduced to less than 1.5 mmol/L. In another aspect, the lactate level in a trauma patient in need of transfusion therapy is reduced to less than 1 mmol/L.

Figure 8A:
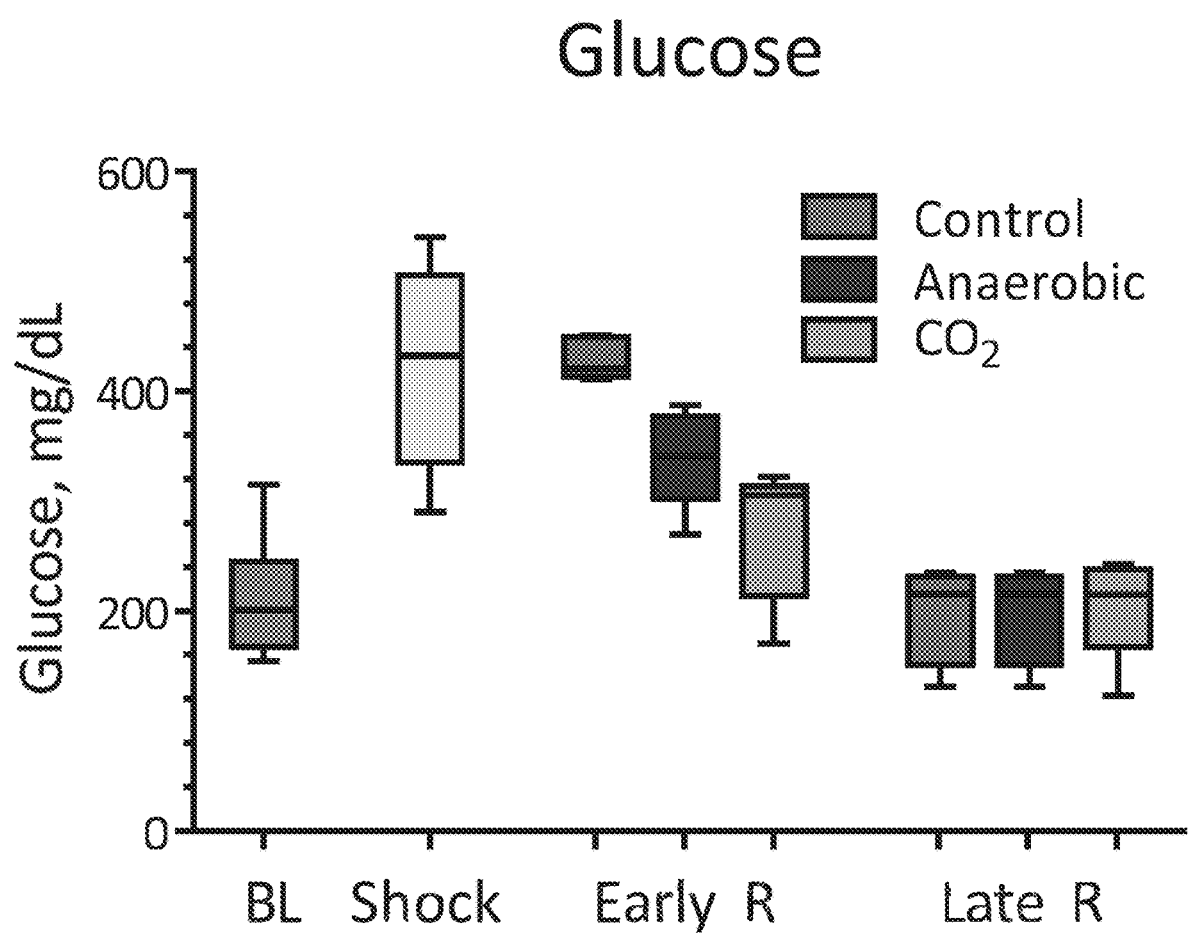
FIGS. 8A and 8B are graphs presenting the results of an exemplary embodiment according to the present disclosure, providing a comparison of the amount of glucose in animals resuscitated with control, OR-RBCS, and OCR-RBCs stored for 1 week (FIG. 8A) or 3 weeks (FIG. 8B). BL (baseline) identifies animals not under shock conditions. Shock identifies animals under hemorrhagic shock. Early R identifies a resuscitation period of 10 mins. Late R identifies a resuscitation period of 60 mins.

Blood glucose level is also known to be a predictor for outcome in several disease patterns and particularly in trauma patients. Trauma patients are more prone to poor outcome due to hyperglycemia than other critically ill patients. See Kreutziger et al., "Admission blood glucose predicted hemorrhagic shock in multiple trauma patients," *Injury*, 46:15-20 (2015) (hereby incorporated by reference in its entirety). Studies evaluating the relationship of early hyperglycemia and trauma patients examined early hyperglycemia at three possible cutoffs: glucose≥110 mg/dL, glucose≥150 mg/dL, and glucose≥200 mg/dL. See Laird et al., "Relationship of early hyperglycemia to mortality in trauma patients," *J Trauma*, 56:1058-62 (2004) (hereby incorporated by reference in its entirety). A glucose level ≥200 mg/dL, is associated with significantly higher infection and mortality rates in trauma patients independent of injury characteristics. This was not true at the cutoffs of ≥110 mg/dL or ≥150 mg/dL. Decreased glucose levels in animals resuscitated with OR- and OCR-RBCs compared to conventionally RBCs support the notion that resuscitation with OR-RBCs can significantly improve patients' clinical outcome. See FIGS. 8A and 8B.

Methods of the present disclosure provide for, and include, reducing glucose in a trauma patient in need of transfusion therapy comprising providing a trauma patient with oxygen reduced (OR) stored blood that has an oxygen saturation of 20% or less prior to and during storage. In an aspect, glucose is reduced by between 10 and 90% as compared to transfusion of blood stored under conventional conditions. In an aspect, transfusion with OR stored blood reduces glucose by between 10 and 50% as compared to transfusion of blood stored under conventional conditions. In another aspect, transfusion with OR stored blood reduces glucose by between 20 and 40% as compared to transfusion of blood stored under conventional conditions. In another aspect, transfusion with OR stored blood reduces glucose by between 50 and 90% as compared to transfusion of blood stored under conventional conditions. In yet another aspect, transfusion with OR stored blood reduces glucose by between 60 and 90%. In another aspect, transfusion with OR stored blood reduces glucose by between 10 and 20%, 20 and 30%, 30 and 40%, 40 and 50%, 50 and 60%, 60 and 70%, 70 and 80% or 80 and 90% as compared to transfusion of blood stored under conventional conditions. In another aspect, transfusion with OR stored blood reduces glucose by at least 10% as compared to transfusion of blood stored under conventional conditions. In another aspect, transfusion with OR stored blood reduces glucose by at least 20%. In a further aspect, transfusion with OR stored blood reduces glucose by at least 30, at least 40, at least 50, at least 60, at least 70, at least 80, or at least 90%.

Methods of the present disclosure provide for, and include, reducing glucose levels in a trauma patient in need of transfusion therapy to between about 70 and about 120 mg/dL comprising providing a trauma patient with oxygen reduced stored blood that has an oxygen saturation of 20% or less prior to and during storage. In an aspect, glucose in a patient after transfusion therapy with OR or OCR blood is between about 70 and about 110 mg/dL. In another aspect, glucose in a patient after transfusion therapy with OR or OCR blood is between about 70 and about 100 mg/dL. In another aspect, glucose in a trauma patient after transfusion therapy with OR or OCR blood is between about 90 and about 120 mg/dL. In another aspect, glucose in a trauma patient after transfusion therapy with OR or OCR blood is between about 90 and about 100 mg/dL.

Methods of the present disclosure provide for, and include, reducing glucose levels in a trauma patient in need of transfusion therapy to between 70 and 120 mg/dL comprising providing a trauma patient with oxygen reduced stored blood that has an oxygen saturation of 20% or less prior to and during storage. In an aspect, glucose in a patient after transfusion therapy with OR or OCR blood is between 70 and 110 mg/dL. In another aspect, glucose in a patient is between 70 and 100 mg/dL. In another aspect, glucose in a patient is between 90 and 120 mg/dL. In another aspect, glucose in a patient after transfusion therapy with OR or OCR blood is between 90 and 100 mg/dL.

Methods of the present disclosure provide for, and include, reducing glucose levels in a trauma patient in need of transfusion therapy to less than 120 mg/dL comprising providing a trauma patient with oxygen reduced stored blood that has an oxygen saturation of 20% or less prior to and during storage. In a further aspect, glucose in a patient after transfusion therapy with OR or OCR blood is less than 110 mmol/L. In yet another aspect, glucose in a patient after transfusion therapy with OR or OCR blood is less than 100 mg/dL. In another aspect, glucose in a patient after transfusion therapy with OR or OCR blood is less than 200 mg/dL. In another aspect, glucose in a patient after transfusion therapy with OR or OCR blood is less than 90 mg/dL. In another aspect, glucose in a patient after transfusion therapy with OR or OCR blood is less than 80 mg/dL.

In an aspect of the present disclosure, a trauma patient is at increased risk of complications from transfusion therapies based on a pre-existing or underlying condition. In an aspect, a trauma patient has a pre-existing or underlying condition selected from the group consisting of a diabetes, ischemic heart disease, systemic inflammatory syndrome brought on by trauma or infection, multiple organ failure brought on by trauma or infection, smoke inhalation, chronic pulmonary obstructive disease such as systemic inflammation due to infection, a coagulopathy disorder, and autoimmune diseases. In another aspect, a trauma patient has one or more pre-existing or underlying conditions selected from the group consisting of a diabetes, ischemic heart disease, systemic inflammatory syndrome brought on by trauma or infection, multiple organ failure brought on by trauma or infection, smoke inhalation, and chronic pulmonary obstructive disease such as systemic inflammation due to infection, a coagulopathy disorder, and autoimmune diseases. In another aspect, a trauma patient has two or more pre-existing or underlying conditions selected from the group consisting of a diabetes, ischemic heart disease, systemic inflammatory syndrome brought on by trauma or infection, multiple organ failure brought on by trauma or infection, smoke inhalation, chronic pulmonary obstructive disease such as systemic inflammation due to infection, a coagulopathy disorder, and autoimmune diseases. In another aspect, a trauma patient has three or more pre-existing or underlying conditions selected from the group consisting of a diabetes, ischemic heart disease, systemic inflammatory syndrome brought on by trauma or infection, multiple organ failure brought on by trauma or infection, smoke inhalation, chronic pulmonary obstructive disease such as systemic inflammation due to infection, a coagulopathy disorder, and autoimmune diseases.

During hemorrhagic shock, patients experience an adverse event including liver damage or failure, kidney damage or failure, lung damage or failure, or a combination thereof. The present disclosure provides for, and includes, a patient in need of transfusion therapy with OR or OCR RBCs exhibits one or more adverse event selected from the group consisting of liver damage or failure, kidney damage or failure, or lung damage or failure. The present disclosure provides for, and includes, a patient in need of transfusion therapy with OR or OCR RBCs exhibits two or more adverse event selected from the group consisting of liver damage or failure, kidney damage or failure, or lung damage or failure.

Methods of the present disclosure provide for, and include, reducing an adverse event in a trauma patient comprising providing a trauma patient in need of transfusion therapy with oxygen reduced stored blood that has an oxygen saturation of 20% or less prior to and during storage. In an aspect, the adverse event after transfusion therapy with OR or OCR blood is reduced by at least 5%. In another aspect, the adverse event after transfusion therapy with OR or OCR blood is reduced by at least 10%. In another aspect, the adverse event after transfusion therapy with OR or OCR blood is reduced by at least 20%. In another aspect, the adverse event after transfusion therapy with OR or OCR blood is reduced by at least 30%. In another aspect, the adverse event after transfusion therapy with OR or OCR blood is reduced by at least 40%. In another aspect, the adverse event after transfusion therapy with OR or OCR blood is reduced by at least 50%. In another aspect, the adverse event after transfusion therapy with OR or OCR blood is reduced by at least 60%. In another aspect, the adverse event is reduced by at least 70%. In another aspect, the adverse event after transfusion therapy with OR or OCR blood is reduced by at least 80%. In another aspect, the adverse event is reduced by at least 90%. In a further aspect, the adverse event after transfusion therapy with OR or OCR blood is reduced by between 1 and 10%, 10 and 20%, 20 and 30%, 30 and 40%, 40 and 50%, 50 and 60%, 60 and 70%, 70 and 80%, 80 and 90%, or 90 and 95%. In an aspect, the adverse event after transfusion therapy with OR or OCR blood is liver injury or damage. In another aspect, the adverse event is lung injury or damage. In yet another aspect, the adverse event is kidney injury or damage. In a further aspect, an adverse event is liver injury, lung injury, kidney injury, or a combination thereof.

Elevated levels of liver enzymes, including, but not limited to aspartate aminotransferase (AST) and alanine aminotransferase (ALT), signify some form of liver damage, shock, or injury. Methods of the present disclosure provide for, and include, reducing elevated levels of liver enzymes in a trauma patient comprising providing a trauma patient with oxygen reduced stored blood that has an oxygen saturation of 20% or less prior to and during storage.

Methods of the present disclosure provide for, and include, reducing AST levels in a trauma patient in need of transfusion therapy comprising providing a trauma patient with oxygen reduced stored blood that has an oxygen saturation of 20% or less prior to and during storage. In an aspect, the AST level is reduced by at least 5% relative to the AST level of a patient transfused with conventionally stored blood. In another aspect, the AST level is reduced by at least 10% relative to the AST level of a patient transfused with conventionally stored blood. In another aspect, the AST level is reduced by at least 20% relative to the AST level of a patient transfused with conventionally stored blood. In another aspect, the AST level is reduced by at least 30% relative to the AST level of a patient transfused with conventionally stored blood. In another aspect, the AST level is reduced by at least 40%. In another aspect, the AST level is reduced by at least 50% relative to the AST level of a patient transfused with conventionally stored blood. In another aspect, the AST level is reduced by at least 60%. In another aspect, the AST level is reduced by at least 70% relative to the AST level of a patient transfused with conventionally stored blood. In yet another aspect, the AST level is reduced by at least 80%. In a further aspect, the AST level is reduced by at least 90% relative to the AST level of a patient transfused with conventionally stored blood. In a further aspect, the AST level is reduced by between 1 and 10%, 10 and 20%, 20 and 30%, 30 and 40%, 40 and 50%, 50 and 60%, 60 and 70%, 70 and 80%, 80 and 90%, or 90 and 95% relative to the AST level of a patient transfused with conventionally stored blood.

Methods of the present disclosure provide for, and include, reducing AST levels in a trauma patient in need of transfusion therapy by between 1.5 and 10 fold comprising providing a trauma patient with oxygen reduced stored blood that has an oxygen saturation of 20% or less prior to and during storage. In an aspect, the AST level is reduced by between 2 and 3 fold relative to the AST level of a patient transfused with conventionally stored blood. In another aspect, the AST level is reduced by between 3 and 4 fold. In another aspect, the AST level is reduced by between 4 and 10 fold. In another aspect, the AST level is reduced by between 6 and 9 fold relative to the AST level of a patient transfused with conventionally stored blood. In a further aspect, the AST level is reduced by between 2 and 5 fold. In another aspect, the AST level is reduced by between 10 and 50 fold relative to the AST level of a patient transfused with conventionally stored blood.

Methods of the present disclosure provide for, and include, reducing AST levels in a trauma patient in need of transfusion therapy by at least 1.5 fold comprising providing a trauma patient with oxygen reduced stored blood that has an oxygen saturation of 20% or less prior to and during storage. In an aspect, the AST level is reduced by at least 2 fold relative to the AST level of a patient transfused with conventionally stored blood. In another aspect, the AST level is reduced by at least 3 fold relative to the AST level of a patient transfused with conventionally stored blood. In another aspect, the AST level is reduced by at least 4 fold relative to the AST level of a patient transfused with conventionally stored blood. In another aspect, the AST level is reduced by at least 5 fold relative to the AST level of a patient transfused with conventionally stored blood. In a further aspect, the AST level is reduced by at least 6 fold. In another aspect, the AST level is reduced by at least 7 fold relative to the AST level of a patient transfused with conventionally stored blood. In another aspect, the AST level is reduced by at least 8 fold. In another aspect, the AST level is reduced by at least 9 fold relative to the AST level of a patient transfused with conventionally stored blood. In another aspect, the AST level is reduced by at least 10 fold relative to the AST level of a patient transfused with conventionally stored blood. In a further aspect, the AST level is reduced by at least 50 fold relative to the AST level of a patient transfused with conventionally stored blood.

Methods of the present disclosure provide for, and include, reducing ALT levels in a trauma patient in need of transfusion therapy comprising providing a trauma patient with oxygen reduced stored blood that has an oxygen saturation of 20% or less prior to and during storage. In an aspect, the ALT level is reduced by at least 5% relative to the ALT level of a patient transfused with conventionally stored blood. In another aspect, the ALT level is reduced by at least 10% relative to the ALT level of a patient transfused with conventionally stored blood. In another aspect, the ALT level is reduced by at least 20% relative to the ALT level of a patient transfused with conventionally stored blood. In another aspect, the ALT level is reduced by at least 30% relative to the ALT level of a patient transfused with conventionally stored blood. In another aspect, the ALT level is reduced by at least 40% relative to the AS ALT T level of a patient transfused with conventionally stored blood. In another aspect, the ALT level is reduced by at least 50% relative to the ALT level of a patient transfused with conventionally stored blood. In another aspect, the ALT level is reduced by at least 60% relative to the ALT level of a patient transfused with conventionally stored blood. In another aspect, the ALT level is reduced by at least 70% relative to the ALT level of a patient transfused with conventionally stored blood. In yet another aspect, the ALT level is reduced by at least 80% relative to the ALT level of a patient transfused with conventionally stored blood. In a further aspect, the ALT level is reduced by at least 90%. In a further aspect, the ALT level is reduced by between 1 and 10%, 10 and 20%, 20 and 30%, 30 and 40%, 40 and 50%, 50 and 60%, 60 and 70%, 70 and 80%, 80 and 90%, or 90 and 95% relative to the ALT level of a patient transfused with conventionally stored blood.

Methods of the present disclosure provide for, and include, reducing ALT levels in a trauma patient in need of transfusion therapy by between 1.5 and 10 fold comprising providing a trauma patient with oxygen reduced stored blood that has an oxygen saturation of 20% or less prior to and during storage. In an aspect, the ALT level is reduced by between 2 and 3 fold relative to the ALT level of a patient transfused with conventionally stored blood. In another aspect, the ALT level is reduced by between 3 and 4 fold relative to the ALT level of a patient transfused with conventionally stored blood. In another aspect, the ALT level is reduced by between 4 and 10 fold relative to the ALT level of a patient transfused with conventionally stored blood. In another aspect, the ALT level is reduced by between 6 and 9 fold relative to the ALT level of a patient transfused with conventionally stored blood. In a further aspect, the ALT level is reduced by between 2 and 5 fold. In another aspect, the ALT level is reduced by between 10 and 50 fold relative to the ALT level of a patient transfused with conventionally stored blood.

Methods of the present disclosure provide for, and include, reducing ALT levels in a trauma patient in need of transfusion therapy by at least 1.5 fold comprising providing a trauma patient with oxygen reduced stored blood that has an oxygen saturation of 20% or less prior to and during storage. In an aspect, the ALT level is reduced by at least 2 fold relative to the ALT level of a patient transfused with conventionally stored blood. In another aspect, the ALT level is reduced by at least 3 fold relative to the ALT level of a patient transfused with conventionally stored blood. In another aspect, the ALT level is reduced by at least 4 fold relative to the ALT level of a patient transfused with conventionally stored blood. In another aspect, the ALT level is reduced by at least 5 fold relative to the ALT level of a patient transfused with conventionally stored blood. In a farther aspect, the ALT level is reduced by at least 6 fold relative to the ALT level of a patient transfused with conventionally stored blood. In another aspect, the ALT level is reduced by at least 7 fold relative to the ALT level of a patient transfused with conventionally stored blood. In another aspect, the ALT level is reduced by at least 8 fold relative to the ALT level of a patient transfused with conventionally stored blood. In another aspect, the ALT level is reduced by at least 9 fold relative to the ALT level of a patient transfused with conventionally stored blood. In another aspect, the ALT level is reduced by at least 10 fold relative to the ALT level of a patient transfused with conventionally stored blood. In a further aspect, the ALT level is reduced by at least 50 fold relative to the ALT level of a patient transfused with conventionally stored blood.

Markers of kidney function during and after hemorrhagic trauma include urine neutrophil gelatinase-associated lipocalin (u-NGAL), serum creatinine, and blood urea nitrogen (BUN). See Treeprasertsuk et al., "Urine neutrophil gelatinase-associated lipocalin: a diagnostic and prognostic marker for acute kidney injury (AKI) in hospitalized cirrhotic patients with AKI-prone conditions," BMC Gastroenterol 15:140 (2015) (hereby incorporated by reference in its entirety). Gene expression analyses reported in greater than 150 distinct studies performed in AKI models from several species ranging from rodents to humans have consistently revealed the NGAL gene to be one of the most dramatically upregulated genes in the kidney soon after an ischemic or a nephrotoxic insult. See Ciccia et al., "Pediatric acute kidney injury: prevalence, impact and management challenges," *Int J Nephrol Renovasc Dis*, 10:77-84 (2017) (hereby incorporated by reference in its entirety). Similarly serum creatinine levels can vary depending on age, race and body size, however, rising creatinine levels are indicative of kidney damage. Creatinine levels of greater than 1.2 for women and greater than 1.4 for men may be an early sign of kidney damage. Increased blood urea nitrogen (BUN) is seen associated with kidney disease or failure, as well as, congestive heart failure, shock and bleeding in the digestive tract. If the BUN level is higher than 100 mg/dL it points to severe kidney damage. Decreased levels of BUN are also a concern and can point to fluid excess, trauma, surgery, opioids, malnutrition, and anabolic steroid use. See Pagana, "Mosby's Manual of Diagnostic and Laboratory Tests," St, Louis Mosby, Inc., (1998) and Gowda, et al., "Markers of renal function tests," *N Am J Med Sci.* 2(4): 170-173(2010) (hereby incorporated by reference in their entireties). Decreased u-NGAL (FIGS. 16A and 16B) serum creatinine (FIGS. 11A and 11B), and BUN (FIGS. 12A and 12B) levels in animals resuscitated with OR- and OCR-RBCs compared to conventionally RBCs, as provided by the present disclosure, show that resuscitation with OR-RBCs can significantly improve patients' clinical outcome.

Methods of the present disclosure provide for, and include, reducing urinary neutrophil gelatinase-associated lipocalin (u-NGAL) levels in a trauma patient in need of transfusion therapy comprising providing a trauma patient with oxygen reduced stored blood that has an oxygen saturation of 20% or less prior to and during storage. In an aspect, the u-NGAL level is reduced by at least 5% relative to the u-NGAL level of a patient transfused with conventionally stored blood. In another aspect, the u-NGAL level is reduced by at least 10% relative to the u-NGAL, level of a patient transfused with conventionally stored blood. In another aspect, the u-NGAL level is reduced by at least 20% relative to the u-NGAL level of a patient transfused with conventionally stored blood. In another aspect, the u-NGAL level is reduced by at least 30%. In another aspect, the u-NGAL level is reduced by at least 40% relative to the u-NGAL level of a patient transfused with conventionally stored blood. In another aspect, the u-NGAL level is reduced by at least 50% relative to the u-NGAL level of a patient transfused with conventionally stored blood. In another aspect, the u-NGAL level is reduced by at least 60% relative to the u-NGAL level of a patient transfused with conventionally stored blood. In another aspect, the u-NGAL level is reduced by at least 70% relative to the u-NGAL level of a patient transfused with conventionally stored blood. In yet another aspect, the u-NGAL level is reduced by at least 80% relative to the u-NGAL level of a patient transfused with conventionally stored blood. In a further aspect, the u-NGAL level is reduced by at least 90% relative to the u-NGAL level of a patient transfused with conventionally stored blood. In a further aspect, the u-NGAL level is reduced by between 1 and 10%, 10 and 20%, 20 and 30%, 30 and 40%, 40 and 50%, 50 and 60%, 60 and 70%, 70 and 80%, 80 and 90%, or 90 and 95% relative to the u-NGAL level of a patient transfused with conventionally stored blood.

Methods of the present disclosure provide for, and include, reducing urinary neutrophil gelatinase-associated lipocalin (u-NGAL) levels in a trauma patient in need of transfusion therapy comprising providing a trauma patient by between 1.5 and 10 fold with oxygen reduced stored blood that has an oxygen saturation of 20% or less prior to and during storage. In an aspect, the u-NGAL level is reduced by between 2 and 3 fold relative to the u-NGAL level of a patient transfused with conventionally stored blood. In another aspect, the u-NGAL level is reduced by between 3 and 4 fold relative to the u-NGAL level of a patient transfused with conventionally stored blood. In another aspect, the u-NGAL level is reduced by between 4 and 10 folds. In another aspect, the u-NGAL level is reduced by between 6 and 9 fold relative to the u-NGAL level of a patient transfused with conventionally stored blood. In a further aspect, the u-NGAL level is reduced by between 2 and 5 fold relative to the u-NGAL level of a patient transfused with conventionally stored blood. In another aspect, the u-NGAL level is reduced by between 10 and 50 fold relative to the u-NGAL level of a patient transfused with conventionally stored blood.

Methods of the present disclosure provide for, and include, reducing urinary neutrophil gelatinase-associated lipocalin (u-NGAL) levels in a trauma patient in need of transfusion therapy comprising providing a trauma patient by at least 1.5 fold with oxygen reduced stored blood that has an oxygen saturation of 20% or less prior to and during storage. In an aspect, the u-NGAL level is reduced by at least 2 fold relative to the u-NGAL level of a patient transfused with conventionally stored blood. In another aspect, the u-NGAL level is reduced by at least 3 fold relative to the u-NGAL level of a patient transfused with conventionally stored blood. In another aspect, the u-NGAL level is reduced by at least 4 fold relative to the u-NGAL level of a patient transfused with conventionally stored blood. In another aspect, the u-NGAL level is reduced by at least 5 fold relative to the u-NGAL level of a patient transfused with conventionally stored blood. In a further aspect, the u-NGAL level is reduced by at least 6 fold relative to the u-NGAL level of a patient transfused with conventionally stored blood. In another aspect, the u-NGAL, level is reduced by at least 7 fold relative to the u-NGAL level of a patient transfused with conventionally stored blood. In another aspect, the u-NGAL level is reduced by at least 8 fold relative to the u-NGAL level of a patient transfused with conventionally stored blood. In another aspect, the u-NGAL level is reduced by at least 9 fold. In another aspect, the u-NGAL level is reduced by at least 10 fold. In a further aspect, the u-NGAL level is reduced by at least 50 fold.

Methods of the present disclosure provide for, and include, reducing serum creatinine levels in a trauma patient in need of transfusion therapy comprising providing a trauma patient with oxygen reduced stored blood that has an oxygen saturation of 20% or less prior to and during storage. In art aspect, the serum creatinine level is reduced by at least 5% relative to the serum creatinine level of a patient transfused with conventionally stored blood. In another aspect, the serum creatinine level is reduced by at least 10% relative to the serum creatinine level of a patient transfused with conventionally stored blood. In another aspect, the serum creatinine level is reduced by at least 20% relative to the serum creatinine level of a patient transfused with conventionally stored blood. In another aspect, the serum creatinine level is reduced by at least 30% relative to the serum creatinine level of a patient transfused with conventionally stored blood. In another aspect, the serum creatinine level is reduced by at least 40% relative to the serum creatinine level of a patient transfused with conventionally stored blood. In another aspect, the serum creatinine level is reduced by at least 50% relative to the serum creatinine level of a patient transfused with conventionally stored blood. In another aspect, the serum creatinine level is reduced by at least 60% relative to the serum creatinine level of a patient transfused with conventionally stored blood. In another aspect, the serum creatinine level is reduced by at least 70% relative to the serum creatinine level of a patient transfused with conventionally stored blood. In yet another aspect, the serum creatinine level is reduced by at least 80% relative to the serum creatinine level of a patient transfused with conventionally stored blood. In a further aspect, the serum creatinine level is reduced by at least 90% relative to the serum creatinine level of a patient transfused with conventionally stared blood. In a further aspect, the serum creatinine level is reduced by between 1 and 10%, 10 and 20%, 20 and 30%, 30 and 40%, 40 and 50%, 50 and 60%, 60 and 70%, 70 and 80%, 80 and 90%, or 90 and 95% relative to the serum creatinine level of a patient transfused with conventionally stored blood.

Methods of the present disclosure provide for, and include, reducing serum creatinine levels in a trauma patient in need of transfusion therapy by between 1.5 and 10 fold comprising providing a trauma patient with oxygen reduced stored blood that has an oxygen saturation of 20% or less prior to and during storage. In an aspect, the serum creatinine level is reduced by between 2 and 3 fold relative to the serum creatinine level of a patient transfused with conventionally stored blood. In another aspect, the serum creatinine level is reduced by between 3 and 4 fold relative to the serum creatinine level of a patient transfused with conventionally stored blood. In another aspect, the serum creatinine level is reduced by between 4 and 10 fold relative to the serum creatinine level of a patient transfused with conventionally stored blood. In another aspect, the serum creatinine level is reduced by between 6 and 9 fold relative to the serum creatinine level of a patient transfused with conventionally stored blood, in a further aspect, the serum creatinine level is reduced by between 2 and 5 fold relative to the serum creatinine level of a patient transfused with conventionally stored blood. In another aspect, the serum creatinine level is reduced by between 10 and 50 fold relative to the serum creatinine level of a patient transfused with conventionally stored blood.

Methods of the present disclosure provide far, and include, reducing serum creatinine levels in a trauma patient in need of transfusion therapy by at least 1.5 fold comprising providing a trauma patient with oxygen reduced stored blood that has an oxygen saturation of 20% or less prior to and during storage. In an aspect, the serum creatinine level is reduced by at least 2 fold relative to the serum creatinine level of a patient transfused with conventionally stored blood. In another aspect, the serum creatinine level is reduced by at least 3 fold relative to the AST level of a patient transfused with conventionally stored blood. In another aspect, the serum creatinine level is reduced by at least 4 fold relative to the serum creatinine level of a patient transfused with conventionally stored blood. In another aspect, the serum creatinine level is reduced by at least 5 fold. In a further aspect, the serum creatinine level is reduced by at least 6 fold relative to the serum creatinine level of a patient transfused with conventionally stored blood. In another aspect, the serum creatinine level is reduced by at least 7 fold relative to the serum creatinine level of a patient transfused with conventionally stared blood. In another aspect, the serum creatinine level is reduced by at least 8 fold relative to the serum creatinine level of a patient transfused with conventionally stored blood. In another aspect, the serum creatinine level is reduced by at least 9 fold relative to the serum creatinine level of a patient transfused with conventionally stored blood. In another aspect, the serum creatinine level is reduced by at least 10 fold relative to the serum creatinine level of a patient transfused with conventionally stored blood.

Methods of the present disclosure provide for, and include, reducing serum creatinine levels in a trauma patient in need of transfusion therapy to between 0.5 and 1.5 mg/dL comprising providing a trauma patient with oxygen reduced stored blood that has an oxygen saturation of 20% or less prior to and during storage. In an aspect, the serum creatinine level is reduced to between 0.5 and 1 mg/dL relative to the serum creatinine level of a patient transfused with conventionally stored blood. In an aspect, the serum creatinine level is reduced to between 0.8 and 1 mg/dL relative to the serum creatinine level of a patient transfused with conventionally stored blood. In another aspect, the serum creatinine level is reduced to between 0.7 and 1.5 mg/dL relative to the serum creatinine level of a patient transfused with conventionally stored blood.

Methods of the present disclosure provide for, and include, reducing serum creatinine levels in a trauma patient in need of transfusion therapy to less than 1.5 mg/dL comprising providing a trauma patient with oxygen reduced stored blood that has an oxygen saturation of 20% or less prior to and during storage. In an aspect, the serum creatinine level is reduced to less than 1.4 mg/dL relative to the serum creatinine level of a patient transfused with conventionally stored blood. In an aspect, the serum creatinine level is reduced to less than 1 mg/dL. In another aspect, the serum creatinine level is reduced to less than 0.8 mg/dL relative to the serum creatinine level of a patient transfused with conventionally stored blood.

Methods of the present disclosure provide for, and include, reducing BUN levels in a trauma patient comprising providing a trauma patient in need of transfusion therapy with oxygen reduced stored blood that has an oxygen saturation of 20% or less prior to and during storage. In an aspect, the BUN level is reduced by at least 5% relative to the BUN level of a patient transfused with conventionally stored blood. In another aspect, the BUN level is reduced by at least 10% relative to the BUN level of a patient transfused with conventionally stored blood. In another aspect, the BUN level is reduced by at least 20% relative to the BUN level of a patient transfused with conventionally stored blood. In another aspect, the BUN level is reduced by at least 30% relative to the BUN level of a patient transfused with conventionally stored blood. In another aspect, the BUN level is reduced by at least 40% relative to the BUN level of a patient transfused with conventionally stored blood. In another aspect, the BUN level is reduced by at least 50% relative to the BUN level of a patient transfused with conventionally stored blood. In another aspect, the BUN level is reduced by at least 60% relative to the BUN level of a patient transfused with conventionally stored blood. In another aspect, the BUN level is reduced by at least 70% relative to the BUN level of a patient transfused with conventionally stored blood. In yet another aspect, the BUN level is reduced by at least 80% relative to the BUN level of a patient transfused with conventionally stored blood. In a further aspect, the BUN level is reduced by at least 90% relative to the BUN level of a patient transfused with conventionally stored blood. In a further aspect, the BUN level is reduced by between 1 and 10%, 10 and 20%, 20 and 30%, 30 and 40%, 40 and 50%, 50 and 60%, 60 and 70%, 70 and 80%, 80 and 90%, or 90 and 95% relative to the BUN level of a patient transfused with conventionally stored blood.

Methods of the present disclosure provide for, and include, reducing BUN levels in a trauma patient by between 1.5 and 10 fold comprising providing a trauma patient with oxygen reduced stored blood that has an oxygen saturation of 20% or less prior to and during storage. In an aspect, the BUN level is reduced by between 2 and 3 fold relative to the BUN level of a patient transfused with conventionally stored blood. In another aspect, the BUN level is reduced by between 3 and 4 folds. In another aspect, the BUN level is reduced by between 4 and 10 fold relative to the BUN level of a patient transfused with conventionally stored blood. In another aspect, the BUN level is reduced by between 6 and 9 fold relative to the BUN level of a patient transfused with conventionally stored blood. In a further aspect, the BUN level is reduced by between 2 and 5 fold relative to the BUN level of a patient transfused with conventionally stored blood. In another aspect, the BUN level is reduced by between 10 and 100 fold relative to the BUN level of a patient transfused with conventionally stored blood.

Methods of the present disclosure provide for, and include, reducing BUN levels in a trauma patient by at least 1.5 fold comprising providing a trauma patient in need of transfusion therapy with oxygen reduced stored blood that has an oxygen saturation of 20% or less prior to and during storage. In an aspect, the BUN level is reduced by at least 2 fold relative to the BUN level of a patient transfused with conventionally stored blood. In another aspect, the BUN level is reduced by at least 3 fold relative to the BUN level of a patient transfused with conventionally stored blood. In another aspect, the BUN level is reduced by at least 4 fold relative to the BUN level of a patient transfused with conventionally stored blood. In another aspect, the BUN level is reduced by at least 5 fold relative to the BUN level of a patient transfused with conventionally stored blood. In a further aspect, the BUN level is reduced by at least 6 fold. In another aspect, the BUN level is reduced by at least 7 fold relative to the BUN level of a patient transfused with conventionally stored blood. In another aspect, the BUN level is reduced by at least 8 fold relative to the BUN level of a patient transfused with conventionally stored blood. In another aspect, the BUN level is reduced by at least 9 fold relative to the BUN level of a patient transfused with conventionally stored blood. In another aspect, the BUN level is reduced by at least 10 fold relative to the BUN level of a patient transfused with conventionally stored blood.

Methods of the present disclosure provide for, and include, reducing the percentage of CD45+ neutrophils in a trauma patient comprising providing a trauma patient with oxygen reduced stored blood that has an oxygen saturation of 20% or less prior to and during storage. In an aspect, the percentage of CD45+ neutrophils is reduced by at least 5% relative to the CD45+ neutrophil level of a patient transfused with conventionally stored blood. In another aspect, the percentage of CD45+ neutrophils is reduced by at least 10% relative to the CD45+ neutrophil level of a patient transfused with conventionally stored blood. In another aspect, the percentage of CD45+ neutrophils is reduced by at least 20% relative to the CD45+ neutrophil level of a patient transfused with conventionally stored blood. In another aspect, the percentage of CD45+ neutrophils is reduced by at least 30% relative to the CD45+ neutrophil level of a patient transfused with conventionally stored blood. In another aspect, the percentage of CD45+ neutrophils is reduced by at least 40% relative to the CD45+ neutrophil level of a patient transfused with conventionally stored blood. In another aspect, the percentage of CD45+ neutrophils is reduced by at least 50% relative to the CD45+ neutrophil level of a patient transfused with conventionally stored blood. In another aspect, the percentage of CD45+ neutrophils is reduced by at least 60% relative to the CD45+ neutrophil level of a patient transfused with conventionally stored blood. In another aspect, the percentage of CD45+ neutrophils is reduced by at least 70% relative to the CD45+ neutrophil level of a patient transfused with conventionally stored blood. In yet another aspect, the percentage of CD45+ neutrophils is reduced by at least 80% relative to the CD45+ neutrophil level of a patient transfused with conventionally stored blood. In a further aspect, the percentage of CD45+ neutrophils is reduced by at least 90% relative to the CD45+ neutrophil level of a patient transfused with conventionally stored blood. In a further aspect, the percentage of CD45+ neutrophils is reduced by between 1 and 10%, 10 and 20%, 20 and 30%, 30 and 40%, 40 and 50%, 50 and 60%, 60 and 70%, 70 and 80%, 80 and 90%, or 90 and 95% relative to the CD45+ neutrophil level of a patient transfused with conventionally stored blood.

Methods of the present disclosure provide for, and include, reducing the percentage of CD45+ neutrophils in a trauma patient in need of transfusion therapy by between 1.5 and 10 fold comprising providing a trauma patient with oxygen reduced stored blood that has an oxygen saturation of 20% or less prior to and during storage. In an aspect, the percentage of CD45+ neutrophils is reduced by between 2 and 3 fold relative to the CD45+ neutrophil level of a patient transfused with conventionally stored blood. In another aspect, the percentage of CD45+ neutrophils is reduced by between 3 and 4 fold relative to the CD45+ neutrophil level of a patient transfused with conventionally stored blood. In another aspect, the percentage of CD45+ neutrophils is reduced by between 4 and 10 fold relative to the CD45+ neutrophil level of a patient transfused with conventionally stored blood. In another aspect, the percentage of CD45+ neutrophils is reduced by between 6 and 9 fold relative to the CD45+ neutrophil level of a patient transfused with conventionally stored blood. In a further aspect, the percentage of CD45+ neutrophils is reduced by between 2 and 5 fold relative to the CD45+ neutrophil level of a patient transfused with conventionally stored blood. In another aspect, the percentage of CD45+ neutrophils is reduced by between 10 and 50 fold relative to the CD45+ neutrophil level of a patient transfused with conventionally stored blood.

Methods of the present disclosure provide for, and include, reducing the percentage of CD45+ neutrophils in a trauma patient in need of transfusion therapy by at least 1.5 fold comprising providing a trauma patient with oxygen reduced stored blood that has an oxygen saturation of 20% or less prior to and during storage. In an aspect, the percentage of CD45+ neutrophils is reduced by at least 2 fold relative to the CD45+ neutrophil level of a patient transfused with conventionally stored blood. In another aspect, the percentage of CD45+ neutrophils is reduced by at least 3 fold relative to the CD45+ neutrophil level of a patient transfused with conventionally stored blood. In another aspect, the percentage of CD45+ neutrophils is reduced by at least 4 fold relative to the CD45+ neutrophil level of a patient transfused with conventionally stored blood. In another aspect, the percentage of CD45+ neutrophils is reduced by at least 5 fold relative to the CD45+ neutrophil level of a patient transfused with conventionally stored blood. In a further aspect, the percentage of CD45+ neutrophils is reduced by at least 6 fold relative to the CD45+ neutrophil level of a patient transfused with conventionally stored blood. In another aspect, the percentage of CD45+ neutrophils is reduced by at least 7 fold relative to the CD45+ neutrophil level of a patient transfused with conventionally stored blood. In another aspect, the percentage of CD45+ neutrophils is reduced by at least 8 fold relative to the CD45+ neutrophil level of a patient transfused with conventionally stored blood. In another aspect, the percentage of CD45+ neutrophils is reduced by at least 9 fold relative to the CD45+ neutrophil level of a patient transfused with conventionally stored blood. In another aspect, the percentage of CD45+ neutrophils is reduced by at least 10 fold relative to the CD45+ neutrophil level of a patient transfused with conventionally stored blood.

Methods of the present disclosure provide for, and include, reducing the CXCL1 levels in a trauma patient in need of transfusion therapy comprising providing a trauma patient with oxygen reduced stored blood that has an oxygen saturation of 20% or less prior to and during storage. In an aspect, the CXCL1 level is reduced by at least 5% relative to the CXCL1 level of a patient transfused with conventionally stored blood. In another aspect, the CXCL1 level is reduced by at least 10% relative to the CXCL1 level of a patient transfused with conventionally stored blood. In another aspect, the CXCL1 level is reduced by at least 20% relative to the CXCL1 level of a patient transfused with conventionally stored blood. In another aspect, the CXCL1 level is reduced by at least 30% relative to the CXCL1 level of a patient transfused with conventionally stored blood. In another aspect, the CXCL1 level is reduced by at least 40% relative to the CXCL1 level of a patient transfused with conventionally stored blood. In another aspect, the CXCL1 level is reduced by at least 50% relative to the CXCL1 level of a patient transfused with conventionally stored blood. In another aspect, the CXCL1 level is reduced by at least 60% relative to the CXCL1 level of a patient transfused with conventionally stored blood. In another aspect, the CXCL1 level is reduced by at least 70% relative to the CXCL1 level of a patient transfused with conventionally stored blood. In yet another aspect, the CXCL1 level is reduced by at least 80% relative to the CXCL1 level of a patient transfused with conventionally stored blood. In a further aspect, the CXCL1 level is reduced by at least 90% relative to the CXCL1 level of a patient transfused with conventionally stored blood. In a further aspect, the CXCL1 level is reduced by between 1 and 10%, 10 and 20%, 20 and 30%, 30 and 40%, 40 and 50%, 50 and 60%, 60 and 70%, 70 and 80%, 80 and 90%, or 90 and 95% relative to the CXCL1 level of a patient transfused with conventionally stored blood Methods of the present disclosure provide for, and include, reducing the CXCL1 levels in a trauma patient by between 1.5 and 10 fold comprising providing a trauma patient with oxygen reduced stored blood that has an oxygen saturation of 20% or less prior to and during storage. In an aspect, the CXCL1 level is reduced by between 2 and 3 fold relative to the CXCL1 level of a patient transfused with conventionally stored blood. In another aspect, the CXCL1 level is reduced by between 3 and 4 fold relative to the CXCL1 level of a patient transfused with conventionally stored blood. In another aspect, the CXCL1 level is reduced by between 4 and 10 fold relative to the CXCL1 level of a patient transfused with conventionally stored blood. In another aspect, the CXCL1 level is reduced by between 6 and 9 fold relative to the CXCL1 level of a patient transfused with conventionally stored blood. In a further aspect, the CXCL1 level is reduced by between 2 and 5 fold relative to the CXCL1 level of a patient transfused with conventionally stored blood. In another aspect, the CXCL1 level is reduced by between 10 and 100 fold relative to the CXCL1 level of a patient transfused with conventionally stored blood.

Methods of the present disclosure provide for, and include, reducing the CXCL1 levels in a trauma patient by at least 1.5 fold comprising providing a trauma patient with oxygen reduced stored blood that has an oxygen saturation of 20% or less prior to and during storage. In an aspect, the CXCL1 level is reduced by at least 2 fold relative to the CXCL1 level of a patient transfused with conventionally stored blood. In another aspect, the CXCL1 level is reduced by at least 3 fold relative to the CXCL1 level of a patient transfused with conventionally stored blood. In another aspect, the CXCL1 level is reduced by at least 4 fold relative to the CXCL1 level of a patient transfused with conventionally stored blood. In another aspect, the CXCL1 level is reduced by at least 5 fold relative to the CXCL1 level of a patient transfused with conventionally stored blood. In a further aspect, the CXCL1 level is reduced by at least 6 fold relative to the CXCL1 level of a patient transfused with conventionally stored blood. In another aspect, the CXCL1 level is reduced by at least 7 fold relative to the CXCL1 level of a patient transfused with conventionally stored blood. In another aspect, the CXCL1 level is reduced by at least 8 fold relative to the CXCL1 level of a patient transfused with conventionally stored blood. In another aspect, the CXCL1 level is reduced by at least 9 fold relative to the CXCL1 level of a patient transfused with conventionally stored blood. In another aspect, the CXCL1 level is reduced by at least 10 fold relative to the CXCL1 level of a patient transfused with conventionally stored blood.

Methods of the present disclosure provide for, and include, reducing the IL-6 levels in a trauma patient in need of transfusion therapy comprising providing a trauma patient with oxygen reduced stored blood that has an oxygen saturation of 20% or less prior to and during storage. In an aspect, the IL-6 level is reduced by at least 5% relative to the IL-6 level of a patient transfused with conventionally stored blood. In another aspect, the IL-6 level is reduced by at least 10% relative to the IL-6 level of a patient transfused with conventionally stored blood. In another aspect, the IL-6 level is reduced by at least 20%. In another aspect, the IL-6 level is reduced by at least 30% relative to the IL-6 level of a patient transfused with conventionally stored blood. In another aspect, the IL-6 level is reduced by at least 40% relative to the IL-6 level of a patient transfused with conventionally stored blood. In another aspect, the IL-6 level is reduced by at least 50% relative to the IL-6 level of a patient transfused with conventionally stored blood. In another aspect, the IL-6 level is reduced by at least 60% relative to the IL-6 level of a patient transfused with conventionally stored blood. In another aspect, the IL-6 level is reduced by at least 70% relative to the IL-6 level of a patient transfused with conventionally stored blood. In yet another aspect, the IL-6 level is reduced by at least 80% relative to the IL-6 level of a patient transfused with conventionally stored blood. In a further aspect, the IL-6 level is reduced by at least 90% relative to the IL-6 level of a patient transfused with conventionally stored blood. In a further aspect, the IL-6 level is reduced by between 1 and 10%, 10 and 20%, 20 and 30%, 30 and 40%, 40 and 50%, 50 and 60%, 60 and 70%, 70 and 80%, 80 and 90%, or 90 and 95% relative to the IL-6 level of a patient transfused with conventionally stored blood.

Methods of the present disclosure provide for, and include, reducing the IL-6 levels in a trauma patient by between 1.5 and 10 fold comprising providing a trauma patient with oxygen reduced stored blood that has an oxygen saturation of 20% or less prior to and during storage. In an aspect, the IL-6 level is reduced by between 2 and 3 fold relative to the IL-6 level of a patient transfused with conventionally stored blood. In another aspect, the IL-6 level is reduced by between 3 and 4 fold relative to the IL-6 level of a patient transfused with conventionally stored blood. In another aspect, the IL-6 level is reduced by between 4 and 10 folds. In another aspect, the IL-6 level is reduced by between 6 and 9 fold relative to the IL-6 level of a patient transfused with conventionally stored blood. In a further aspect, the IL-6 level is reduced by between 2 and 5 fold relative to the IL-6 level of a patient transfused with conventionally stored blood. In another aspect, the IL-6 level is reduced by between 10 and 100 fold relative to the IL-6 level of a patient transfused with conventionally stored blood.

Methods of the present disclosure provide for, and include, reducing the IL-6 levels in a trauma patient by at least 1.5 fold comprising providing a trauma patient in need of transfusion therapy with oxygen reduced stored blood that has an oxygen saturation of 20% or less prior to and during storage. In an aspect, the IL-6 level is reduced by at least 2 fold relative to the IL-6 level of a patient transfused with conventionally stored blood. In another aspect, the IL-6 level is reduced by at least 3 fold relative to the IL-6 level of a patient transfused with conventionally stored blood. In another aspect, the IL-6 level is reduced by at least 4 fold relative to the IL-6 level of a patient transfused with conventionally stored blood. In another aspect, the IL-6 level is reduced by at least 5 fold. In a further aspect, the IL-6 level is reduced by at least 6 fold relative to the IL-6 level of a patient transfused with conventionally stored blood. In another aspect, the IL-6 level is reduced by at least 7 fold relative to the IL-6 level of a patient transfused with conventionally stored blood. In another aspect, the IL-6 level is reduced by at least 8 fold relative to the IL-6 level of a patient transfused with conventionally stored blood. In another aspect, the IL-6 level is reduced by at least 9 fold relative to the IL-6 level of a patient transfused with conventionally stored blood. In another aspect, the IL-6 level is reduced by at least 10 fold relative to the IL-6 level of a patient transfused with conventionally stored blood.

As used herein, the terms "higher", "greater" or "increased" means that the measured values of oxygen reduced and anaerobically stored blood, when compared to the measured values of otherwise equivalently treated conventionally stored blood, are at least 1 standard deviation greater, with a sample size of at least 2 for each compared measured condition.

As used herein, the terms "reduce", "reduced", "lower", "decreased" or "less" means that the measured values of oxygen reduced and anaerobically stored blood when compared to the measured values of otherwise equivalently treated normoxic or hyperoxic conventionally stored blood RBCs, are at least 1 standard deviation lower, with a sample size of at least 5 for each compared measured condition.

As used herein the term "about" refers to ±10%.

As used herein the term "less than" refers to a smaller amount and an amount greater than zero.

The terms "comprises," "comprising," "includes," "including," "having," and their conjugates mean "including but not limited to."

The term "consisting of" means "including and limited to."

The term "consisting essentially of" means that the composition, method or structure can include additional ingredients, steps and/or parts, but only if the additional ingredients, steps and/or parts do not materially alter the basic and novel characteristics of the claimed composition, method or structure.

As used herein, the singular forms "a," "an," and "the" include plural references unless the context clearly dictates otherwise. For example, the term "a compound" or "at least one compound" can include a plurality of compounds, including mixtures thereof.

As used herein, the term "blood" refers to whole blood, leukoreduced RBCs, platelet reduced RBCs, and leukocyte and platelet reduced RBCs. The term blood further includes packed red blood cells, platelet reduced packed red blood cells, leukocyte reduced packed red blood cells, and leukocyte and platelet reduced packed red blood cells. The temperature of blood can vary depending on the stage of the collection process, starting at the normal body temperature of 37° C. at the time and point of collection, but decreasing rapidly to about 30° C. as soon as the blood leaves the patient's body and further thereafter to room temperature in about 6 hours when untreated, and ultimately being refrigerated at between about 4° C. and 6° C. Human red blood cells in vivo are in a dynamic state. The red blood cells contain hemoglobin, the iron-containing protein that carries oxygen throughout the body and gives red blood its color. The percentage of blood volume composed of red blood cells is called the hematocrit. As used herein, unless otherwise limited, RBCs also includes packed red blood cells (pRBCs). Packed red blood cells are prepared from whole blood using centrifugation techniques commonly known in the art. As used herein, unless otherwise indicated, the hematocrit of pRBCs is about 70%. As used herein, oxygen reduced stored RBCs can include oxygen and carbon dioxide reduced stored RBCs. As used herein, oxygen reduced (OR) blood can include oxygen and carbon dioxide (OCR) reduced blood.

As used herein the terms "patient" and "subject" is used interchangeably to mean a person or animal in need of transfusion.

As used herein the term "trauma" includes exsanguination, hemorrhagic trauma.

As used herein the term "hemorrhagic shock" is shock brought on by a loss of circulating blood volume and/or oxygen carrying capacity. Hemorrhagic shock results from any condition associated with blood loss, internal (e.g., gastrointestinal bleeding) or external hemorrhage, and trauma (e.g, penetrating or blunt trauma), among others.

As used herein the term "adverse event" includes an event resulting from hemorrhagic shock in a hemorrhagic trauma patient.

As used herein the terms "injury", "damage", and "failure" refer to an organ not functioning properly or not functioning as is expected in a person or animal without disease or injury.

As used herein, a "unit" of blood is about 450-500 ml including anticoagulant. Suitable anticoagulants include CPD, CPDA1, ACD, and ACD-A.

Throughout this application, various aspects of this disclosure may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as "from 1 to 6" should be considered to have specifically disclosed subranges such as "from 1 to 3," "from 1 to 4," "from 1 to 5," "from 2 to 4," "from 2 to 6," "from 3 to 6," etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques, and procedures for accomplishing a given task including, but not limited to, providing a human patient in need of a blood transfusion with oxygen reduced stored blood having an initial oxygen saturation of 20% or less and stored for at least 2 days.

While the present disclosure has been described with reference to particular embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the scope of the present disclosure.

Therefore, it is intended that the present disclosure not be limited to the particular embodiments disclosed as the best mode contemplated for carrying out the present disclosure, but that the present disclosure will include all embodiments falling within the scope and spirit of the appended claims.

EXAMPLES

Example 1

Collection of Blood and Sample Preparation

Each pool of red blood cells are collected from a total of 12-14 rats in CP2D anticoagulant. The pooled blood is leukoreduced using neonatal leukoreduction filter, component separated and RBCs are stored in AS-3 additive solution. Total of two pools of RBCs are collected. Each pool is split four ways: Unprocessed control (C), sham control (SC), oxygen-reduced (OR) and oxygen and carbon dioxide reduced (OCR). For C, SC, OR and OCR units. RBC subunit is processed by transferring into 80 mL, PVC blood transfer bag and final RBC products are made by gas exchange process. The RBC bags except for C are filled with 100% $N_2$ (for OR), or 95% $N_2$/5% $CO_2$ (for OCR) or air (SC) through sterile filter and gently rotated on its long side at 2-3 RPM (except for C). For OR and OCR units, after 10 minutes, gas is removed through the filter and fresh gas is introduced for subsequent gas exchange process. This process is repeated 5-8 times until target % SO2 of 5-10% as measured by ABL-90 cooximeter (Radiometer Copenhagen) is achieved. SC unit is rotated without any gas exchange for 60 minutes. OR and OCR units are stored anaerobically in a $N_2$-filled canister, while C and SC units are stored in ambient air. All units are stored for 3 weeks at 4° C. and sampled at days 0 or 1, 7, 14, 21, and 28. Two pools were prepared and stored.

Figure 2:
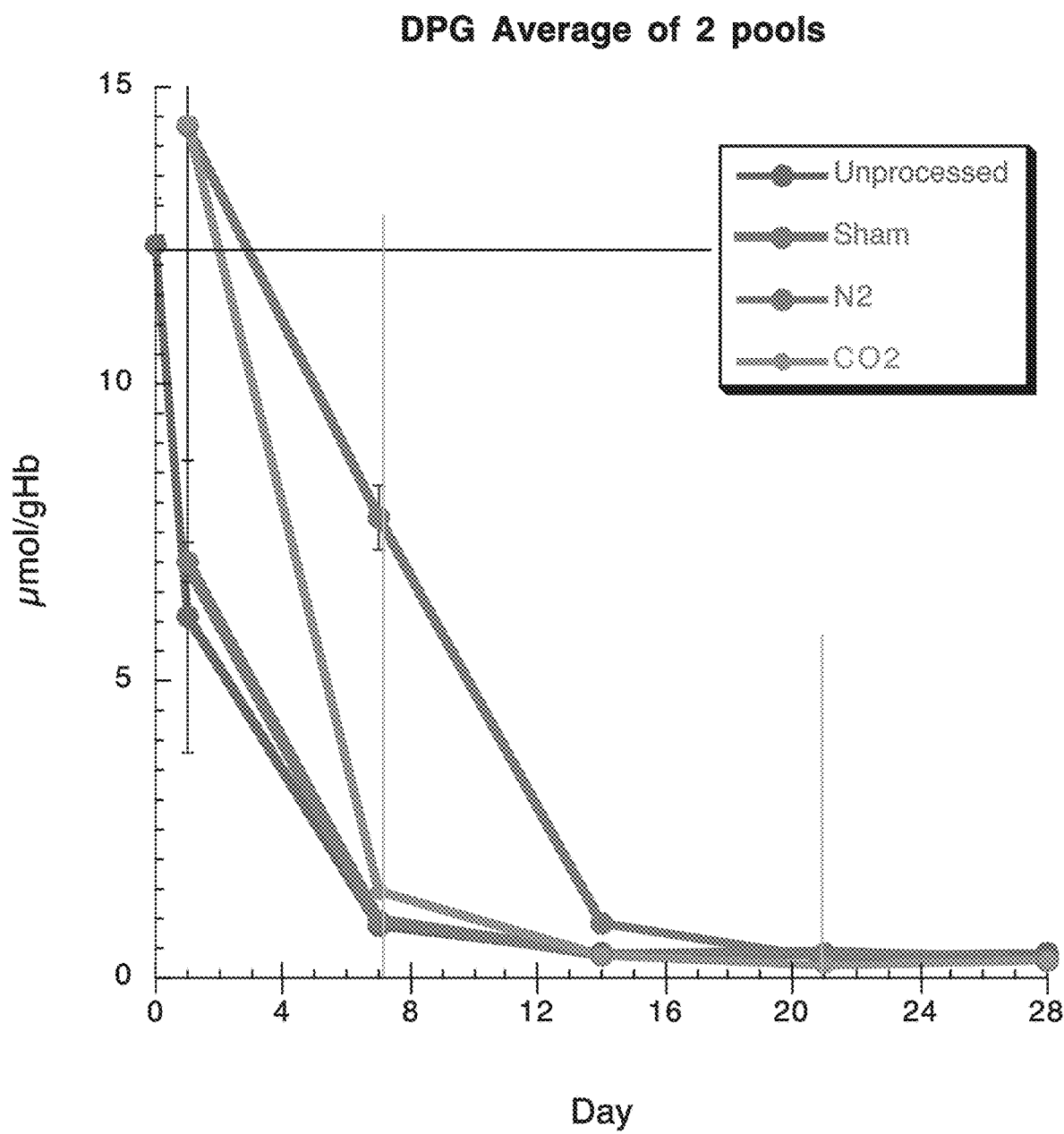
FIG. 2 is a graph presenting the results of an exemplary embodiment according to the present disclosure, comparing 2,3-DPG levels of conventionally stored RBCs (unprocessed, control), sham control (SC), oxygen reduced RBCs ($N_2$; OR), and oxygen and carbon dioxide reduced RBCs ($CO_2$; OCR).

On days 0, 1, 7, 14, 21, and 28, ATP, 2,3-DPG, and homolysis analysis are performed. As shown in FIG. 1, ATP levels are higher in OR-blood at day 21 and OCR-blood at days 7, 14, 21, and 28 compared to conventionally stored blood (control). OR-blood also has higher levels of 2,3-DPG at days 2, 7, and 14, compared to control. OCR-blood also shows a higher level of 2,3-DPG on days 2, 7, and 14 compared to control. See FIG. 2.

Example 2

Recovery of Oxygen Reduced Blood

Figure 3:
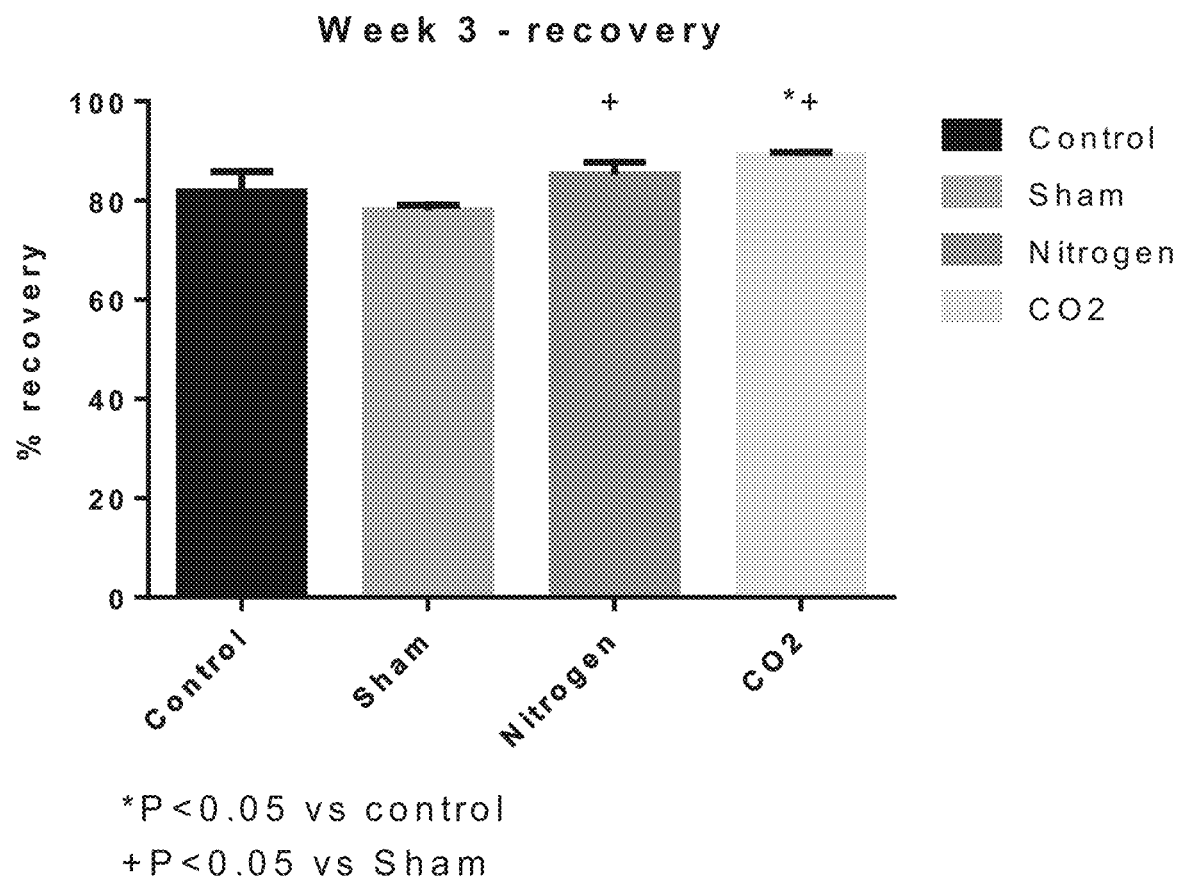
FIG. 3 is a graph presenting the results of an exemplary embodiment according to the present disclosure, presenting a comparison of the percent recovery of control, sham, OR-RBCs, and OCR-RBCS transfused into an animal.

A small volume (less than 200 µL) of Control, OR-, and OCR-blood stored for 3 weeks is labeled with techniteum-99m. Animals are transfused with labeled RBC (less than 200 uL) and circulating radioactivity is measured periodically up to 24 hours in order to estimate fraction of transfused RBC surviving 24 hours after transfusion. As shown in FIG. 3, significantly more OR- and OCR-RBCs are recovered compared to control RBCs when RBCs were stored for three weeks.

Example 3

Rat Model of Hemorrhagic Shock Resuscitation

Collection of blood and sample preparation: Each pool of red blood cells are collected from a total of 12-14 rats in CP2D anticoagulant. The pooled blood is leukoreduced using neonatal leukoreduction filter, component separated and RBCs are stored in AS-3 additive solution. Total of six pools of RBCs are collected. Two pools are prepared for conventional storage (control). Two pools are depleted of oxygen (oxygen reduced; OR), and the remaining two pools of blood are depleted of oxygen and carbon dioxide (oxygen and carbon dioxide reduced; OCR). Each of the four pools to be reduced is processed by transferring RBCs into 600 mL PVC blood transfer bag and final RBC products are made by gas exchange process. The RBC bag is filled with 100% $N_2$ (for OR), or 95% $N_2$/5% $CO_2$ (for OCR) through sterile filter and gently rotated on its long side at 60-90 RPM. After 10 minutes, gas is removed through the filter and fresh gas is introduced for subsequent gas exchange process. This process is repeated 5-8 times until target % SO2 of 5-10% as measured by ABL-90 cooximeter (Radiometer Copenhagen) is achieved. OR and OCR blood is stored anaerobically in a $N_2$-filled canister.

Studies are performed in Sprague-Dawley rats (Charles River Laboratories, Boston, Mass.) weighing 150-200 grams (g). Briefly, animals are anesthetized by administering 40 mg/kg of sodium pentobarbital intraperitoneally. Animals are placed in the supine position on a heating pad to maintain core body temperature at 37 C. Animals are prepared with: (i) a left jugular vein and left femoral artery catheterization, (ii) tracheotomy (polyethylene-90 tube), and (iii) left ventricle (LV) conductance catheter introduction through the right carotid artery. Animals are mechanically ventilated (TOPO ventilator, Kent Scientific, Torrington, Conn.) using room air, with a respiration rate of 50-70 breaths per min and a peak inspiratory pressure of 10-15 cmH2O. After instrumentation, volatile anesthesia (1.5%/vol Isoflurane, Dragerwerk AG, Laubeck, Germany) is administered using a vaporizer connected to the ventilator. Depth of anesthesia is continually verified via toe pinch, as needed, isoflurane was increased by 0.1%/vol to prevent animal discomfort.

Anesthetized animals are hemorrhaged by withdrawing 50% of the animal's blood volume (BV; estimated 7% of body weight) via the femoral artery catheter within 10 min, placing the animals in a hypovolemic shock condition. The hypovolemic shock condition is maintained for 30 min. Resuscitation is implemented by infusion of previously stored RBCs at 300 microliters per min (µL/min) via the femoral artery until Mean arterial pressure (MAP) is stabilized at 90% of the baseline during 60 minutes resuscitation period. At 10, 20, 30, 45 and 60 minutes during this period, MAP and heart rate (HR) are obtained from a femoral artery catheter (PowerLab, AD Instruments, Colorado Springs, Colo.). After 60 mins, hematocrit (Hct) is measured via centrifugation of heparinized capillary tubes. Hemoglobin (Hb), lactate, glucose, K+, Na+, pH, arterial blood gas are determined by ABL90 cooximeter (Radiometer, Copenhagen). Indices of cardiac function and systemic values (MAP, HR, Hct, Hb, and blood gases) are monitored at baseline (BL), during shock, and 10 (Early R), 20, 30, 45, and 60 (Late R) mins post resuscitation. Animals are euthanized at the end of the experiment.

Example 4

Hematocrit Analysis in a Rat Model of Hemorrhagic Shock

Figure 4A:
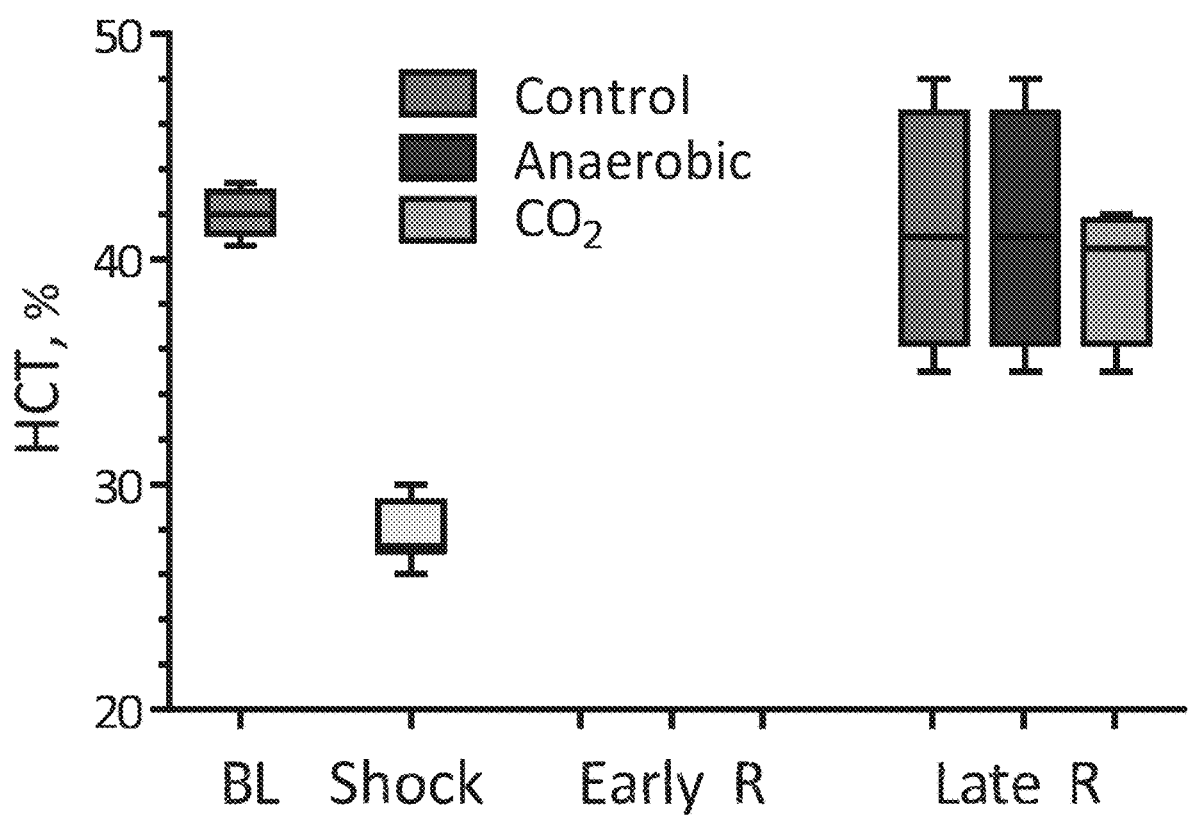
FIGS. 4A and 4B are graphs presenting the results of an exemplary embodiment according to the present disclosure, presenting a comparison of the percent hematocrit in animals resuscitated with control, OR-RBCs, and OCR-RBCs stored for 1 week (FIG. 4A) or 3 weeks (FIG. 4B). BL (baseline) identifies animals not under shock conditions. Shock identifies animals under hemorrhagic shock. Early R identifies a resuscitation period of 10 mins. Late R identifies a resuscitation period of 60 mins.
Figure 4B:
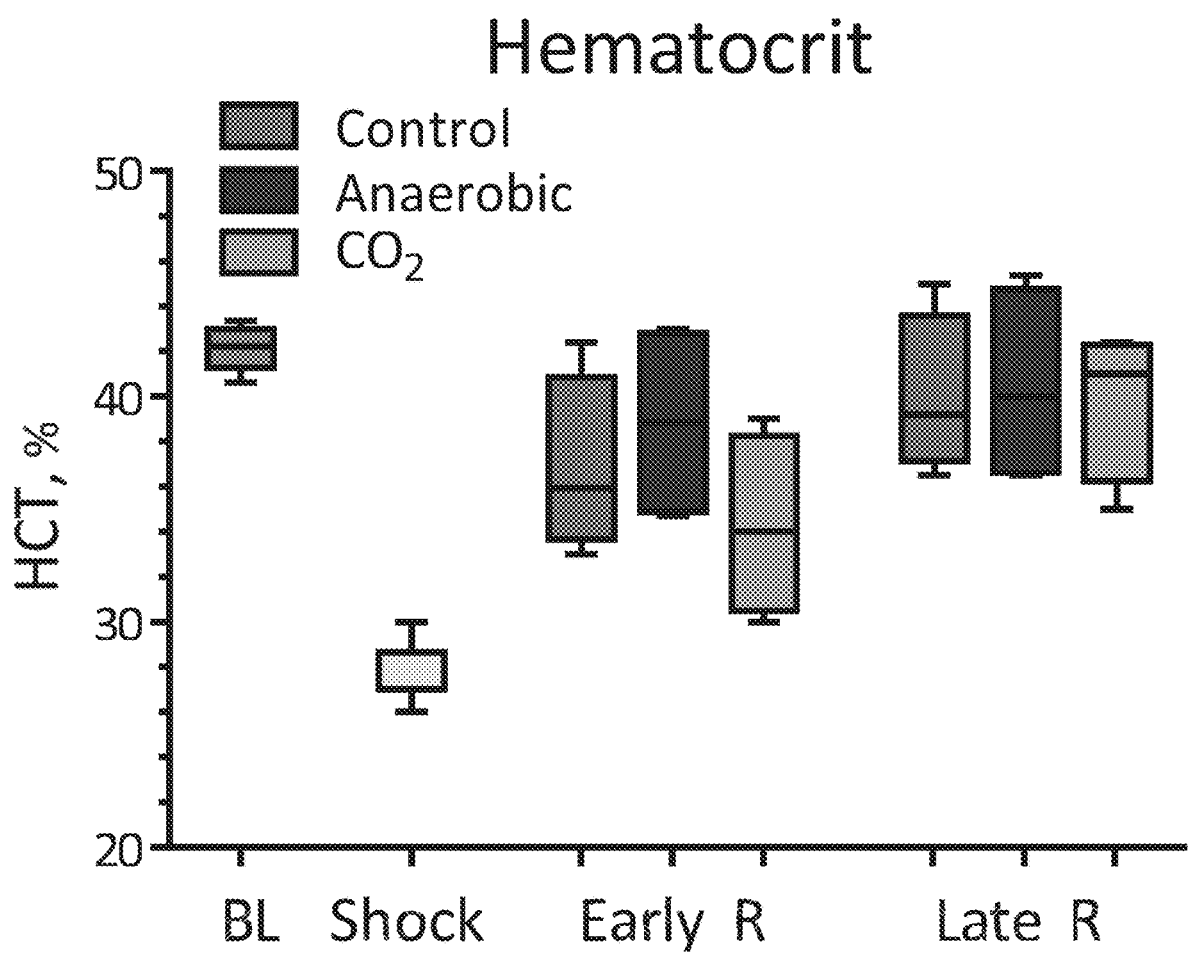

Hematocrit (Hct) is reduced by approximately 30 to 40% after hypovolemic shock is induced. Providing conventionally, OR, or OCR blood stored for 1 week is capable of restoring hematocrit to normal levels. See FIG. 4A, However, as shown in FIG. 4B, OR-blood stored for one week show an increased percent hematocrit compared to control and OCR-blood after 10 mins of resuscitation (Early R). The percent hematocrit of OR-blood remains improved compared to control after 60 mins (Late R) of resuscitation.

Example 5

Mean Arterial Pressure Changes with Oxygen Reduced Blood

Figure 5A:
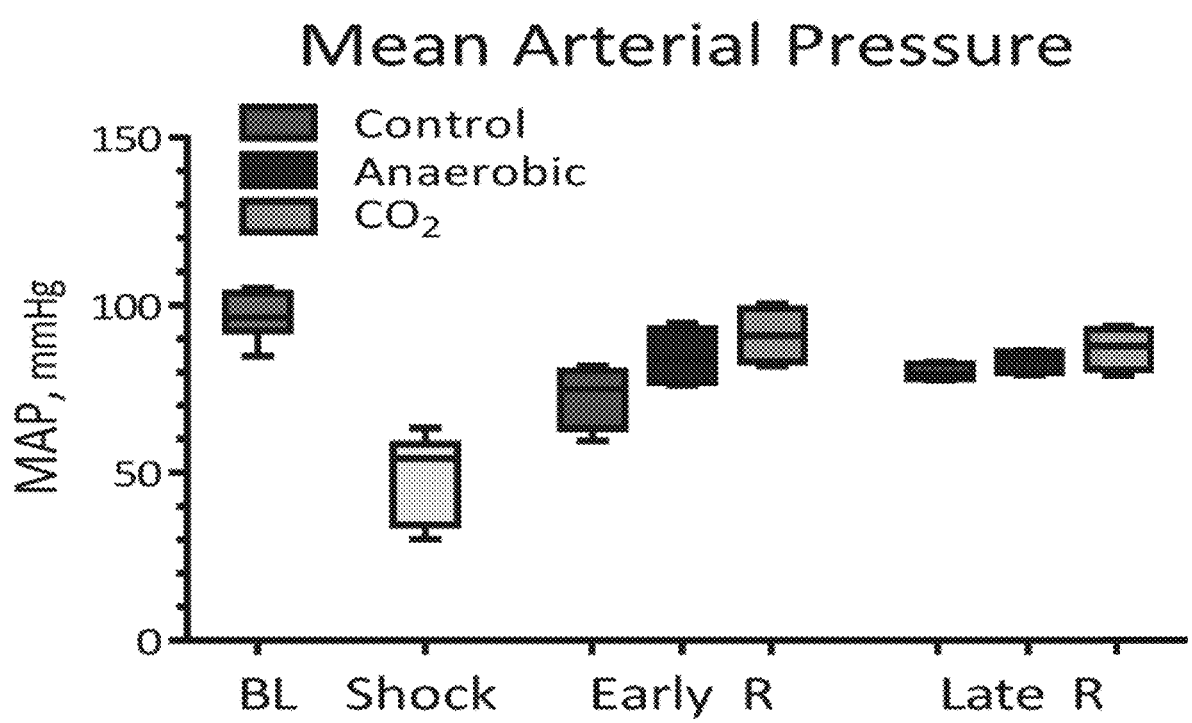
FIGS. 5A and 5B are graphs presenting the results of an exemplary embodiment according to the present disclosure, providing a comparison of the mean arterial pressure (MAP) in animals resuscitated with control, OR-RBCs, and OCR-RBCs stored for 1 week (FIG. 5A) or 3 weeks (FIG. 5B). BL (baseline) identifies animals not under shock conditions. Shock identifies animals under hemorrhagic shock. Early R identifies a resuscitation period of 10 mins. Late R identifies a resuscitation period of 60 mins.
Figure 5B:
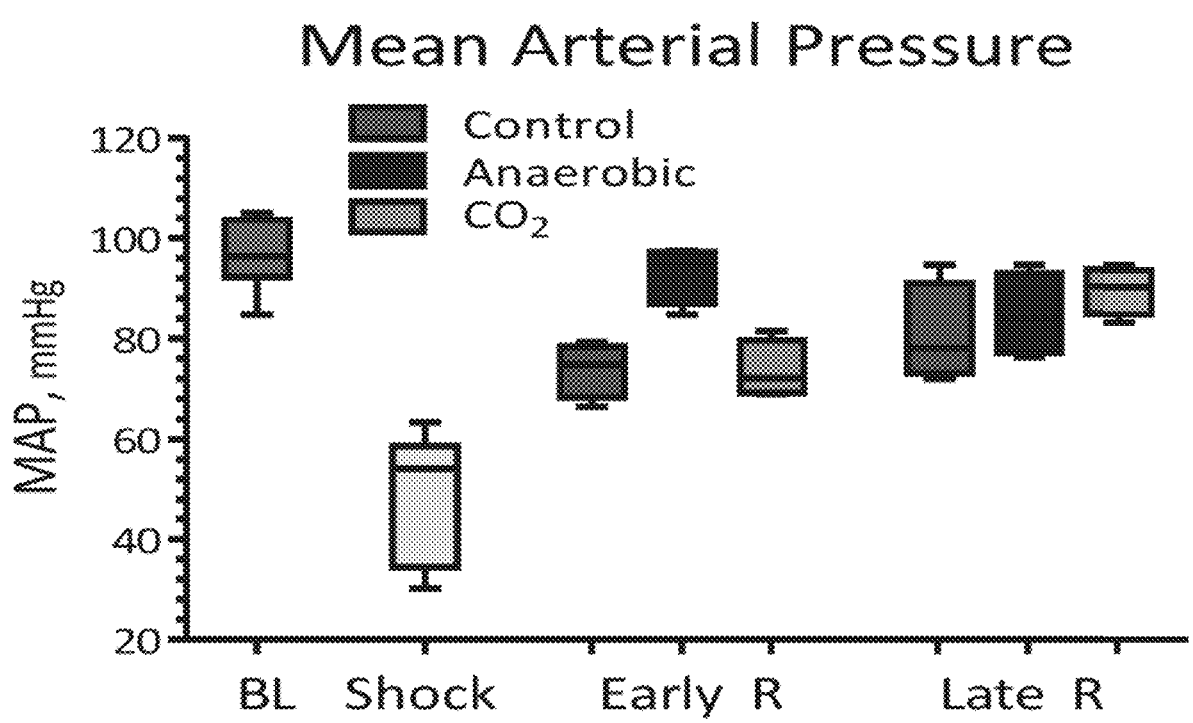
Figure 6A:
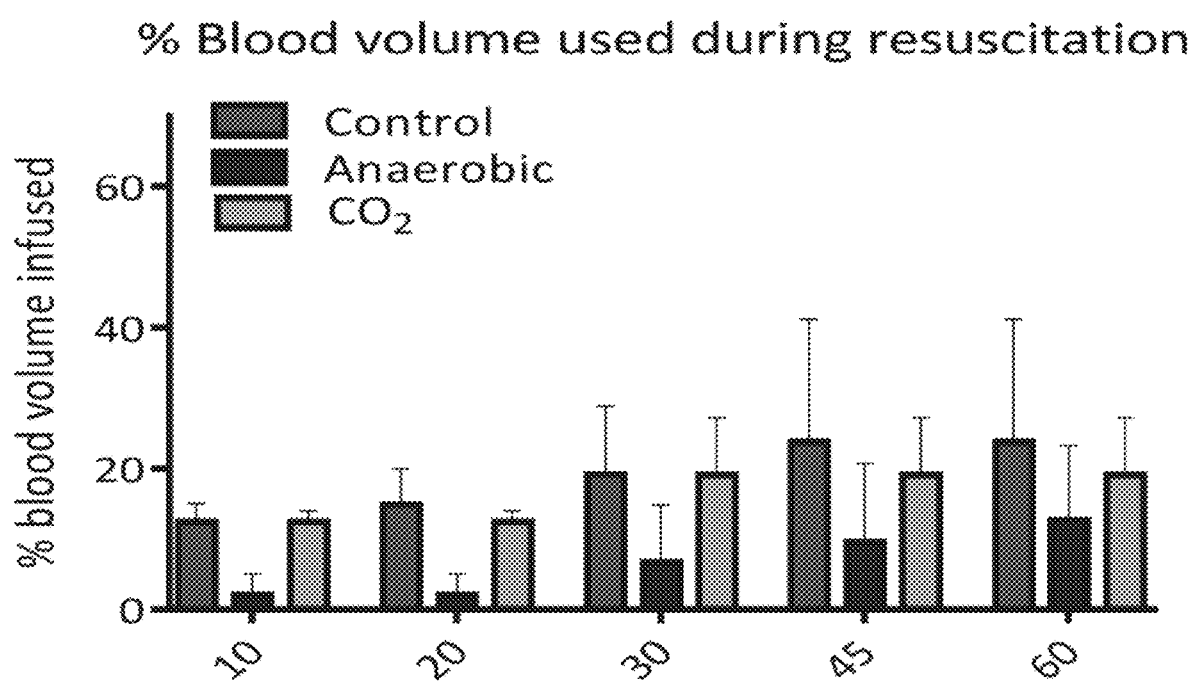
FIGS. 6A and 6B are graphs presenting the results of an exemplary embodiment according to the present disclosure, providing a comparison of the percent blood volume provided to animals during resuscitation after 10, 20, 30, 45, and 60 mins. Control, OR-RBCs, and OCR-RBCs stored for 1 week (FIG. 6A) or 3 weeks (FIG. 6B) are compared.
Figure 6B:
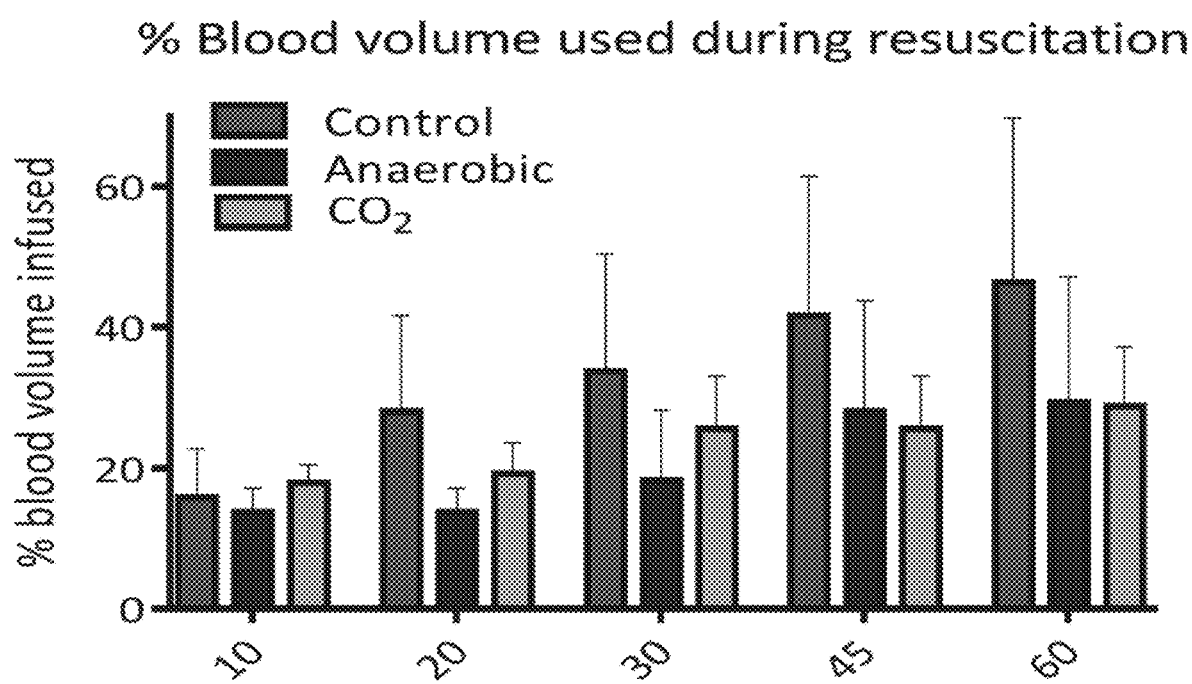

Mean arterial pressure (MAP) is obtained from the femoral artery catheter (PowerLab, AD instruments, Colorado Springs, Colo.). As shown in FIG. 5A, baseline MAP is between 80 and 110 mmHg. MAP is reduced to between 20 and 60 mmHg during hemorrhagic shock. Resuscitation of animals with OR and OCR blood stored for one week increases the MAP to approximately 80 and 90 mmHg, respectively. As shown in FIG. 5B, resuscitation with OR blood, after 10 mins, is able to restore MAP to normal range compared to control. Control and OCR stored blood is able to restore MAP to a normal range after 60 mins of resuscitation. The amount of blood required to resuscitate and preserve hemodynamics with conventionally stored RBCs (control) was greater than OR and OCR RBCs required. See FIG. 6A and FIG. 6B.

Example 6

Metabolic Reaction to Hemorrhagic Shock

Figure 8B:
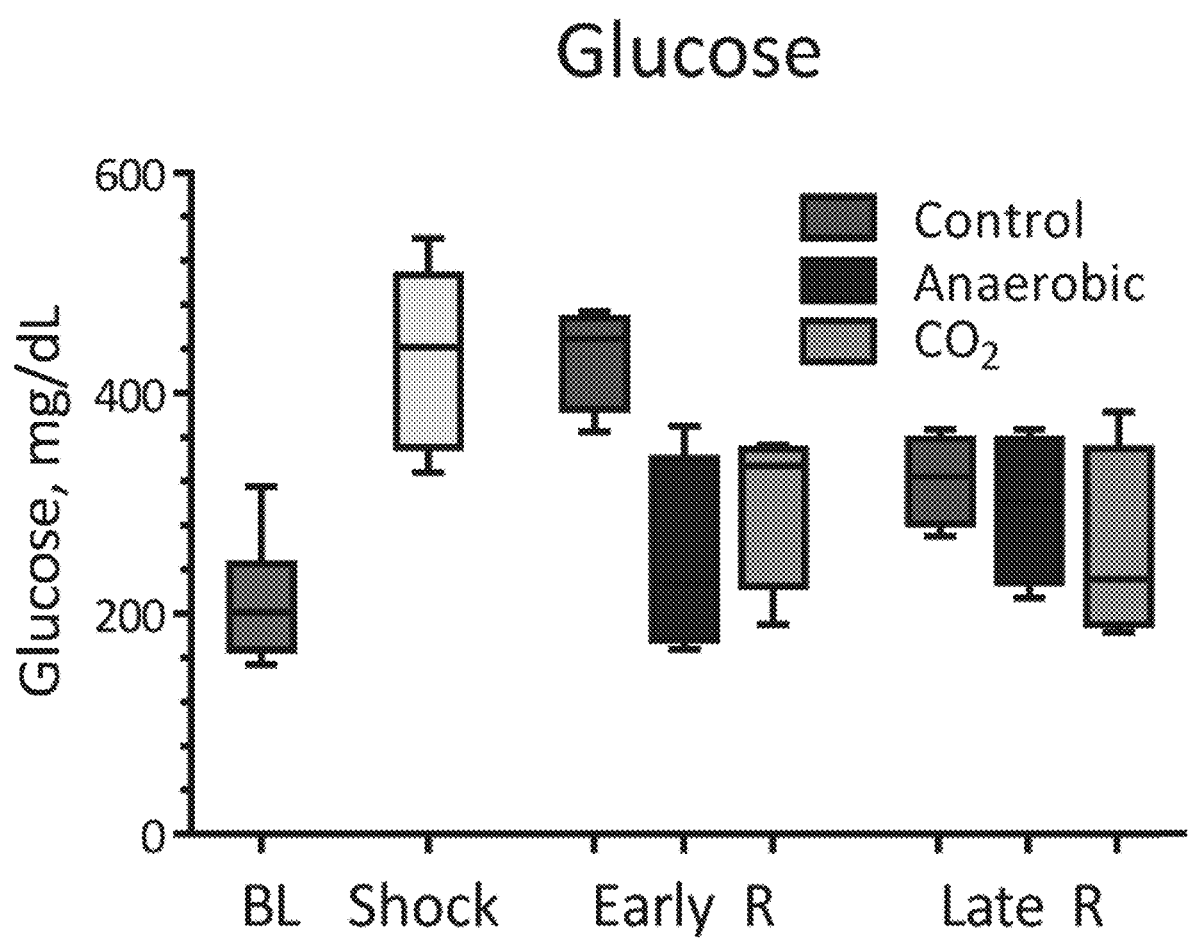

Hemorrhagic shock in animals increases the lactate level from about 2 mmol/L to between about 8 and 14 mmol/L. Resuscitation with OR and OCR RBCs stored for one week reduces lactate levels to near normal levels after just 10 mins of resuscitation. See FIG. 7A. Lactate levels of animals resuscitated with control blood are similar to lactate levels of animals in hemorrhagic shock. Animals treated with control, OR and OCR RBCs for 60 mins show similar lactate levels. As shown, in FIG. 7B, OR RBCs stored for 3 weeks are also able to reduce lactate levels compared to control after 10 mins of resuscitation. However, after 80 mins of resuscitation OCR RBCs restored lactate levels to a normal range. Control and OR RBCs were able to reduce lactate levels but not to the normal range of 1 to 3 mmol/L. Analysis of glucose levels show that the normal range of about 160 mg/dL to about 240 mg/dL glucose is increased to a range of about 320 to about 510 mg/dL in animals under hemorrhagic shock. See FIG. 8A and FIG. 8B. Both OR and OCR RBCs stored for one week decrease glucose levels compared to control after 10 mins of resuscitation. All three samples restored glucose levels to the normal range after 60 mins of resuscitation. As shown in FIG. 8B, OR and OCR RBCs stored for three weeks are also able to decrease glucose levels compared to control after 10 mins of resuscitation. Unlike the RBCs stored for one week, only OR and OCR RBCs were able to restore glucose within the normal range. Thus, both lactate and glucose levels are reduced faster in OR and OCR RBCs compared to control RBCs.

Example 7

Vital Organ Injury and Inflammation

Animals are analyzed for organ injury and inflammation after experiencing hemorrhagic shock and resuscitation.

Figure 9A:
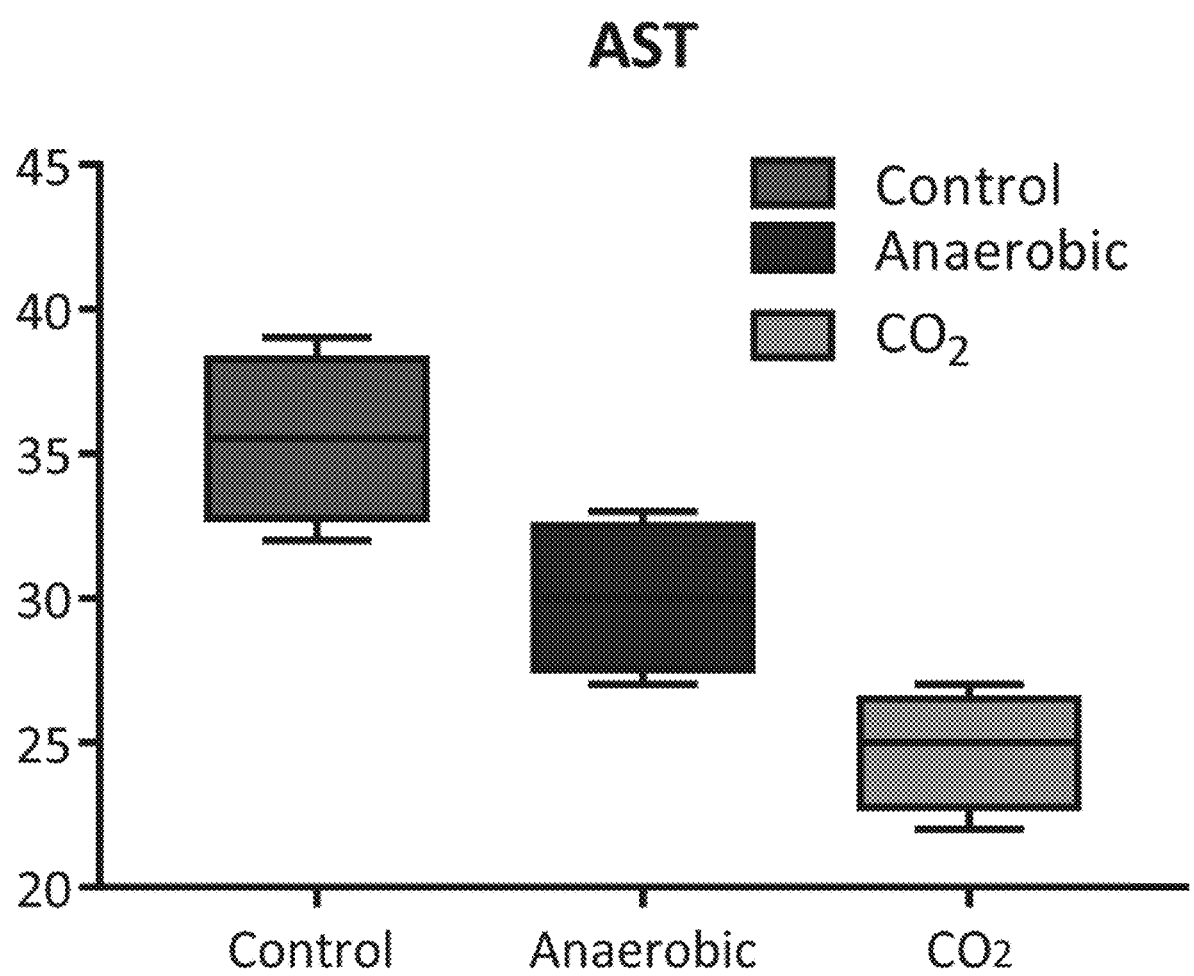
FIGS. 9A and 9B are graphs presenting the results of an exemplary embodiment according to the present disclosure, providing a comparison of the amount of AST in animals resuscitated with control, OR-RBCs, and OCR-RBCS stored for 1 week (FIG. 9A) or 3 weeks (FIG. 9B).
Figure 9B:
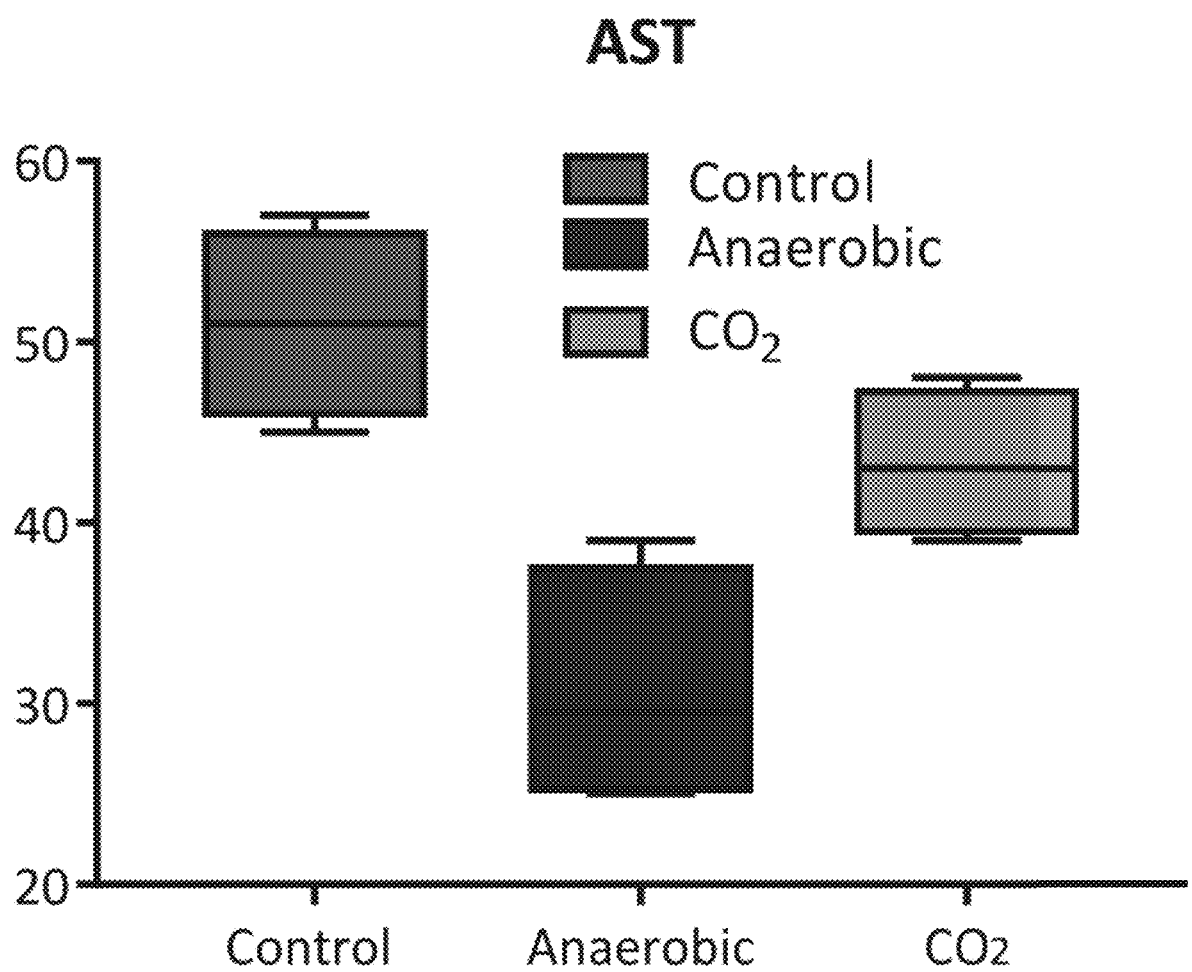
Figure 10A:
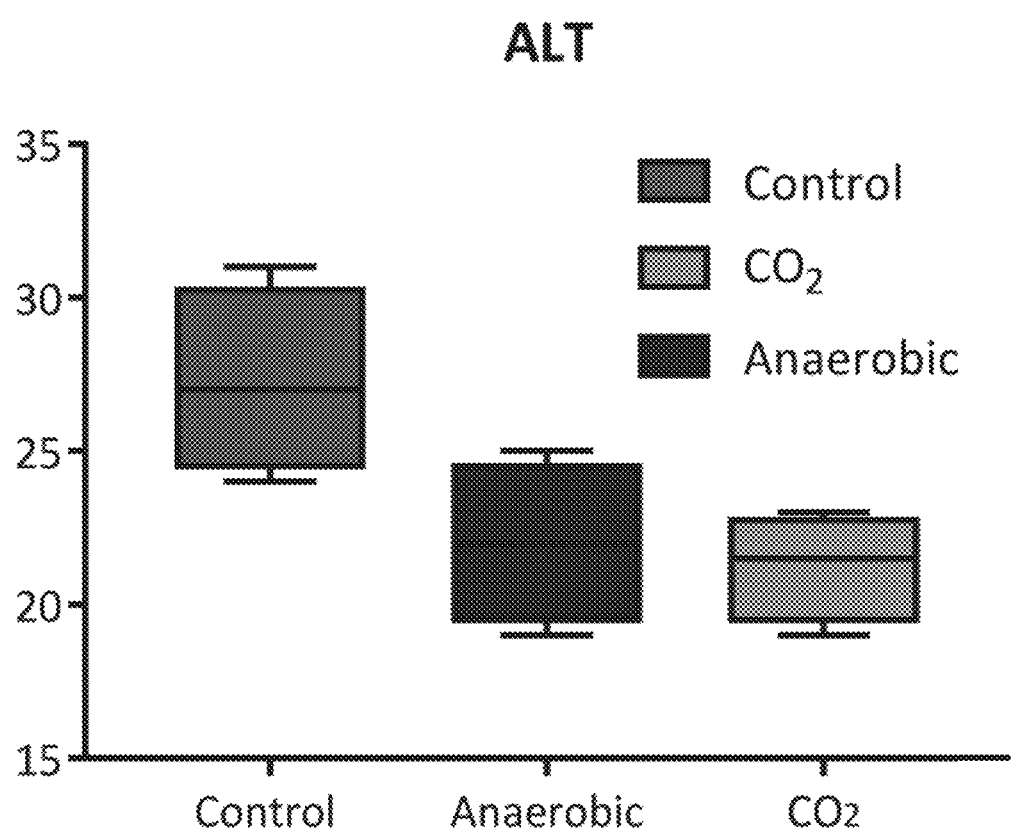
FIGS. 10A and 10B are graphs presenting the results of an exemplary embodiment according to the present disclosure, providing a comparison of the amount of ALT in animals resuscitated with control, OR-RBCs, and OCR-RBCs stored for 1 week (FIG. 10A) Of 3 weeks (FIG. 10B).
Figure 10B:
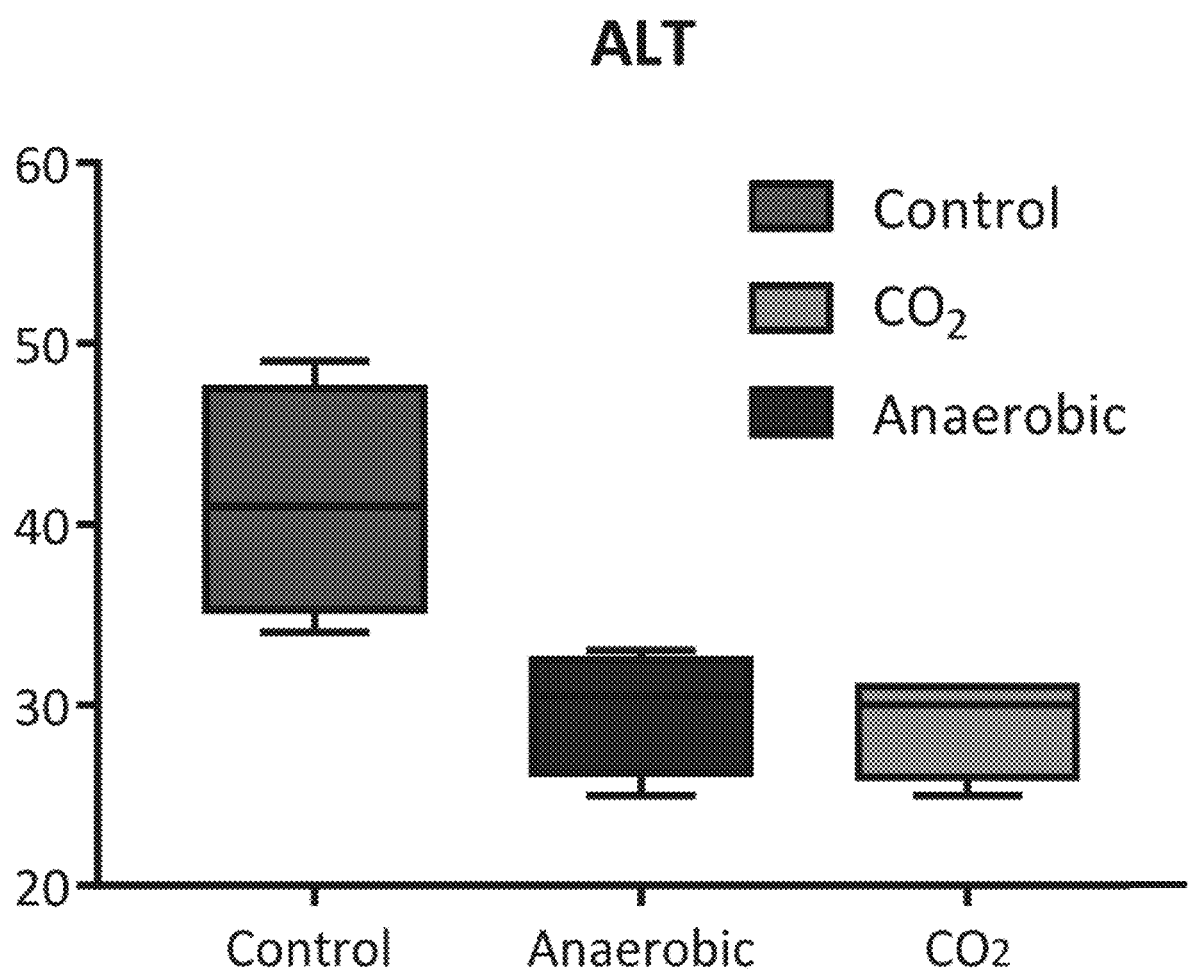
Figure 11A:
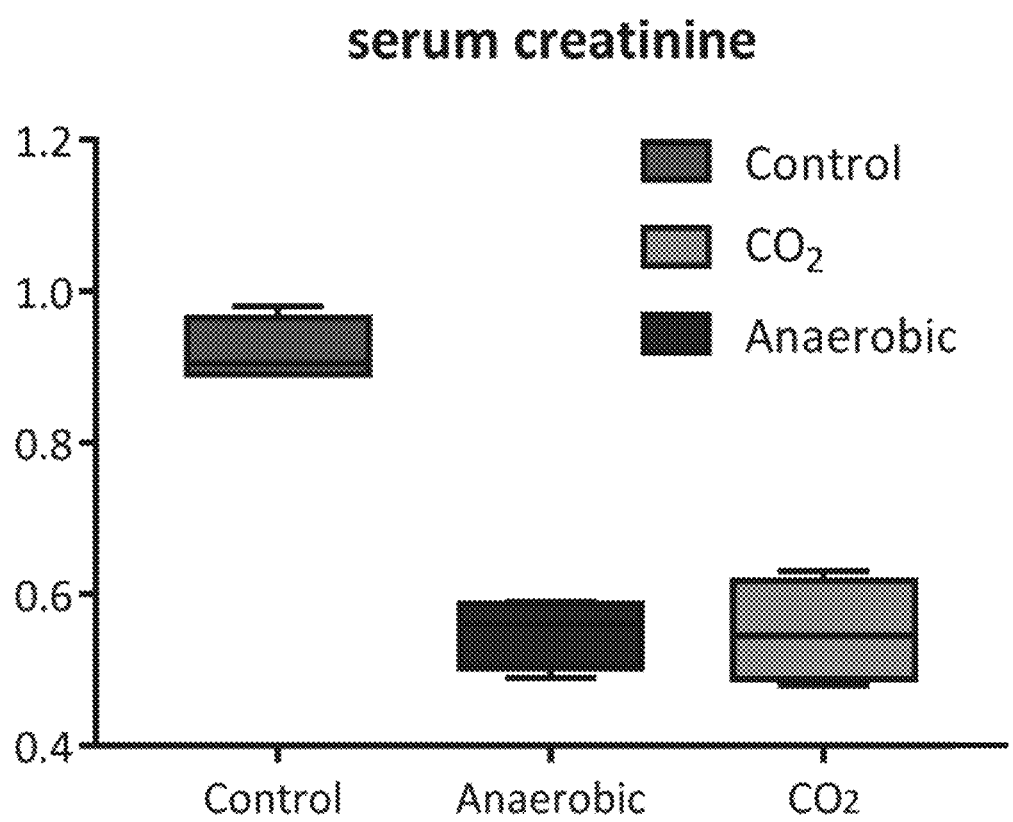
FIGS. 11A and 11B are graphs presenting the results of an exemplary embodiment according to the present disclosure, providing a comparison of the amount of serum creatinine in animals resuscitated with control, OR-RBCs, and OCR-RBCS stored for 1 week (FIG. 11A) or 3 weeks (FIG. 11B).
Figure 11B:
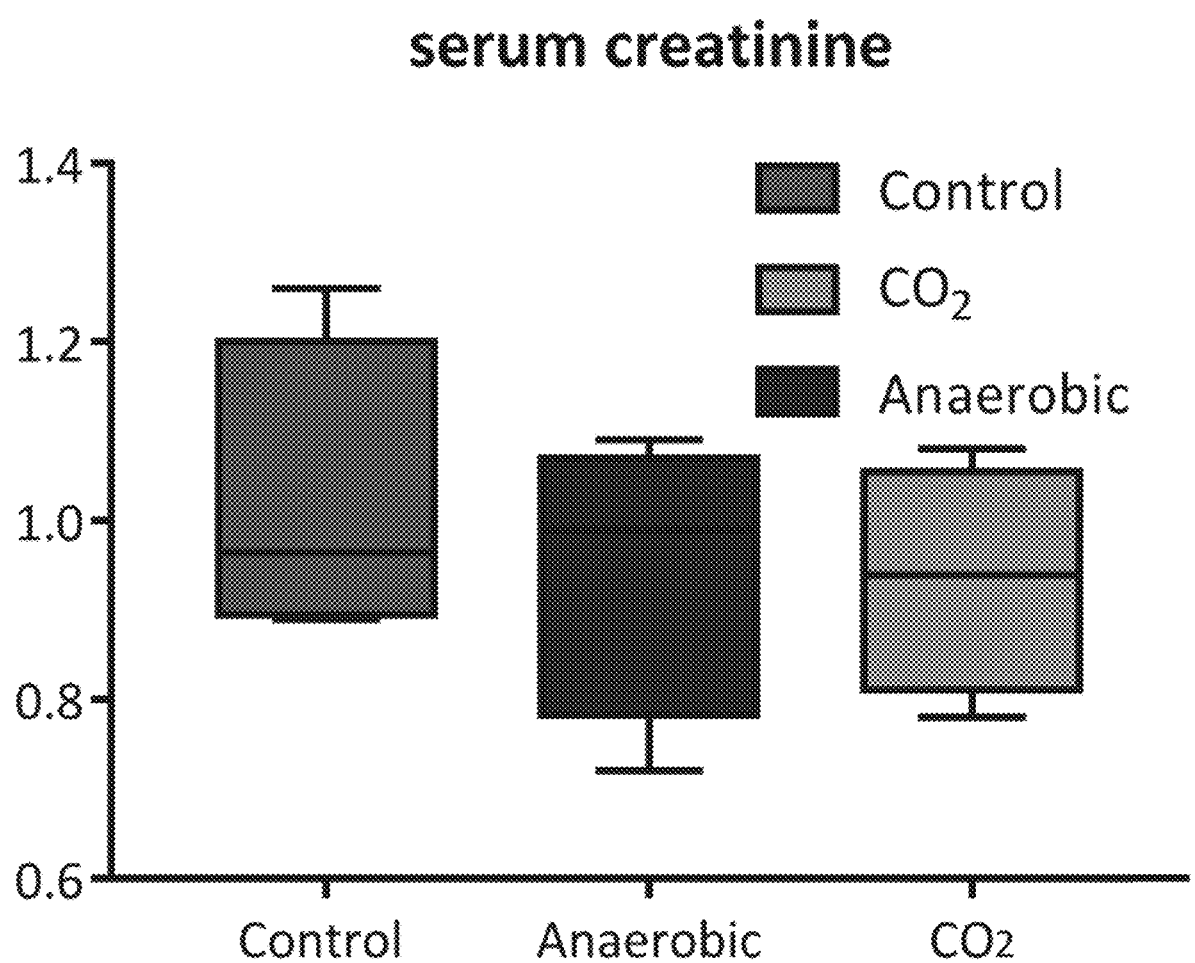
Figure 12A:
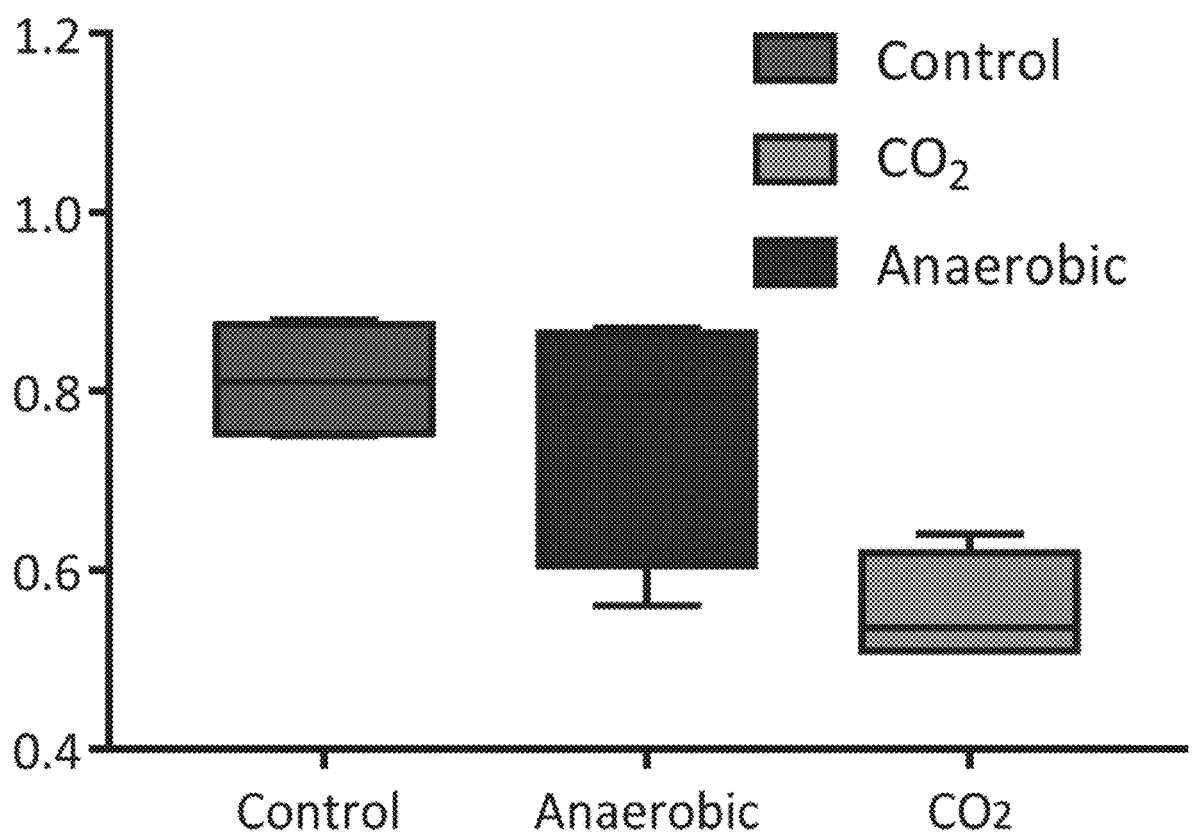
FIGS. 12A and 12B are graphs presenting the results of an exemplary embodiment according to the present disclosure, providing a comparison of the amount of blood urea nitrogen (BUN) in animals resuscitated with control, OR-RBCs, and OCR-RBCs stored for 1 week (FIG. 12A) or 3 weeks (FIG. 12B).
Figure 12B:
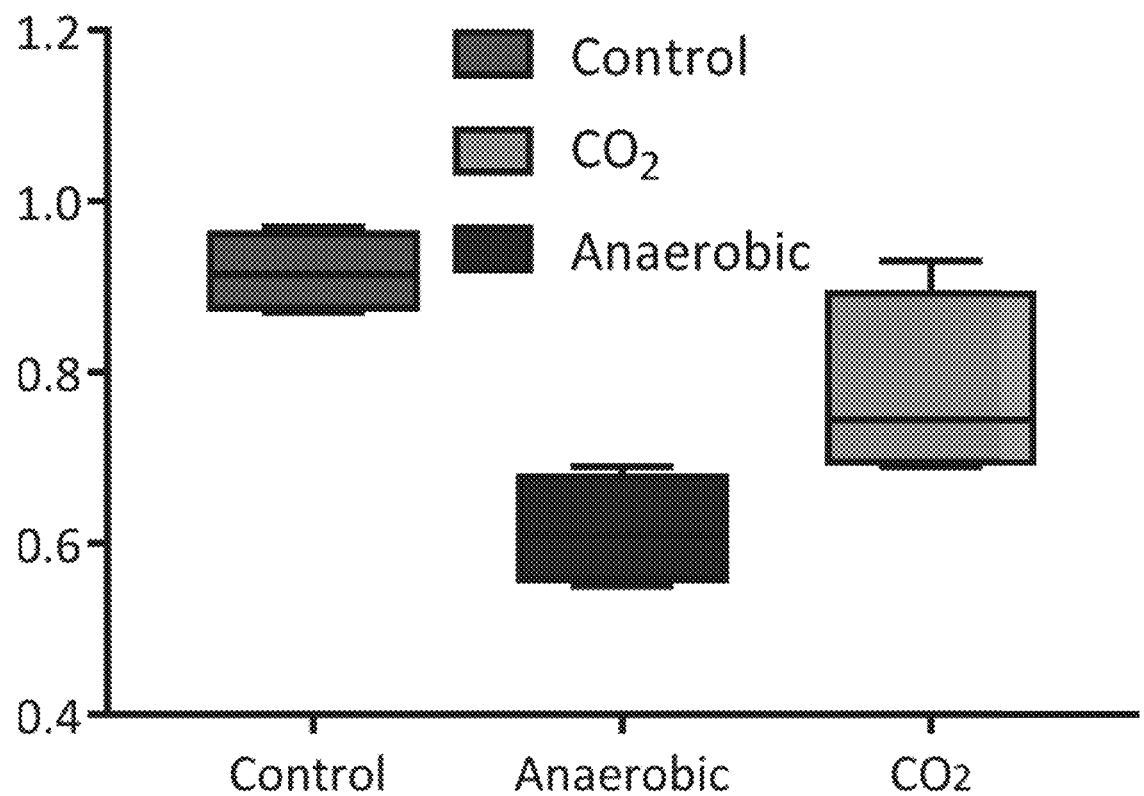
Figure 13A:
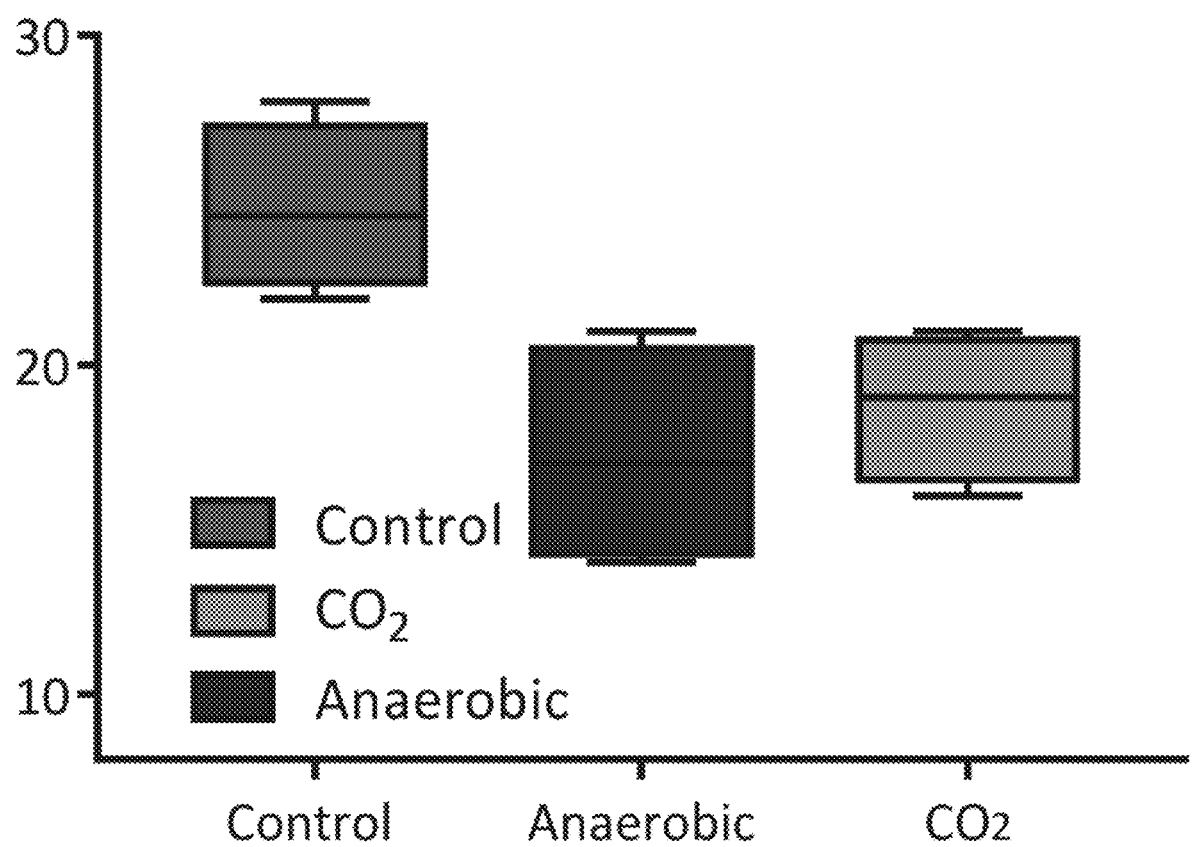
FIGS. 13A and 13B are graphs presenting the results of an exemplary embodiment according to the present disclosure, providing a comparison of the amount of CXCL1 in the liver of animals resuscitated with control, OR-RBCs, and OCR-RBCs stored for 1 week (FIG. 13A) or 3 weeks (FIG. 13B).
Figure 13B:
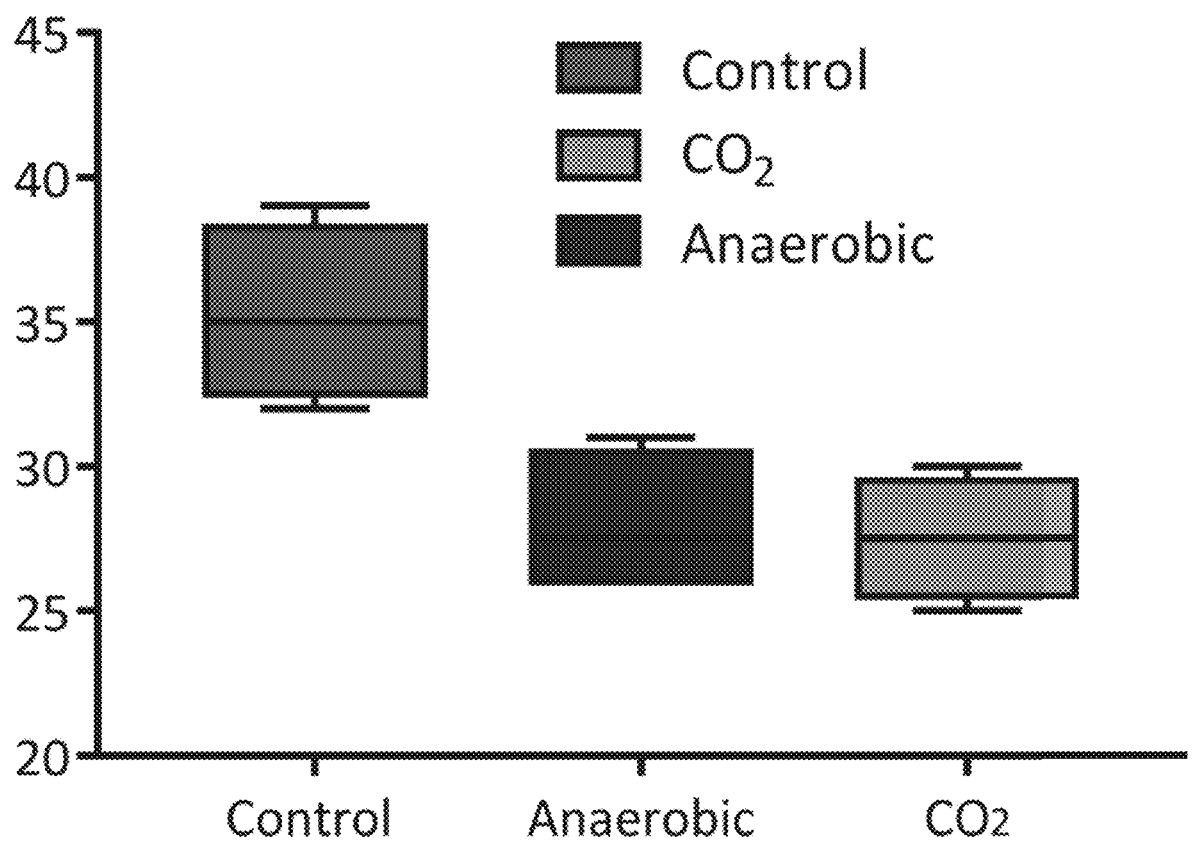
Figure 14A:
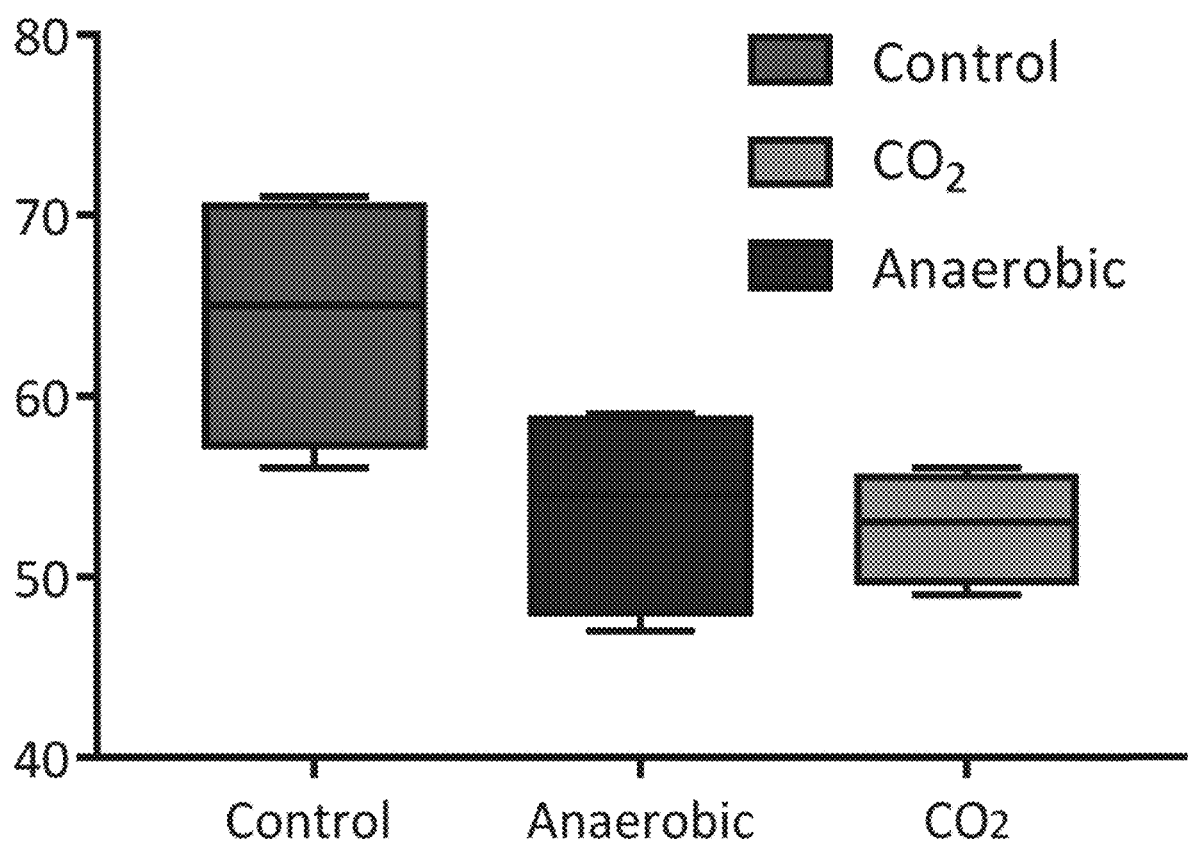
FIGS. 14A and 14B are graphs presenting the results of an exemplary embodiment according to the present disclosure, providing a comparison of the amount of CXCL1 in the spleen of animals resuscitated with control, OR-RBCs, and OCR-RBCs stored for 1 week (FIG. 14A) or 3 weeks (FIG. 14B).
Figure 14B:
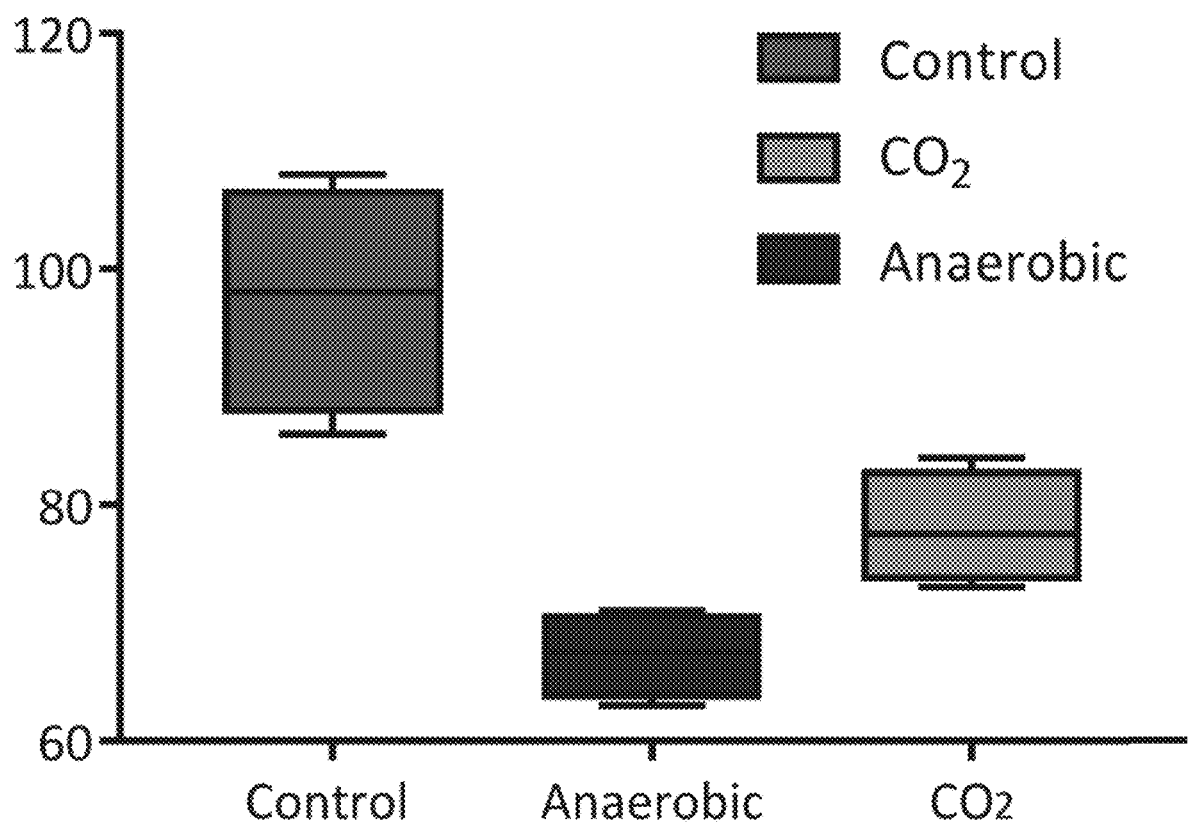
Figure 15A:
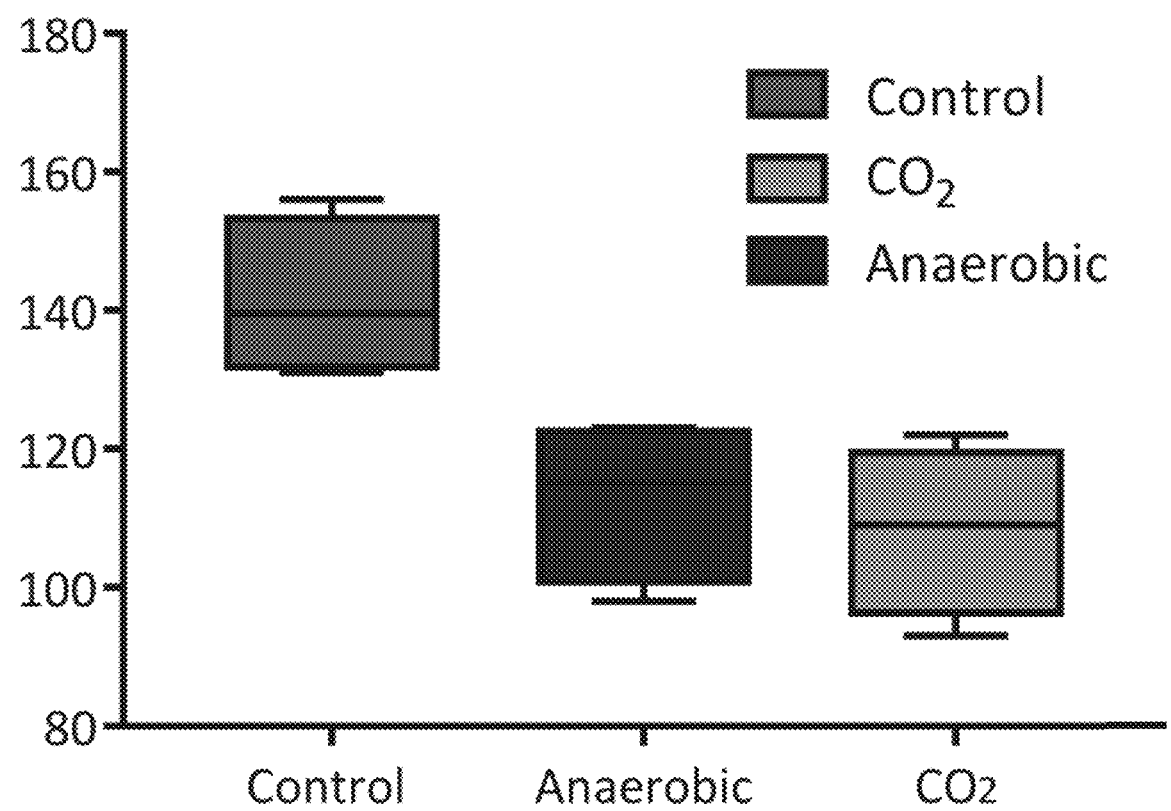
FIGS. 15A and 15B are graphs presenting the results of an exemplary embodiment according to the present disclosure, providing a comparison of the amount of CXCL1 in the lungs of animals resuscitated with control, OR-RBCS, and OCR-RBCs stored for 1 week (FIG. 15A) or 3 weeks (FIG. 15B).
Figure 15B:
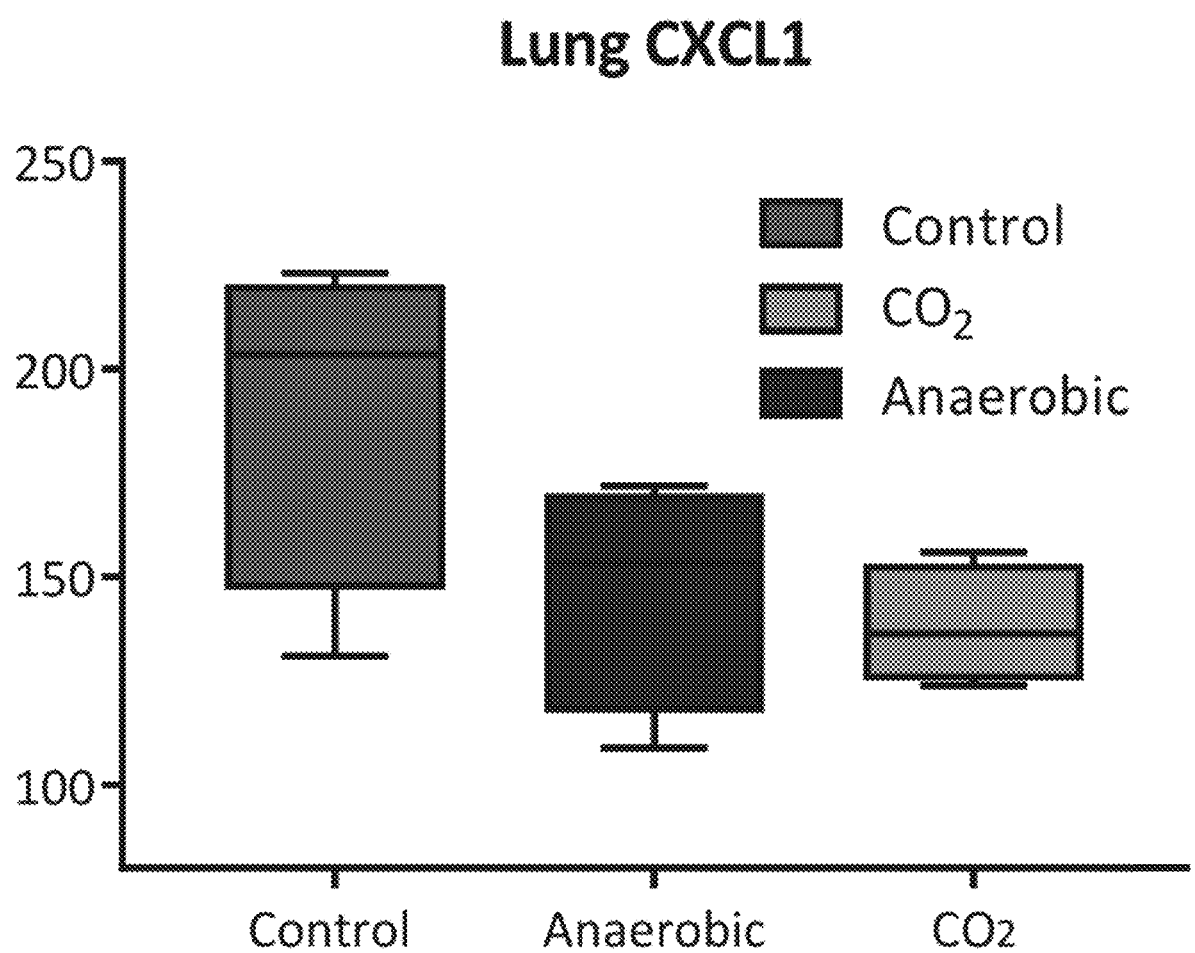
Figure 16A:
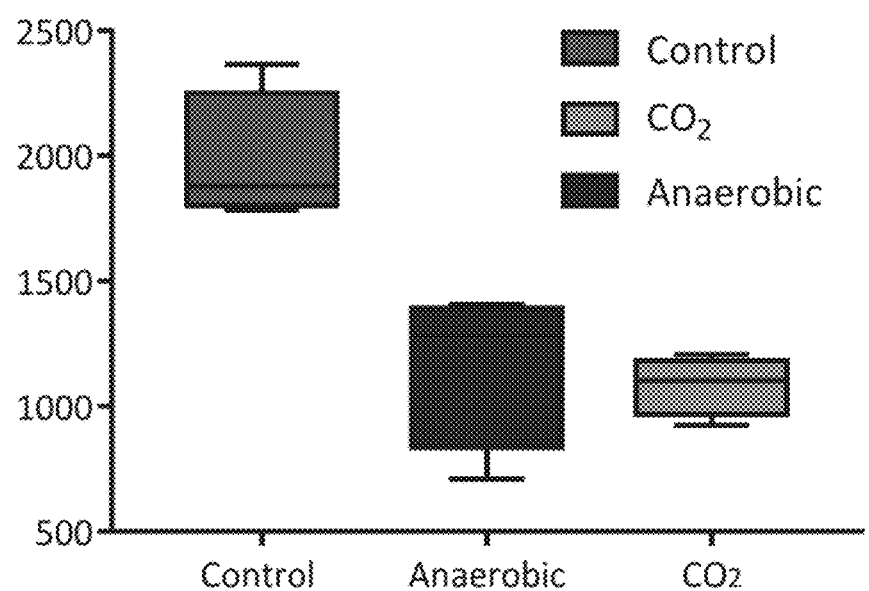
FIGS. 16A and 16B are graphs presenting the results of an exemplary embodiment according to the present disclosure, providing a comparison of the amount of urinary neutrophil gelatinase-associated lipocalin (u-NGAL) in animals resuscitated with control, OR-RBCS, and OCR-RBCS stored for 1 week (FIG. 16A) or 3 weeks (FIG. 16B).
Figure 16B:
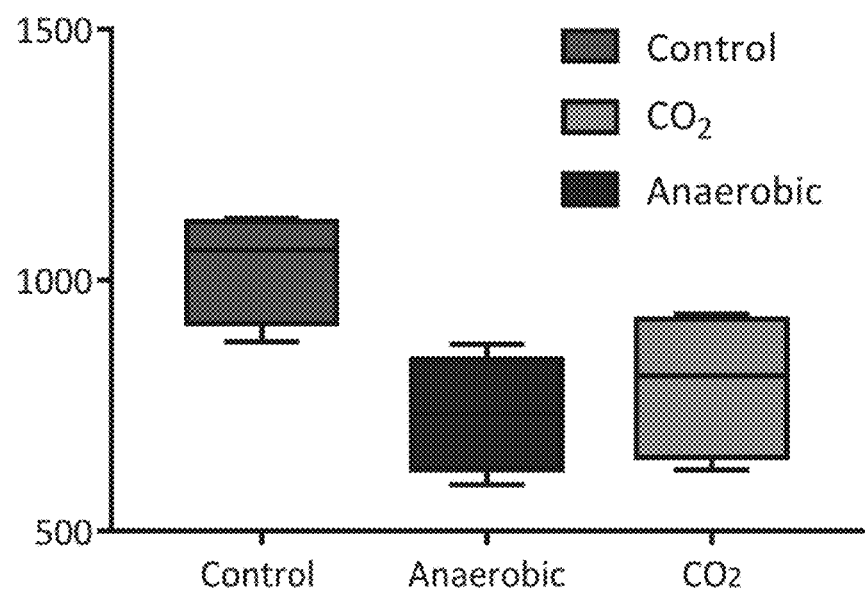
Figure 17A:
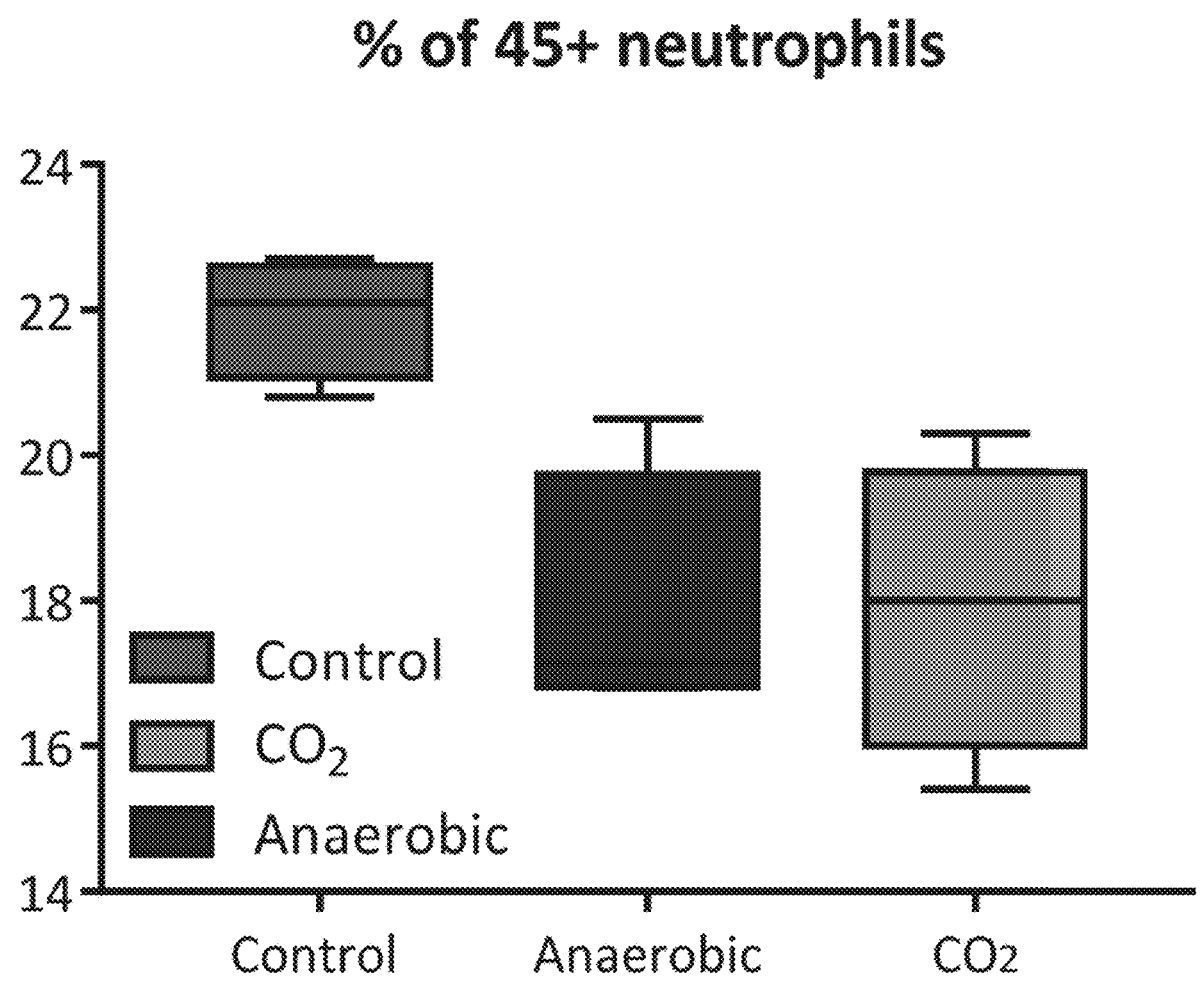
FIGS. 17A and 17B are graphs presenting the results of an exemplary embodiment according to the present disclosure, providing a comparison of the percentage of CD45+ neutrophils in animals resuscitated with control. OR-RBCS, and OCR-RBCS stored for 1 week (FIG. 17A) or 3 weeks (FIG. 17B).
Figure 17B:
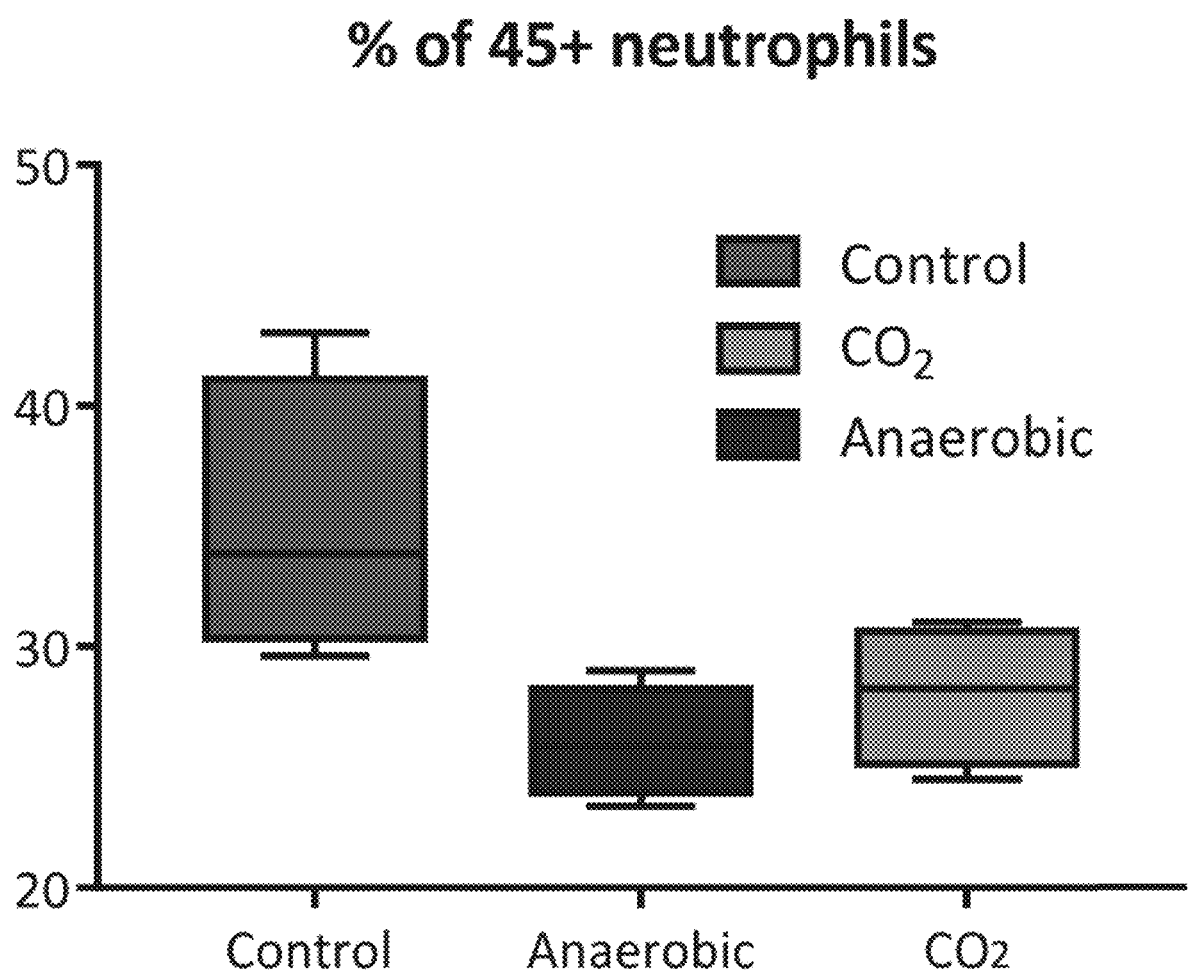
Figure 18A:
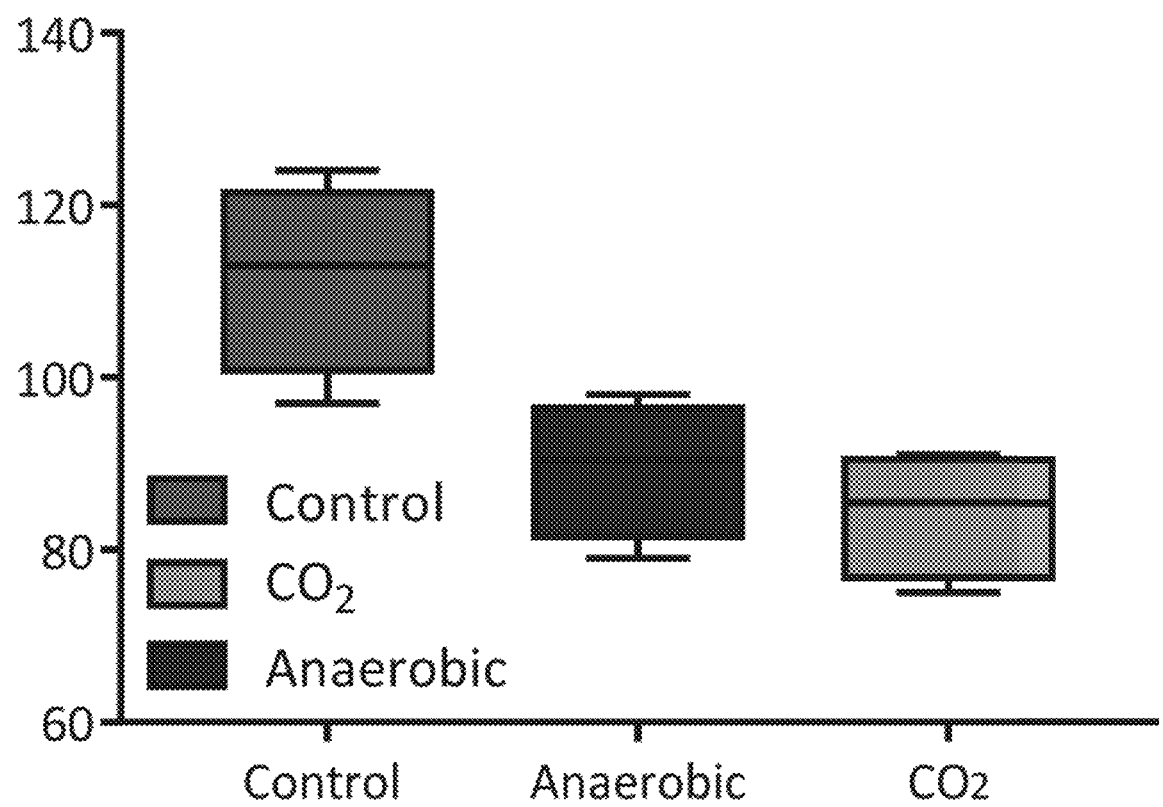
FIGS. 18A and 18B are graphs presenting the results of an exemplary embodiment according to the present disclosure, providing a comparison of the amount of IL-6 in animals resuscitated with control, OR-RBCs, and OCR-RBCs stored for 1 week (FIG. 18A) or 3 weeks (FIG. 18B).
Figure 18B:
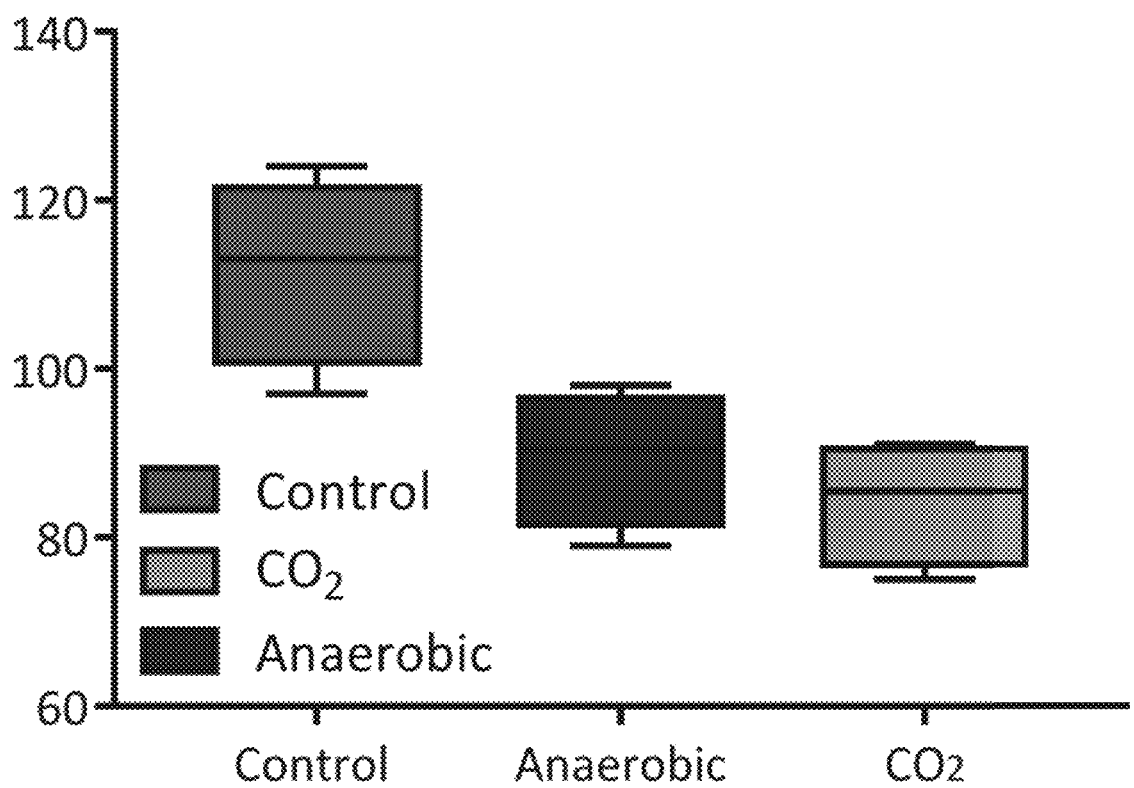

Elevated levels of liver enzymes signify some form of liver damage or injury. Aspartate aminotransferase (AST) and alanine aminotransferase (ALT) levels were analyzed to determine liver damage. Resuscitation with OR and OCR RBCs previously stored for one week (FIG. 9A and FIG. 10A) and three weeks (FIG. 9B and FIG. 10B) reduced AST and ALT levels compared control RBCs stored for the same period of time. Serum creatinine and blood urea nitrogen (BUN) levels were analyzed to determine kidney function. OR and OCR RBCs stored for one week reduced serum creatinine levels greater than 30% compared to control RBCs (FIG. 11A). After three weeks of storage serum creatinine levels of animals treated with control, OR, and OCR RBCs overlap (FIG. 11B). BUN levels are decreased by greater than 30% in animals treated with OCR RBCs stored for one week compared to control (FIG. 12A). BUN levels also decreased by greater than 30% in animals treated with OR RBCs stored for three weeks compared to control (FIG. 12B). Overall, vital organ function was preserved with OR and OCR RBCs compared to control RBCs Liver, spleen and lungs are resected from animals upon completion of the in vivo studies and analyzed for various inflammatory factors including CXCL1, urinary neutrophil gelatinase-associated lipocalin (u-NGAL), IL-6, and neutrophils. CXCL1 is reduced in animals treated with OR and OCR RBCs stored for one or three weeks, compared to control stored for the same period of time (FIG. 13A,B, FIG. 14A, B, and FIG. 15A, B). As shown in FIGS. 16A and B, u-NGAL is reduced in the kidneys of animals treated with OR or OCR RBCs, stored for one or three weeks, compared to control RBCs stored for an equivalent amount of time (FIG. 16). As shown in FIGS. 17 and 18, the percentage of lungs resected from animals with CD45+ neutrophils and the level of IL-6 is significantly decreased in OR and OCR RBCs compared to control RBCs stored for the same period of time. These results show that organ injury and inflammation is decreased in animals treated with OR and OCR RBCs compared to animals treated with control RBCs,

The invention claimed is:

1. A method for reducing the amount of stored blood needed for transfusion in a hemorrhagic trauma patient in need thereof comprising:
   a. obtaining blood having an oxygen saturation of 20% or less;
   b. storing said blood under anaerobic conditions to form hypoxically stored blood; and
   c. providing said hypoxically stored blood to a trauma patient in need of a blood transfusion;
   wherein said hemorrhagic trauma patient in need thereof has elevated blood lactate levels and is in a shock state, and
   wherein said elevated blood lactate levels are reduced and said shock state of said hemorrhagic trauma patient is reversed using a reduced amount of hypoxically stored blood compared to conventionally stored blood.

2. The method of claim 1, wherein the oxygen saturation of said blood is reduced by deoxygenation prior to said storing.

3. The method of claim 1, wherein said blood is whole blood, leukoreduced RBCs, platelet reduced RBCs, or leukocyte and platelet reduced RBCs.

4. The method of claim 1, wherein the amount of stored blood needed by said hemorrhagic trauma patient is reduced by at least 10% relative to the amount of conventionally stored blood.

5. The method of claim 1, wherein the amount of stored blood needed by said hemorrhagic trauma patient is reduced by at least 30% relative to the amount of conventionally stored blood.

6. The method of claim 1, wherein the amount of stored blood needed by said hemorrhagic trauma patient is reduced by at least 50% relative to the amount of conventionally stored blood.

7. The method of claim 1, wherein a hemodynamic function of said hemorrhagic trauma patient is stabilized.

8. The method of claim 1, wherein a hemodynamic function of said hemorrhagic trauma patient is restored.

9. The method of claim 1, wherein said reduction of said elevated blood lactate levels in said hemorrhagic trauma patient is by between 10 and 90% compared to a blood lactate level in a hemorrhagic trauma patient receiving the same the amount of conventionally stored blood.

10. The method of claim 1, wherein said reduction of said elevated blood lactate levels in said hemorrhagic trauma patient is reduced to between 0.5 and 2.5 mmol/L post transfusion.

11. The method of claim 1, further comprising reducing an elevated blood glucose levels of said hemorrhagic trauma patient to between 70 and 120 mg/dL.

12. The method of claim 1, further comprising preventing increased levels of a liver enzyme that indicates liver damage or injury in said hemorrhagic trauma patient.

13. The method of claim 12, wherein said liver enzyme is aspartate aminotransferase (AST) level and said AST level is reduced in said hemorrhagic trauma patient by between 1.5 and 10 fold relative to the AST level in a hemorrhagic trauma patient provided with conventionally stored blood.

14. The method of claim 12, wherein said liver enzyme is alanine aminotransferase (ALT) and said ALT level is reduced in said hemorrhagic trauma patient by between 1.5 and 10 fold relative to the ALT level in a hemorrhagic trauma patient provided with conventionally stored blood.

15. The method of claim 1, further comprising reducing post transfusion elevated markers of kidney function comprising urine neutrophil gelatinase-associated lipocalin (u-NGAL), serum creatinine, or blood urea nitrogen (BUN) levels in said hemorrhagic trauma patient.

16. The method of claim 1, further comprising reducing post transfusion CD45+ neutrophil levels in said hemorrhagic trauma patient.

17. The method of claim 1, further comprising reducing post transfusion blood CXCL1 levels in said hemorrhagic trauma patient.

18. The method of claim 1, further comprising reducing post transfusion blood IL-6 levels in said hemorrhagic trauma patient.

19. The method of claim 1, wherein said hemorrhagic trauma patient has a pre-existing or underlying condition selected from the group consisting of diabetes, ischemic heart disease, systemic inflammatory syndrome brought on by trauma or infection, multiple organ failure brought on by trauma or infection, smoke inhalation, chronic pulmonary obstructive disease, a coagulopathy disorder, and an autoimmune disease.

20. The method of claim 1, wherein said hemorrhagic trauma patient is a blunt force trauma patient.

21. The method of claim 1, wherein said hemorrhagic trauma patient has a low mean arterial pressure prior to transfusion with said hypoxically stored blood.

22. The method of claim 1, wherein said storage period is least 3 weeks.

* * * * *